US005888764A

United States Patent [19]
Mountz et al.

[11] Patent Number: 5,888,764
[45] Date of Patent: Mar. 30, 1999

[54] HUMAN FAS GENE PROMOTER REGION

[75] Inventors: John D. Mountz, Birmingham; Changdan Liu; Jianhua Cheng, both of Alabaster; William J. Koopman, Indian Springs; Tong Zhou, W. Stonebrook Pl., all of Ala.

[73] Assignee: UAB Research Foundation, Birmingham, Ala.

[21] Appl. No.: 377,522

[22] Filed: Jan. 20, 1995

[51] Int. Cl.⁶ .............................. C12N 1/21; C12N 5/10; C12N 15/11; C12P 21/00

[52] U.S. Cl. .................. 435/69.1; 435/172.3; 435/252.3; 435/320.1; 435/325; 536/23.5; 536/23.51; 536/24.1; 536/24.31

[58] Field of Search .............................. 536/24.1, 24.31, 536/23.5, 23.51; 435/320.1, 325, 69.1, 252.3, 172.3; 514/44

[56] References Cited

U.S. PATENT DOCUMENTS 5,663,070   9/1997   Barr et al. .............................. 435/325

FOREIGN PATENT DOCUMENTS 0 510 691 A1   10/1992   European Pat. Off. .

OTHER PUBLICATIONS

Behrmann et al., Eur. J. Immunol. 24:3057–3062 (1994).

"Report and Recommendations of the Panel to Assess the NIH Investment in Research on Gene Therapy," Orkin and Motulsky, Co-chairs, Dec. 7, 1995.

Adachi et al., "Aberrant Transcription Caused by the Insertion of an Early Transposable Element in an Intron of the Fas Antigen Gene of 1pr Mice," *Proc. Natl. Acad. Sci. USA*, 90:1756–1760, Mar. 1993.

Itoh and Nagata, "A Novel Protein Domain Required for Apoptosis, Mutational Analysis of Human Fas Antigen," *The Journal of Biological Chemistry*, 268(15):10932–10937, May 1993.

Alderson et al., "Fas Transduces Activation Signals in Normal Human T Lymphocytes," *J. Exp. Med.*, 178:2231–2235, Dec. 1993.

Biedenkapp et al., "Viral myb Oncogene Encodes a Sequence–Specific DNA–Binding Activity," *Nature*, 335:835–837, Oct. 1988.

Cheng et al., "Protection from Fas–Mediated Apoptosis by a Soluble Form of the Fas Molecule," *Science*, 263:1759–1762, Mar. 1994.

Cheng et al., "SLE Patients Produce Elecvated Serum Levels of a Secreted Form of Fas Protein by Alternative Splicing of the Fas Apoptosis Gene," *Clinical Research*, Abstract, 42(2):141A, 1994.

Collins et al., "Growth Factors as Survival Factors: Regulation of Apoptosis," *BioEssays*, 16(2):133–138, Feb. 1994.

Dorn et al., "conserved major Histocompatibility Complex Class II Boxes–X and Y–are Transcriptional Control Elements and Specifically Bind Nuclear Proteins," *Proc. Natl. Acad. Sci. USA*, 84:6249–6253, Sep. 1987.

Fuchs et al., "Structure of the Human TNF Receptor 1 (p60) Gene (TNRF1) and Localization to Chromosome 12p13," *Genomics*, 13:219–224, 1992.

Gewirtz et al., "$G_1$/S Transition in Normal Human T–Lymphocytes Requires the Nuclear Protein Encoded by c–myb," *Science*, 245:180–183, Jul. 1989.

Goodwin et al., "Cloning of the Human and Murine Interleukin–7 Receptors: Demonstration of a Soluble Form and Homology to a New Recptor Superfamily," *Cell*, 60:941–951, Mar. 1990.

Inazawa et al., "Assignment of the Human Fas Antigen Gene (FAS) to 10q24.1," *Genomics* 14:821–822, 1992.

Itoh et al., "The Polypeptide Encoded by the cDNA for Human Cell Surface Antigen Fas Can Mediate Apoptosis," *Cell*, 66:233–243, Jul. 1991.

Lichter et al., "The Human APO–1 (APT) Antigen Maps to 10q23, a Region That Is Syntenic with Mouse Chromosome 19," *Genomics*, 14:179–180, 1992.

Loenen et al., "Genomic Organization and Chromosomal Localization of the Human CD27 Gene," *The Journal of Immunology*, 149(12):3937–3943, Dec. 1992.

Mosley et al., "The Murine Interleukin–4 Receptor: Molecular Cloning and Characterization of Secreted and Membrane Bound Forms," *Cell*, 59:335–348, Oct. 1989.

Mountz and Steinberg, "Identification of a 5'c–myb Nuclear Protein Binding Site and High Levels of Binding Factors in Nuclear Extracts of 1pr/1pr Lymph Node Cells," *The Journal of Immunology*, 142(1):328–335, Jan. 1989.

Mountz et al., "Autoimmunity and Increased c–myb Transcription," *Science*, 226:1087–1089, Nov. 1984.

Mysler et al., "The Apoptesis 1/Fas Protein in Human Systemic Lupus Erythematosus," *J. Clin. Invest.*, 93:1029–1034, Mar. 1994.

Reed et al., "Sequential Expression of protooncogenes During Lectin–Stimulated Mitogenesis of Normal Human Lymphocytes," *Proc. Natl. Acad. Sci. USA*, 83:3982–3986, Jun. 1986.

(List continued on next page.)

*Primary Examiner*—Johnny F. Railey, II
*Attorney, Agent, or Firm*—Benjamin Aaron Adler

[57] ABSTRACT

Disclosed is a 5' flanking sequence of the human fas gene containing a promoter region. This sequence also contains at least three transcription initiation sites, as well as consensus sequences for AP-1, GF-1, NY-Y, CP-2, EB20, and c-myb. Also disclosed are methods of altering senescence of the immune system by modifying Fas activity in cells to increase or decrease apoptosis. Fas expression and function on T cells from old (22–26-month-old) mice is also compared to young (2-month-old) mice and old CD2-fas transgenic mice. Fas expression and ligand-induced apoptosis was decreased on T cells from old mice compared to young mice. In 26-month-old CD2-fas transgenic mice, Fas and CD44 expression, Fas-induced apoptosis, T cell proliferation and cytokine production were comparable to that of the young mice. These results suggest that T cell senescence with age is associated with defective apoptosis and that the CD2-fas transgene allows the maintenance of Fas apoptosis function and T cell function in aged mice comparable to that of young mice.

46 Claims, 19 Drawing Sheets

OTHER PUBLICATIONS

Sehgal et al., "A Constitutive Promoter Directs Expression of the Nerve Growth Factor Receptor Gene," *Molecular and Cellular Biology,* 8(8):3160–3167, Aug. 1988.

Seldin et al., "IL–2 Modulation of Murine T–Cell Oncogene Expression (42465)," *Proceedings of the Society for Experimental Biology and Medicine,* 184:186–190, 1987.

Su et al., "Dephosphorylation of a 65 kD Protein Associated with Signaling for Fas–Mediated Apoptosis," *Clinical Research,* Abstract, 42(2):14A, 1994.

Suda et al., "Molecular Cloning and Expression of the Fas Ligand, a Novel Member of the Tumor Necrosis Factor Family," *Cell,* 75:1169–1178, Dec. 1993.

Takahashi et al., "Generalized Lymphoproliferative Disease in Mice, Caused by a Point Mutation in the Fas Ligand," *Cell,* 76:969–976, Mar. 1994.

van Houton and Budd, "Accelerated Programmed Cell Death of MRL–1pr/1pr T Lympocytes," *The Journal of Immunology,* 1499(7):2513–2517, Oct. 1992.

Watanabe–Fukunaga et al., "Lymphoproliferation Disorder in Mice Explained by Defects in Fas Antigen that Mediates Apoptosis," *Nature,* 356:314–317, Mar. 1992.

Wu et al., "Autoimmune Disease in Mice Due to Integration of an Endogenous Retrovirus in an Apoptosis Gene," *The Journal of Experimental Medicine,* 178:461–468, Aug. 1993.

Wu et al., "Correction of Accelerated Autoimmune Disease by Early Replacement of the Mutated 1pr Gene with the Normal Fas Apoptosis Gene in the T Cells of Transgenic MRL–1pr/1pr Mice," *Proc. Natl. Acad. Sci. USA,* 91:2344–2348, Mar. 1994.

Zhou et al., "Defective Maintenance of T Cell Tolerance to a Superantigen in MRL–1pr/1pr Mice" *J. Exp. Med.,* 176:1063–1072, Oct. 1992.

```
-1050                                                           -1000
GTAATAACAGAGATGCCCTATACCATCCTCCTTATCCCACTTCTTTTGTGTCTATTAGATGCTCAGAGTGTGTGCACAAG
           -950
GCTGGCACGCCCAGGGTCTTCCTCATGGCACTAACAGTCTACTGAAAGGTGGAACAGAGACAAGCCTATCAACACCTACAA
 -900                                         -850                    GF-1
GACTGGTGGTAAGTGCAGTGACAGATGCAAAACACAGGGTGATGGAAACCCCTCAGGAGGGTAACCTAGATTTGAG
           EBP20          -800                                              -750
GGCCCAAACAGGCTCCAGAAGAAAATGTCAACTGAGAGGAAGCCTGAAGGATGAACAGTGGGCTAAGCAAAGGGTTATTAA
                                 -700
TGTGTTATTAATGGGTTGAATCTAATTGGGAAGGAGAGAGGTTGCAGAGTGCAGAGTGAGGTCAGAGCTTGGTGGACGATGCCAAA
 -650                                                                 -600
GGAATACTGAAACCTTTAGTGTGTCCAGTCTCTGGAACTGCATCAAATTCAGGTTCAGTAATGATGTCATTATCCAAACATA
CCTTCTGTAAAATTCATGCTAAACTACCTAAGAGCTATCTACCGTTCCAAAGCAATAGTGACTTTGAACAGTGTTCACCAG
 -500          GF-1                                           -450
AGCACGAAAGAATTACAAGATTTTTTTTAAAGAAATAATGGCCAGGAAATAATGAGTAACGACAGGAAGTAATTGTG
                                       NF-Y              AP-1               -350
AATGTTAATATAGCTGGGGCTATGCCGATTGGCTTAAGTGTTAGCTTGTTGTTTCCTCTTGAGAAATAAAAACTAAGGGG
                 -300
CCCTCCCCTTTTCAGAGCCCTTCATTTTTCATATGGTTAACTGTCCATTCCAGGAACGTCTCTGTGAGC
         -250                                                       -200
CTCTCATGTTGCAGCCACAAGATGGACAGCCCAGTCAAATGCCCCGCAAGTCTTTCTCTGAGTGACTCCAGCAATTAGCCA
AGGCTCCTGTACCCAGGCAGGACCCTCTGCGCTCTGAGCTCCATTCTCCTTCAAGACCTCCCCAACTTCCCAGGTTGAACTA
 -100                                                          -50
CAGCAGAAGCCTTTAGAAAGGGCAGGAGCCGGCTCTGAGGTCCTCACCTGAAGTGAGATGCCAGCACTGCAGGAACGC
                              GC-rich                               CP2
```

FIG. 2-1

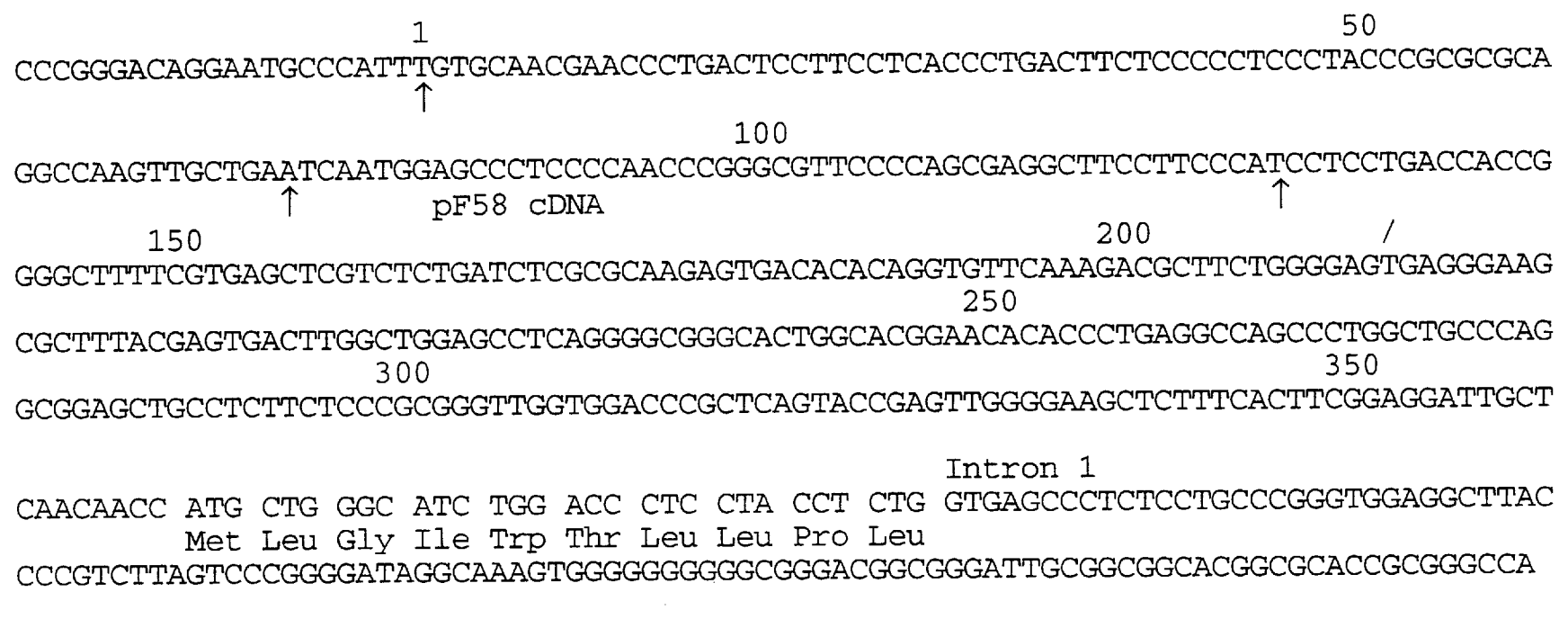

```
   1                                                                      50
CCCGGGACAGGAATGCCCATTTGTCAACGAACCCTGACTTCTCCTCACCCTGACTTCTCCCCTCCCCTACCCGCGGGCA
                    ↑
                    pF58 cDNA
                                       100
GGCCAAGTGCTGAATCAATGGAGCCCTCCCAACCCGGGGGTTCCCCAGCGAGGCTTCCTCCATCCTCCTGACCACCG
                                                                           ↑
      150                              200
GGGCTTTCGTGAGCTCGTCTCTGATCTCGCGCAAGAGTGACACACAGGTGTTCAAAGACGCTTCTGGGGAGTGAGGGAAG
                                        250
CGCTTTACGAGTGACTTGGCTGGAGCCTCAGGGGCGACTGGCACGGAACACACCCTGAGGCCAGCCCTGCCCAG
                  300                                                  350
GCGGGAGCTGCCCCTCTTCCCCGGGGTTGGTGGACCCGCTCAGTACCGAGTCTTTCACTTCGGAGGATTGCT

Intron 1
CAACAACC ATG CTG GGC ATC TGG ACC CTC CTA CCT CTG GTGAGCCCTCCTGCCCGGGTGGAGGCTTAC
         Met Leu Gly Ile Trp Thr Leu Leu Pro Leu

CCCGTCTTAGTCCCGGGGATAGGCAAAGTGCGGGGCGGGGGATTGCGGCGGCACGCGCACCCGCGGGCCA
```

FIG. 2-2

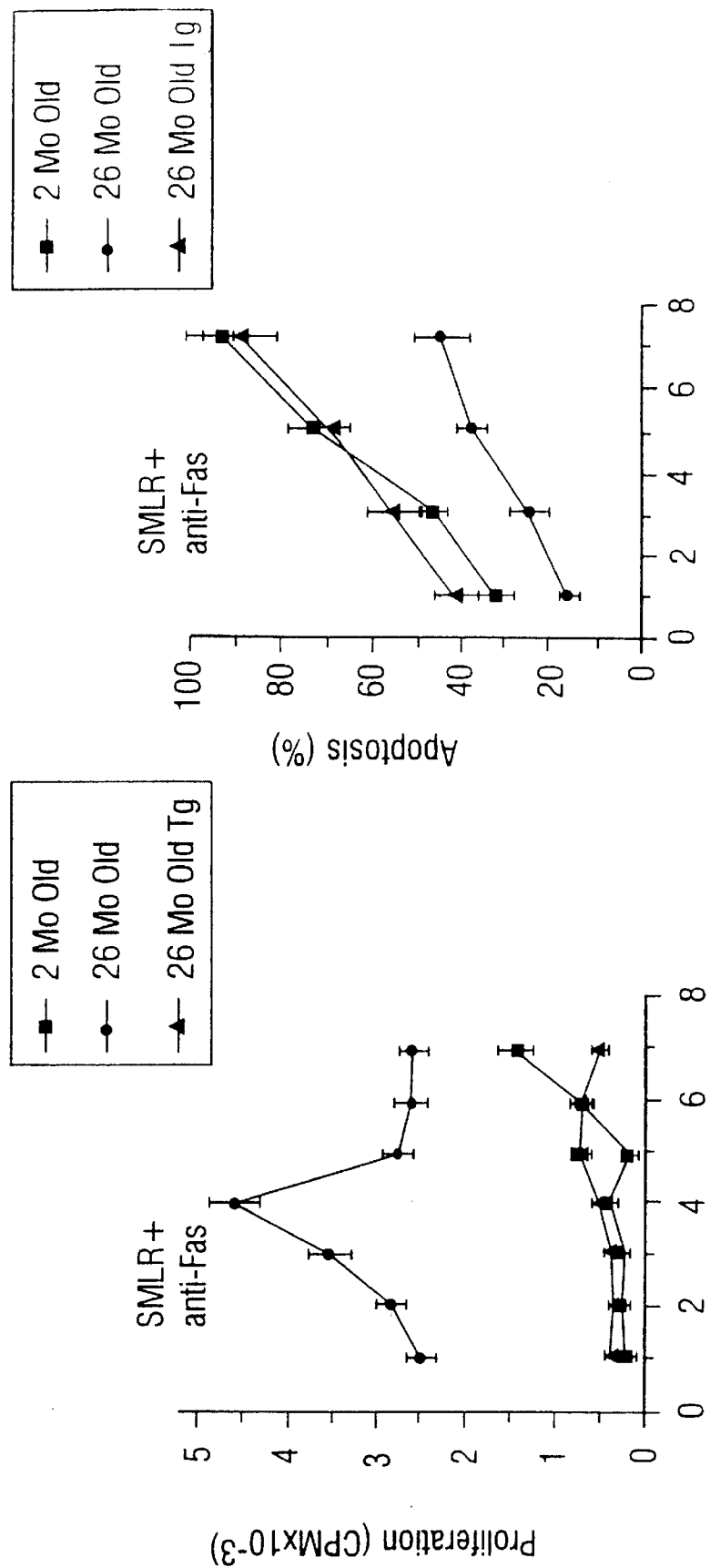

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 1608 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: genomic DNA ( i i i ) HYPOTHETICAL: no ( i v ) ANTI-SENSE: no ( v ) FRAGMENT TYPE:

( v i ) ORIGINAL SOURCE:
        ( A ) ORGANISM: human
        ( F ) TISSUE TYPE: placental ( v i i ) IMMEDIATE SOURCE:
        ( A ) LIBRARY: (FIXII; EMBL- SP6/T7
        ( B ) CLONE: FIX1, FIX2, FIX3; EMBL1, EMBL2, EMBL3

( v i i i ) POSITION IN GENOME:

( i x ) FEATURE:

( x ) PUBLICATION INFORMATION:

( x i ) SEQUENCE DESCRIPTION:SEQ ID NO: 1:

```
GTAATAACAG  AGATGCCCTA  TACCATCCTC  CTTATCCAC   TTCTTTTTGT  GTCTATTAGA      60

TGCTCAGAGT  GTGTGCACAA  GGCTGGCACG  CCCAGGGTCT  TCCTCATGGC  ACTAACAGTC     120

TACTGAAAGG  TGGAACAGAG  ACAAGCCTAT  CAACACCTAC  AAGACTGGTG  GTAAGTGCAG     180
```

-continued

| | | | | | | |
|---|---|---|---|---|---|---|
| TGACAGATGC | AAAACACAGG | GTGATGGAAA | GCCCTCAGGA | GGGTAACCTA | ACCTAGATTT | 240 |
| GAGGGCCCAA | ACAGGCTCCA | GAAGAAAATG | TCAACTGAGA | GGAAGCCTGA | AGGATGAACA | 300 |
| GTGGGCTAAG | CAAAGGGTTA | TTAATGTGTT | ATTAATGGGT | TGAATCTAAT | TGGGAAGGGA | 360 |
| GAGAGGTTGC | AGAGTGAGGT | GCAGAGCTTG | GTGGACGATG | CCAAAGGAAT | ACTGAAACCT | 420 |
| TTAGTGTGTC | CAGTCTGGAA | CTGCATCCAA | ATTCAGGTTC | AGTAATGATG | TCATTATCCA | 480 |
| AACATACCTT | CTGTAAAATT | CATGCTAAAC | TACCTAAGAG | CTATCTACCG | TTCCAAAGCA | 540 |
| ATAGTGACTT | TGAACAGTGT | TCACCAGAGC | ACGAAAGAAT | TACAAGATTT | TTTTTAAAG | 600 |
| AAAATTGGCC | AGGAAATAAT | GAGTAACGAA | GGACAGGAAG | TAATTGTGAA | TGTTTAATAT | 660 |
| AGCTGGGGCT | ATGCGATTTG | GCTTAAGTTG | TTAGCTTTGT | TTTCCTCTTG | AGAAATAAAA | 720 |
| ACTAAGGGGC | CCTCCCTTTT | CAGAGCCCTA | TGGCGCAACA | TCTGTACTTT | TTCATATGGT | 780 |
| TAACTGTCCA | TTCCAGGAAC | GTCTGTGAGC | CTCTCATGTT | GCAGCCACAA | GATGGACAGC | 840 |
| CCAGTCAAAT | GCCCCGCAAG | TCTTTCTCTG | AGTGACTCCA | GCAATTAGCC | AAGGCTCCTG | 900 |
| TACCCAGGCA | GGACCTCTGC | GCTCTGAGCT | CCATTCTCCT | TCAAGACCTC | CCCAACTTCC | 960 |
| CAGGTTGAAC | TACAGCAGAA | GCCTTTAGAA | AGGGCAGGAG | GCCGGCTCTC | GAGGTCCTCA | 1020 |
| CCTGAAGTGA | GATGCCAGCC | ACTGCAGGAA | CGCCCCGGGA | CAGGAATGCC | CATTTGTGCA | 1080 |
| ACGAACCCTG | ACTCCTTCCT | CACCCTGACT | TCTCCCCCTC | CCTACCGCG | CGCAGGCCAA | 1140 |
| GTTGCTGAAT | CAATGGAGCC | CTCCCCAACC | CGGGCGTTCC | CCAGCGAGGC | TTCCTTCCCA | 1200 |
| TCCTCCTGAC | CACCGGGGCT | TTTCGTGAGC | TCGTCTCTGA | TCTCGCGCAA | GAGTGACACA | 1260 |
| CAGGTGTTCA | AAGACGCTTC | TGGGGAGTGA | GGGAAGCGGT | TTACGAGTGA | CTTGGCTGGA | 1320 |
| GCCTCAGGGG | CGGGCACTGG | CACGGAACAC | ACCCTGAGGC | CAGCCCTGGC | TGCCCAGGCG | 1380 |
| GAGCTGCCTC | TTCTCCCGCG | GGTTGGTGGA | CCCGCTCAGT | ACGGAGTTGG | GGAAGCTCTT | 1440 |
| TCACTTCGGA | GGATTGCTCA | ACAACCATGC | TGGGCATCTG | GACCCTCCTA | CCTCTGGTGA | 1500 |
| GCCCTCTCCT | GCCCGGGTGG | AGGCTTACCC | CGTCTTAGTC | CCGGGGATAG | GCAAAGTGGG | 1560 |
| GCGGGCGCGG | GACGGCGGGA | TTGCGGCGGC | ACGGCGCACC | GCGGGCCA | | 1608 |

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE:
        ( A ) DESCRIPTION: amino acid ( i i i ) HYPOTHETICAL: no ( i v ) ANTI-SENSE: no ( v ) FRAGMENT TYPE: N-terminus ( v i ) ORIGINAL SOURCE:
        ( A ) ORGANISM: human
        ( F ) TISSUE TYPE: placental ( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO:2:

Met Leu Gly Ile Trp Thr Leu Leu Pro Leu (2) INFORMATION FOR SEQ ID NO:3:

(i) SEQUENCE CHARACTERISTICS:
        (A) LENGTH: 7 bp
        (B) TYPE: nucleic acid
        (C) STRANDEDNESS: double-stranded
        (D) TOPOLOGY: linear (ii) MOLECULE TYPE:
        (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:
        (A) NAME/KEY: AP-1 consensus sequence (x) PUBLICATION INFORMATION:

(xi) SEQUENCE DESCRIPTION:SEQ ID NO: 3:

TGANTMA        7

(2) INFORMATION FOR SEQ ID NO:4:

(i) SEQUENCE CHARACTERISTICS:
        (A) LENGTH: 7 bp
        (B) TYPE: nucleic acid
        (C) STRANDEDNESS: double-stranded
        (D) TOPOLOGY: linear (ii) MOLECULE TYPE:
        (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:
        (A) NAME/KEY: CP2 consensus sequence (x) PUBLICATION INFORMATION:

(xi) SEQUENCE DESCRIPTION:SEQ ID NO: 4:

AGCCACT        7

(2) INFORMATION FOR SEQ ID NO:5:

(i) SEQUENCE CHARACTERISTICS:
        (A) LENGTH: 6 bp
        (B) TYPE: nucleic acid
        (C) STRANDEDNESS: double-stranded
        (D) TOPOLOGY: linear (ii) MOLECULE TYPE:
        (A) DESCRIPTION: nucleic acid (  i i i  ) HYPOTHETICAL: no (  i v  ) ANTI-SENSE: no (  v  ) FRAGMENT TYPE:

(  v i  ) ORIGINAL SOURCE:

(  v i i  ) IMMEDIATE SOURCE:

(  v i i i  ) POSITION IN GENOME:

(  i x  ) FEATURE:
    ( A ) NAME/KEY: GF-1 consensus sequence (  x  ) PUBLICATION INFORMATION:

(  x i  ) SEQUENCE DESCRIPTION:SEQ ID NO: 5:

C T A T C A            6

( 2 ) INFORMATION FOR SEQ ID NO:6:

( i ) SEQUENCE CHARACTERISTICS:
        ( A ) LENGTH: 5 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:
        ( A ) NAME/KEY: NF-Y consensus sequence ( x ) PUBLICATION INFORMATION:

( x i ) SEQUENCE DESCRIPTION:SEQ ID NO: 6:

A T T G G            5

( 2 ) INFORMATION FOR SEQ ID NO:7:

( i ) SEQUENCE CHARACTERISTICS:
        ( A ) LENGTH: 6 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:
        ( A ) NAME/KEY: Myb consensus sequence ( x ) PUBLICATION INFORMATION:

( x i ) SEQUENCE DESCRIPTION:SEQ ID NO: 7:

C A A C T G                                                                                                                                                                  6

( 2 ) INFORMATION FOR SEQ ID NO:8:

( i ) SEQUENCE CHARACTERISTICS:
        ( A ) LENGTH: 8 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:
        ( A ) NAME/KEY: EBP20 consensus sequence ( x ) PUBLICATION INFORMATION:

( x i ) SEQUENCE DESCRIPTION:SEQ ID NO: 8:

G T G G W W W G                                                                                                                                                              8

( 2 ) INFORMATION FOR SEQ ID NO:9:

( i ) SEQUENCE CHARACTERISTICS:
        ( A ) LENGTH: 18 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:
        ( A ) AUTHORS:Itoh, N.
            Yonehara, S.
            Ishii, A.
            Yonehara, M.
            Mizushima, S- I.
            Sameshima, M.
            Hase, A.
            Seto, Y.
            Nagata, S.
        ( B ) TITLE: The polypeptide encoded by the cDNA for human cell
            surface antigen Fas can mediate apoptosis.
        ( C ) JOURNAL: Cell
        ( D ) VOLUME: 66

(F) PAGES: 233-234
(G) DATE: 1991

(x i) SEQUENCE DESCRIPTION:SEQ ID NO: 9:

AGCGGTTTAC GAGTGACT                                                                                              18

(2) INFORMATION FOR SEQ ID NO:10:

(i) SEQUENCE CHARACTERISTICS:
        (A) LENGTH: 20 bp
        (B) TYPE: nucleic acid
        (C) STRANDEDNESS: single- stranded
        (D) TOPOLOGY: linear (i i) MOLECULE TYPE:
        (A) DESCRIPTION: other nucleic acid (i i i) HYPOTHETICAL: no (i v) ANTI-SENSE: no (v) FRAGMENT TYPE:

(v i) ORIGINAL SOURCE:

(v i i) IMMEDIATE SOURCE:

(v i i i) POSITION IN GENOME:

(i x) FEATURE:

(x) PUBLICATION INFORMATION:
        (A) AUTHORS:Itoh, N.
            Yonehara, S.
            Ishii, A.
            Yonehara, M.
            Mizushima, S- I.
            Sameshima, M.
            Hase, A.
            Seto, Y.
            Nagata, S.
        (B) TITLE: The polypeptide encoded by the cDNA for human cell
            surface antigen Fas can mediate apoptotis.
        (C) JOURNAL: Cell
        (D) VOLUME: 66
        (F) PAGES: 233-234
        (G) DATE: 1991

(x i) SEQUENCE DESCRIPTION:SEQ ID NO: 10:

TGGTTCCAGG TATCTGCTTC                                                                                            20

(2) INFORMATION FOR SEQ ID NO:11:

(i) SEQUENCE CHARACTERISTICS:
        (A) LENGTH: 21 bp
        (B) TYPE: nucleic acid
        (C) STRANDEDNESS: single- stranded
        (D) TOPOLOGY: linear (i i) MOLECULE TYPE:
        (A) DESCRIPTION: other nucleic acid (i i i) HYPOTHETICAL: no (i v) ANTI-SENSE: no (v) FRAGMENT TYPE:

(v i) ORIGINAL SOURCE:

(v i i) IMMEDIATE SOURCE:

(v i i i) POSITION IN GENOME:

(i x) FEATURE:

(x) PUBLICATION INFORMATION:
  (A) AUTHORS: Itoh, N.
      Yonehara, S.
      Ishii, A.
      Yonehara, M.
      Mizushima, S-I.
      Sameshima, M.
      Hase, A.
      Seto, Y.
      Nagata, S.
  (B) TITLE: The polypeptide encoded by the cDNA for human cell surface antigen Fas can mediate apoptosis.
  (C) JOURNAL: Cell
  (D) VOLUME: 66
  (F) PAGES: 233-234
  (G) DATE: 1991

(xi) SEQUENCE DESCRIPTION:SEQ ID NO: 11:

CTCAGGGTGT GTTCCGTGCC A    21

(2) INFORMATION FOR SEQ ID NO:12:

(i) SEQUENCE CHARACTERISTICS:
      (A) LENGTH: 34 bp
      (B) TYPE: nucleic acid
      (C) STRANDEDNESS: double-stranded
      (D) TOPOLOGY: linear (ii) MOLECULE TYPE:
      (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 12:

TCTGGTGAGC CCTCTCCTGC CCGGGTGGAG GCTT    34

(2) INFORMATION FOR SEQ ID NO:13:

(i) SEQUENCE CHARACTERISTICS:
      (A) LENGTH: 35 bp
      (B) TYPE: nucleic acid
      (C) STRANDEDNESS: double-stranded
      (D) TOPOLOGY: linear (ii) MOLECULE TYPE:
      (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

( x i ) SEQUENCE DESCRIPTION:SEQ ID NO: 13:

TAAAATTCTC TTCATGCTTT TATTTTAGAG GTTCT 35

( 2 ) INFORMATION FOR SEQ ID NO:14:

( i ) SEQUENCE CHARACTERISTICS:
        ( A ) LENGTH: 34 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 14:

CCAGGTATGT TACACAAACA TCCAGAGATT ACAG 34

( 2 ) INFORMATION FOR SEQ ID NO:15:

( i ) SEQUENCE CHARACTERISTICS:
        ( A ) LENGTH: 35 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 15:

CAAACACTTG CTCCTTTTTT CCTTGGGCAG GTGAA 35

( 2 ) INFORMATION FOR SEQ ID NO:16:

( i ) SEQUENCE CHARACTERISTICS:
        ( A ) LENGTH: 34 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 16:

CATGGTAAGA GTCTTAAAAT GCAATTGAAA GAGG 34

(2) INFORMATION FOR SEQ ID NO:17:

(i) SEQUENCE CHARACTERISTICS:
(A) LENGTH: 35 bp
(B) TYPE: nucleic acid
(C) STRANDEDNESS: double-stranded
(D) TOPOLOGY: linear (ii) MOLECULE TYPE:
(A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 17:

TAACTAATAG TTTCCAAACT GATTTTCTAG GCTTA 35

(2) INFORMATION FOR SEQ ID NO:18:

(i) SEQUENCE CHARACTERISTICS:
(A) LENGTH: 34 bp
(B) TYPE: nucleic acid
(C) STRANDEDNESS: double-stranded
(D) TOPOLOGY: linear (ii) MOLECULE TYPE:
(A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

( x i ) SEQUENCE DESCRIPTION:SEQ ID NO: 18:

CCAAGTAAGT TTTAGTCTTT CTCTGATTAA AACA 34

( 2 ) INFORMATION FOR SEQ ID NO:19:

( i ) SEQUENCE CHARACTERISTICS:
        ( A ) LENGTH: 35 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 19:

TTTGAATTTC TCCTGTATTT TTTTTCTAG ATGTG 35

( 2 ) INFORMATION FOR SEQ ID NO:20:

( i ) SEQUENCE CHARACTERISTICS:
        ( A ) LENGTH: 35 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 20:

GAAGGTAATT ATTTTTTTA CGGTTATATC CTCCT 35

( 2 ) INFORMATION FOR SEQ ID NO:21:

( i ) SEQUENCE CHARACTERISTICS:
        ( A ) LENGTH: 35 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 21:

CATATAATAT GCCAATGTTC CAACCTACAG GATCC 35

(2) INFORMATION FOR SEQ ID NO:22:

(i) SEQUENCE CHARACTERISTICS:
 (A) LENGTH: 34 bp
 (B) TYPE: nucleic acid
 (C) STRANDEDNESS: double-stranded
 (D) TOPOLOGY: linear (ii) MOLECULE TYPE:
 (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 22:

TGGGGTAAGT TCTTGCTTTG TTCAAACTGC AGAT 34

(2) INFORMATION FOR SEQ ID NO:23:

(i) SEQUENCE CHARACTERISTICS:
 (A) LENGTH: 35 bp
 (B) TYPE: nucleic acid
 (C) STRANDEDNESS: double-stranded
 (D) TOPOLOGY: linear (ii) MOLECULE TYPE:
 (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

( x i ) SEQUENCE DESCRIPTION:SEQ ID NO: 23:

TGAGTTGATA AAATTTCTTT GTTCTTTCAG TGAAG　　　　　　　　　　　　　　　　　　35

( 2 ) INFORMATION FOR SEQ ID NO:24:

( i ) SEQUENCE CHARACTERISTICS:
          ( A ) LENGTH: 34 bp
          ( B ) TYPE: nucleic acid
          ( C ) STRANDEDNESS: double- stranded
          ( D ) TOPOLOGY: linear ( i i ) MOLECULE TYPE:
          ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 24:

TCCTGTAGGT ATTGAAATAG GTATCAGCTT TCCT　　　　　　　　　　　　　　　　　　34

( 2 ) INFORMATION FOR SEQ ID NO:25:

( i ) SEQUENCE CHARACTERISTICS:
          ( A ) LENGTH: 35 bp
          ( B ) TYPE: nucleic acid
          ( C ) STRANDEDNESS: double- stranded
          ( D ) TOPOLOGY: linear ( i i ) MOLECULE TYPE:
          ( A ) DESCRIPTION: nucleic acid ( i i i ) HYPOTHETICAL: no ( i v ) ANTI-SENSE: no ( v ) FRAGMENT TYPE:

( v i ) ORIGINAL SOURCE:

( v i i ) IMMEDIATE SOURCE:

( v i i i ) POSITION IN GENOME:

( i x ) FEATURE:

( x ) PUBLICATION INFORMATION:

( x i ) SEQUENCE DESCRIPTION:SEQ ID NO: 25:

CTTTCTCTGC TTCCATTTTT TGCTTTCTAG GAAAC　　　　　　　　　　　　　　　　　　35

( 2 ) INFORMATION FOR SEQ ID NO:26:

( i ) SEQUENCE CHARACTERISTICS:
          ( A ) LENGTH: 34 bp
          ( B ) TYPE: nucleic acid
          ( C ) STRANDEDNESS: double- stranded
          ( D ) TOPOLOGY: linear ( i i ) MOLECULE TYPE:
          ( A ) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 26:

TCTGGTAAGG CTTTTATCAT TTTATTTCAT AGAG                                          34

(2) INFORMATION FOR SEQ ID NO:27:

(i) SEQUENCE CHARACTERISTICS:
                (A) LENGTH: 35 bp
                (B) TYPE: nucleic acid
                (C) STRANDEDNESS: double-stranded
                (D) TOPOLOGY: linear (ii) MOLECULE TYPE:
                (A) DESCRIPTION: nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 27:

TCAGACTATT TTCTATTTTC TATTTTTCAG ATGTT                                         35

HUMAN FAS GENE PROMOTER REGION

The U.S. Government owns rights in the present invention pursuant to grant numbers P60 AR20614, P50 AI23694, P01 AR03555 and R01 AI30744 from the National Institutes of Health.

BACKGROUND OF THE INVENTION

1. Field of the Invention

The present invention relates generally to the field of molecular biology. In particular, it relates to methods and compositions relating to the regulation of gene transcription and polypeptide expression.

2. Description of the Related Art

Programmed cell death or apoptosis is a fundamental mechanism in the development of an organism, and occurs from embryogenesis throughout life (Vaux et al., 1993). Much remains to be learned about the apoptotic process at the molecular level, however the more classical type of programmed cell death is thought to require activation of a set of genes that lead to DNA fragmentation and subsequent apoptotic morphological changes.

A membrane receptor-like protein, Fas, has been reported to be involved in this process. Fas antigen is a membrane-associated polypeptide that consists of 306 amino acids in mouse (Watanabe-Fukunaga et al., 1992a), and sequence analysis of the full length Fas cDNA revealed that the human Fas molecule has 335 amino acids, with a calculated molecular weight of 37,729 kda. (Itoh et al., 1991; Oehm et al., 1992). The human Fas antigen has a signal peptide of 16 amino acid residues at its amino terminus, an extracellular domain of 157 amino acid residues, a hydrophobic transmembrane domain of 17 amino acid residues and a cytoplasmic tail of 146 amino acids at its carboxyl terminus. The extracellular domain can be divided into three cysteine-rich subdomains. The cytoplasmic region contains the domain that is required for initiation of the apoptotic response (Itoh and Nagata, 1993).

Structural homology places Fas in the superfamily including tumor necrosis factor receptors, nerve growth factor receptor and CD40 (Watanabe-Fukunaga et al., 1992a; Itoh et al., 1991; Oehm et al., 1992; Itoh & Nagata, 1993). In the immune system, the occurrence of massive cell death in the thymus is at least partly due to an apoptotic process mediated through signaling by the Fas antigen (Yonehara et al., 1989; Trauth et al., 1989) that is also involved in T cell-mediated cytotoxicity (Rouvier et al., 1993). Abnormally expressed Fas is observed in the lpr mutant mouse strains (Watanabe-Fukunaga et al., 1992b; Adachi et al., 1993; Wu et al., 1993) that display lymphoproliferative disorders (Frizzera et al., 1989; Saito et al., 1992).

Fas gene expression has been found to be expressed in several tissues, including thymus, spleen, ovary and heart, and on a number of cell types, including activated T- and B-lymphocytes (Watanabe-Fukunaga et al., 1992; Itoh et al., 1991). Its expression is up-regulated by interferon-g (Itoh et al., 1991). Abnormal expression of Fas is observed in the lpr mutant mouse strains which display lymphoproliferative disorders and spontaneous autoimmune disease (Watanabe-Fukunaga et al., 1992; Wu et al., 1993; Adachi et al., 1993). Correction of abnormal expression of Fas in Fas-transgenic MRL-lpr/lpr mice partially abrogates lymphoproliferation and autoantibody production characteristic of this strain (Wu et al., 1994). Recently, the inventors identified an alternatively spliced form of Fas mRNA in human (Cheng et al., 1994). This mRNA encodes a soluble, secreted form of the Fas molecule due to the deletion of an exon encoding the Fas transmembrane domain. Elevated levels of this soluble form of Fas were demonstrated in some patients with SLE. Moreover, administration of soluble Fas to mice at levels comparable to these present in SLE resulted in apparent inhibition of in vivo apoptosis of lymphocytes.

Sequence analysis of the full length human Fas cDNA has revealed that the human Fas molecule has 335 amino acids, with a calculated molecular weight of 37,729 daltons (Itoh et al., 1991; Oehm et al., 1992; Itoh and Nagata, 1993). Structural homology places Fas in the superfamily including tumor necrosis factor (TNF)[3] receptors, nerve growth factor (NGF) receptor and CD40 (Watanabe-Fukunaga et al., 1992; Itoh et al., 1991; Oehm et al., 1992; Mallett and Barclay, 1991).

Fas gene has been mapped to the long arm of chromosome 10 in human (Inazawa et al., 1992; Lichter et al., 1992) and the conserved syntatic segment of chromosome 19 in mouse (Watanabe-Fukunaga et al., 1992). However, The gene structure of either human or mouse Fas has not yet been characterized. In this study, we have isolated the human chromosomal DNA for the human Fas apoptotic molecule, determined the exon/intron organization of the gene and characterized the promoter region.

Age-related immune dysfunctions of T cells include thymic involution (Hadden et al., 1992), decreased T cell response to mitogens or antigens (Powers and Belshe, 1993; Flurkey et al., 1992; Kirschmann and Murasko, 1992; Song et al., 1993; McElhaney et al., 1992), altered cytokine expression (Ernst et al., 1993; Ershler,, 1993; al-Rayes et al., 1992; Daynes and Araneo, 1992) and altered phenotype (Okumura et al., 1993; Howard et al., 1992; Thoman et al., 1993). The decrease in spleen or LN T cell responsiveness has been related to an increase in senescent memory T cells (Okumura et al., 1993; Thoman et al., 1993), which exhibit defective phosphorylation after stimulation (Shi and Miller, 1993; Heyeck and Berg, 1993; Patel and Miller, 1992; Witkowski and Miller, 1993; Saini and Sei, 1993). Thymic involution has been proposed to be due either to defects in thymocyte precursors derived from stem cells or a defect in expression of thymic factors or growth factors required for normal T cell development (Hadden et al., 1992; Candore et al., 1992; Goso et al., 1993; Fridkis-Hareli et al., 1992; Li et al., 1992). Recent evidence indicates that depletion of thymocyte stem cells can not completely account for thymic involution with age (Mehr et al., 1993). Evidence to support an age-related deficiency of growth factors has been provided by the observation that replacement of growth factors or hormones can inhibit thymic involution or T cell dysfunction with aging (Hadden et al., 1992; Candore et al., 1992; Goso et al., 1993; Fridkis-Hareli et al., 1992; Li et al., 1992).

SUMMARY OF THE INVENTION

The present invention, in a general and overall sense, arises from the characterization of the human Fas gene, and the surprising discovery of a promoter region at the 5' flanking region of the gene. The Fas promoter region may be operatively linked to a cDNA encoding Fas, to heterologous genes, or it may be free of structural genes.

Exons and Introns of the Human Fas Gene[a]

| Splice Acceptor | | Exon No. | Exon Size (bp) | Splice Donor | | Intron Size | SEQ ID No. |
|---|---|---|---|---|---|---|---|
| | | 1 | >224 | ... T CTG Leu | gtgagccctctcctgcccgggtggaggctt | >14 kb | 12 |
| taaaattctcttcatgcttttattttagag | GTT CT ... Val (-6) | 2 | 166 | ... CCA G G | gtatgttacacaaacatccagagattacag | ~3.0 kb | 13; 14 |
| caaacacttgctccttttttccttgggcag | GT GAA ... ly (50) | 3 | 138 | ... CAT G G | gtaagagtcttaaaatgcaattgaaagagg | ~1.0 kb | 15; 16 |
| taactaatagtttccaaactgattttctag | GC TAA ... ly (96) | 4 | 109 | ... CC AA Ly | gtaagttttagtctttctctgattaaaaca | ~1.5 kb | 17; 18 |
| tttgaatttctcctgtattttttttctag | A TGT G .. s (132) | 5 | 62 | ... GAA G G | gtaattattttttttacggttatatcctcct | 152 bp | 19; 20 |
| catataatatgccaatgttccaaccta-cag | GA TCC ... ly(153) | 6 | 63 | ... TGG G V | gtaagttcttgctttgttcaaactgcagat | ~1.2 kb | 21; 22 |
| tgagttgataaaatttctttgttctttcag | TG AAG ... al (174) | 7 | 83 | ... T CCT Pro | gtaggtattgaaataggtatcagctttcct | ~1.2 kb | 23; 24 |
| ctttctctgcttccattttttgcttctag | GAA AC ... Glu(202) | 8 | 25 | ... TCT G A | gtaaggcttttatcattttatttcatagag | ~0.7 kb | 25; 26 |
| tcagactattttctattttctattttcag | AT GTT ... sp(210) | 9 | 1664 | ... G GTC Val(319) | TAG ( ... 3'-UTR 1335 bp) | | 27 |

[a]Exon sequence is shown by capital letters; intron sequence, by lower case. Numbers in parentheses indicate amino acid residue position in mature Fas molecule.

The Fas promoter region has been found to contain transcription factor binding sites, including but not limited to those for AP-1 (TGANT$^C/_A$A)(SEQ ID NO:3) at position -451 to -449, CP2 protein (AGCCACT)(SEQ ID NO:4) at position -38 to -32, GF-1 (CTATCA)(SEQ ID NO:5) at position -554 to -549 and -928 to -923, NF-Y (ATTGG) (SEQ ID NO:6) at position -471 to -467 and -726 to -722, Myb (SEQ ID NO:7) at position -803 to -798, and EBP20 (GTGG$^A/_T^A/_T^A/_T$G) (SEQ ID NO:8) at position -908 to -890.

The inventors show a strong molecular connection between an increase in c-myb expression in Fas or Fas ligand mutant mice and the structure of the Fas gene. Because activated T cell has been shown to increase expression of c-myb mRNA (Gewirtz et al., 1989; Reed et al., 1986) as well as Fas mRNA (Mysler et al., 1994), it is likely that Myb is involved in the increase of Fas expression in these cells.

The Fas promoter region is set forth in SEQ ID NO:1 and FIG. 2 is a continuous sequence of about 1270 base pairs of the 5' upstream sequence of the Fas gene. As previously stated, the promoter region may be free of structural genes, or it may be operatively linked to an expressible DNA coding region. As used herein, an expressible DNA coding region includes heterologous genes and cDNA's that are capable of being expressed to form peptides, polypeptides, and proteins.

In certain embodiments, the invention contemplates a DNA molecule comprising a DNA segment having the Fas transcription factor binding sites in combination with a structural gene not ordinarily under the transcriptional control of the transcription factor binding sites. The structural gene and transcription factor binding sites are combined in a manner such that the The DNA segments of the instant invention may be capable of expressing a growth factor, a growth factor receptor, a cytokine, a nuclear regulatory factor, a tumor suppressor, an anti-cancer agent, or a peptide hormone. Examples of these expressible coding regions may be for, but not limited to TGFα, TGFβ, EGF, FGF, TNFα, p53, c-myc, c-fos, GCSF, or GMCSF.

The following table, Table I, lists a number of known defined structural genes, along with descriptive references, which may be employed in the context of the control sequences of the present invention. It should, however, be appreciated that this table is in no way intended to be an exhaustive or all-inclusive listing, and it is included herein for the convenience of the reader.

TABLE I

Selected Cloned Structural Genes

| Gene | Clone Type* | Reference |
|---|---|---|
| activin | porcine-cDNA | Mason AJ, Nat. 318:659, 1985 |
| adenosine deaminase | h-cDNA | Wiginton DA, PNAS, 80:7481, 1983 |
| angiotensinogen I | r-cDNA | Ohkubo H, PNAS, 80:2196, 1983 |
| | r-gDNA | Tanaka T, JBC, 259:8063, 1984 |
| antithrombin III | h-cDNA | Bock SC, NAR 10:8113, 1982 |
| | h-cDNA and gDNA | Prochownik EV, JBC, 258:8389, 1983 |
| antitrypsin, alpha I | h-cDNA | Kurachi K, PNAS, 78:6826, 1981 |
| | h-gDNA | Leicht M, Nat, 297:655, 1982 |
| | RFLP | Cox DW, AJHG, 36:134S, 1984 |
| apolipoprotein A-I | h-cDNA, h-gDNA | Shoulders CC, NAR, 10:4873, 1982 |
| | RFLP | Karathanasis SK, Nat, 301:718, 1983 |
| | h-gDNA | Karathanasis SK, PNAS, 80:6147, 1983 |

TABLE I-continued

Selected Cloned Structural Genes

| Gene | Clone Type* | Reference |
|---|---|---|
| apolipoprotein A-II | h-cDNA | Sharpe CR, NAR, 12:3917, 1984 |
|  | Chr | Sakaguchi AY, AJHG, 36:207S, 1984 |
|  | h-cDNA | Knott, TJ, BBRC, 120:734, 1984 |
| apolipoprotein C-I | h-cDNA | Knott TJ, NAR, 12:3909, 1984 |
| apolipoprotein C-II | h-cDNA | Jackson CL, PNAS, 81:2945, 1984 |
|  | h-cDNA | Mykelbost O, JBC, 259:4401, 1984 |
|  | h-cDNA | Fojo SS, PNAS, 81:6354, 1984 |
|  | RFLP | Humphries SE, C Gen, 26:389, 1984 |
| apolipoprotein C-III | h-cDNA and gDNA | Karathanasis SK, Nat, 304:371, 1983 |
|  | h-cDNA | Sharpe CR, NAR, 12:3917, 1984 |
| apolipoprotein E | h-cDNA | Breslow JL, JBC, 257:14639, 1982 |
| atrial natriuretic factor | h-cDNA | Oikawa S, Nat, 309:724, 1984 |
|  | h-cDNA | Nakayama K, Nat, 310:699, 1984 |
|  | h-cDNA | Zivin RA, PNAS, 81:6325, 1984 |
|  | h-gDNA | Seidman CE, Sci, 226:1206; 1984 |
|  | h-gDNA | Nemer M, Nat, 312:654, 1984 |
|  | h-gDNA | Greenbert BI, Nat, 312:656, 1984 |
| chorionic gonadotropin, alpha chain | h-cDNA | Fiddes JC, Nat, 281:351, 1981 |
|  | RFLP | Boethby M, JBC, 256:5121, 1981 |
| chorionic gonadotropin, beta chain | h-cDNA | Fiddes JC, Nat, 286:684, 1980 |
|  | h-gDNA | Boorstein WR, Nat, 300:419, 1982 |
|  | h-gDNA | Talmadge K, Nat, 307:37, 1984 |
| chymosin, pro (rennin) | bovine-cDNA | Harris TJR, NAR, 10:2177, 1982 |
| complement, factor B | h-cDNA | Woods DE, PNAS, 79:5661, 1982 |
|  | h-cDNA and gDNA | Duncan R. PNAS, 80:4464, 1983 |
| complement C2 | h-cDNA | Bentley DR, PNAS, 81:1212, 1984 |
|  | h-gDNA (C2, C4, and B) | Carroll MC, Nat, 307:237, 1984 |
| complement C3 | m-cDNA | Domdey H, PNAS, 79:7619, 1983 |
|  | h-gDNA | Whitehead AS, PNAS, 79:5021, 1982 |
| complement C4 | h-cDNA and gDNA | Carroll MC, PNAS, 80:264, 1983 |
|  | h-cDNA | Whitehead AS, PNAS, 80:5387, 1983 |
| complement C9 | h-cDNA | DiScipio RC, PNAS, 81:7298, 1984 |
| corticotropin releasing factor | sheep-cDNA | Furutani Y, Nat, 301:537, 1983 |
|  | h-gDNA | Shibahara S, EMBO J, 2:775, 1983 |
| epidermal growth factor | m-cDNA | Gray A, Nat, 303:722, 1983 |
|  | m-cDNA | Scott J, Sci, 221:236, 1983 |
|  | h-gDNA | Brissenden JE, Nat, 310:781, 1984 |
| epidermal growth factor, receptor, oncogene c-erb B | h-cDNA and Chr | Lan CR, Sci, 224:843, 1984 |
| epoxide dehydratase | r-cDNA | Gonzalez FJ, JBC, 256:4697, 1981 |
| erythropoietin | h-cDNA | Lee-Huang S, PNAS, 81:2708, 1984 |
| esterase inhibitor, C1 | h-cDNA | Stanley KK, EMBO J, 3:1429, 1984 |
| expression sequences | m-gDNA | Fried M, PNAS, 80:2117, 1983 |
| factor VIII | h-cDNA and gDNA | Gitschier J. Nat, 312:326, 1984 |
|  | h-cDNA | Toole JJ, Nat, 312:342, 1984 |
| factor IX, Christmas factor | h-cDNA | Kutachi K, PNAS, 79:6461, 1982 |
|  | h-cDNA | Choo KH, Nat, 299:178, 1982 |
|  | RFLP | Camerino G, PNAS, 81:498, 1984 |
|  | h-gDNA | Anson DS, EMBO J, 3:1053, 1984 |
| factor X | h-cDNA | Leytus SP, PNAS, 81:3699, 1984 |
| fibrinogen A alpha, B beta, gamma | h-cDNA | Kant JA, PNAS, 80:3953, 1983 |
|  | h-gDNA (gamma) | Fornace AJ, Sci, 224:161, 1984 |
|  | h-cDNA (alpha gamma) | Iman AMA, NAR, 11:7427, 1983 |
|  | h-gDNA (gamma) | Fornace AJ, JBC, 259:12826, 1984 |
| gastrin releasing peptide | h-cDNA | Spindel ER, PNAS, 81:5699, 1984 |
| glucagon, prepro | hamster-cDNA | Bell GI, Nat, 302:716, 1983 |
|  | h-gDNA | Bell GI, Nat, 304,368, 1983 |
| growth hormone | h-cDNA | Martial JA, Sci, 205:602, 1979 |
|  | h-gDNA | DeNoto FM, NAR, 9:3719, 1981 |
|  | GH-like gene | Owerbach D, Sci, 209:289, 1980 |
| growth hormone RF, somatocrinin | h-cDNA | Gubler V, PNAS, 80:4311, 1983 |
|  | h-cDNA | Mayo KE, Nat, 306:86, 1983 |
| hemopexin | h-cDNA | Stanley KK, EMBO J, 3:1429, 1984 |
| inhibin | porcine-cDNA | Mason AJ, Nat, 318:659, 1985 |
| insulin, prepro | h-gDNA | Ullrich A, Sci, 209:612, 1980 |
| insulin-like growth factor I | h-cDNA | Jansen M, Nat, 306:609, 1983 |
|  | h-cDNA | Bell GI, Nat, 310:775, 1984 |
|  | Chr | Brissenden JE, Nat, 310:781, 1984 |

TABLE I-continued

Selected Cloned Structural Genes

| Gene | Clone Type* | Reference |
|---|---|---|
| insulin-liek growth | h-cDNA | Bell GI, Nat, 310:775, 1984 |
| factor II | h-gDNA | Dull TJ, Nat, 310:777, 1984 |
|  | Chr | Brissenden JE, Nat, 310:781, 1984 |
| interferon, alpha | h-cDNA | Maeda S, PNAS, 77:7010, 1980 |
| (Leukocyte), | h-cDNA (8 distinct) | Goeddel DV, Nat, 290:20, 1981 |
| multiple | h-gDNA | Lawn RM, PNAS, 78:5435, 1981 |
|  | h-gDNA | Todokoro K, EMBO J, 3:1809, 1984 |
|  | h-gDNA | Torczynski RM, PNAS, 81:6451, 1984 |
| interferon, beta | h-cDNA | Taniguchi T, Gene, 10:11, 1980 |
| (fibroblast) | h-gDNA | Lawn RM, NAR, 9:1045, 1981 |
|  | h-gDNA (related) | Sehgal PB, PNAS, 80:3632, 1983 |
|  | h-gDNA (related) | Sagar AD, Sci, 223:1312, 1984 |
| interferon, gamma | h-cDNA | Gray PW, Nat, 295:503, 1982 |
| (immune) | g-gDNA | Gray PW, Nat, 298:859, 1982 |
| interleukin-1 | m-cDNA | Lomedico PT, Nat, 312:458, 1984 |
| interleukin-2, T-cell | h-cDNA | Devos R, NAR, 11:4307, 1983 |
| growth factor | h-cDNA | Taniguchi T, Nat, 302:305, 1983 |
|  | h-gDNA | Hollbrook NJ, PNAS, 81:1634, 1984 |
|  |  | Siegel LJ, Sci, 223:175, 1984 |
| interleukin-3 | m-cDNA | Fung MC, Nat, 307:233, 1984 |
| kininogen, two forms | bovine-cDNA | Nawa H, PNAS, 80:90, 1983 |
|  | bovine-cDNA and gDNA | Kitamura N, Nat, 305:545, 1983 |
| luteinizing hormone, beta subunit | h-gDNA and Chr | Talmadge K, Nat, 307:37, 1984 |
| luteinizing hormone releasing hormone | h-cDNA and gDNA | Seeburg PH, Nat, 311:666, 1984 |
| lymphotoxin | h-cDNA and gDNA | Gray PW, Nat, 312:721, 1984 |
| mast cell growth factor | m-cDNA | Yokoya T, PNAS, 81:1070, 1984 |
| nerve growth factor, | m-cDNA | Scott J, Nat, 302:538, 1983 |
| beta subunit | h-gDNA | Ullrich A, Nat, 303:821, 1983 |
|  | Chr | Franke C, Sci, 222:1248, 1983 |
| oncogene, c-sis, PGDF chain A | h-gDNA | Dalla-Favera R, Nat, 295:31, 1981 |
|  | h-cDNA | Clarke MF, Nat, 308:464, 1984 |
| pancreatic polypeptide and icosapeptide | h-cDNA | Boel E, EMBO J, 3:909, 1984 |
| parathyroid hormone, | h-cDNA | Hendy GN, PNAS, 78:7365, 1981 |
| prepro | h-gDNA | Vasicek TJ, PNAS, 80:2127, 1983 |
| plasminogen | h-cDNA and gDNA | Malinowski DP, Fed. P, 42:1761, 1983 |
| plasminogen activator | h-cDNA | Edlund T, PNAS, 80:349, 1983 |
|  | h-cDNA | Pennica D, Nat, 301:214, 1983 |
|  | h-gDNA | Ny T, PNAS, 81:5355, 1984 |
| prolactin | h-cDNA | Cooke NE, JBC, 256:4007, 1981 |
|  | r-gDNA | Cooke NE, Nat, 297:603, 1982 |
| proopiomelanocortin | h-cDNA | DeBold CR, Sci, 220:721, 1983 |
|  | h-gDNA | Cochet M, Nat, 297:335, 1982 |
| protein C | h-cDNA | Foster D, PNAS, 81:4766, 1984 |
| prothrombin | bovine-cDNA | MacGillivray RTA, PNAS, 77:5153, 1980 |
| relaxin | h-gDNA | Hudson P, Nat, 301:628, 1983 |
|  | h-cDNA (2 genes) | Hudson P, EMBO J, 3:2333, 1984 |
|  | Chr | Crawford RJ, EMBO J, 3:2341, 1984 |
| renin, propro | h-cDNA | Imai T, PNAS, 80:7405, 1983 |
|  | h-gDNA | Hobart PM, PNAS 81:5026, 1984 |
|  | h-gDNA | Miyazaki H, PNAS, 81:5999, 1984 |
|  | Chr | Chirgwin JM, SCMG, 10:415, 1984 |
| somatostatin | h-cDNA | Shen IP, PNAS 79:4575, 1982 |
|  | h-gDNA snd Ri-lP | Naylot SI, PNAS, 80:2686, 1983 |
| tachykinin, prepro, | bovine-cDNA | Nawa H, Nat, 306:32, 1983 |
| substances P & K | bovine-gDNA | Nawa H, Nat, 312:729, 1984 |
| urokinase | h-cDNA | Verde P, PNAS, 81:4727, 1984 |
| vasoactive intestinal peptide, prepro | h-cDNA | Itoh N, Nat, 304:547, 1983 |
| vasopressin | r-cDNA | Schmale H, EMBO J, 2:763, 1983 |

*cDNA . . . complementary DNA
Chr . . . chromosome
gDNA . . . genomic DNA
RFLP . . . restriction fragment polymorphism
h—human
m—mouse
r—rat The invention also contemplates that the nucleic acid sequences comprise at least a 10 nucleotide long contiguous stretch that corresponds to the contiguous nucleic acid sequence of SEQ ID NO:1.

Nucleic acid molecules having contiguous stretches of 10–14, 20, 30, 50, or even of 100–200 nucleotides or so, that corresponds to, or are complementary to, sequences from SEQ ID NO:1 will have utility as hybridization probes or primers. These probes will be useful in a variety of hybridization embodiments, which also include Southern and Northern blotting in connection with analyzing Fas expression in various mammalian cells. The total size of fragment, as well as the size of the complementary stretch(es), will ultimately depend on the intended use or application of the particular nucleic acid segment. Fragments generally finding use in hybridization embodiments may have lengths of complementary regions that vary between about 10–14 or 20 and about 100 nucleotides, or even up to the full length sequences of 1270 nucleotides (SEQ ID NO:1), according to the complementary sequences one wishes to detect.

The term "heterologous structural gene" refers to structural genes other than the naturally-associated gene, and the term "structural gene" refers to any DNA segment which may be both transcribed and translated by a cell.

To obtain a DNA sequence containing the transcription factor binding sites, one would simply prepare a DNA segment comprising the nucleotides in the region as set forth in SEQ ID NO:1. This can be achieved, for example, by employing restriction enzymes to excise an appropriate piece of DNA. Any one, or two, of an extensive range of restriction enzymes could be chosen following an analysis of the sequences around broadly around −1072 and 325 to determine the existence of appropriate restriction sites. If desired, for example, for subsequent ligation strategies, one could even create a particular restriction site by genetic engineering. The use of such restriction enzymes to excise a portion of DNA will be generally known to those of skill in the art in light of the present disclosure.

It is proposed that the transcription factor binding sites of the present invention may confer a regulatory capability regardless of their orientation with respect to the transcribed strand of DNA. Moreover, it is proposed that there may not necessarily be a requirement that these sequences be placed in a particular position with respect to the site of transcription initiation. Thus, they may act in a fashion similar to enhancer elements in this regard.

It is also proposed that the Fas promoter with associated transcription factor binding sites may be introduced into a heterologous gene in multiple copies, either in a forward or reversed orientation, and perhaps obtain a much improved regulatory capability. Moreover, multiple units need not be placed in an adjacent conformation and may be separated by numerous random nucleotides and still retain their improved regulatory and promotion capability.

As noted, these transcription factor binding sites are advantageously employed by locating said sequences upstream from and proximal to a transcription initiation site of a selected heterologous structural gene. Depending on the particular structural gene employed, these control elements may provide some benefit when located up to 300 nucleotides upstream of a transcription initiation site, as measured from the 3' end of the control sequence.

It is contemplated that these binding sites will prove useful in the context of a wide array of genes which have been characterized to date. Although, as disclosed in more detail below, it is believed that the sequences will prove useful in the context of virtually any structural gene, it is further believed that these sequences will be of particular benefit in the context of human and related structural genes such as the genes for TGFα and other growth factors, EGF and other growth factor receptors, p53 and other tumor suppressor genes, interferon, lymphokines such as interleukins I, VI and VIII, tumor necrosis factor, and numerous other genes as disclosed herein.

Recombinant DNA methodology

Important aspects of the present invention concern isolated DNA segments and recombinant vectors that comprise the Fas promoter region, and the creation and use of recombinant host cells through the application of DNA technology, that Fas or other heterologous proteins, polypeptides, or peptides.

As used herein, the term "DNA segment" refers to a DNA molecule that has been isolated free of total genomic DNA of a particular species. Therefore, a DNA segment that comprises the Fas promoter region refers to a DNA segment that contains Fas promoter region sequences yet is isolated away from, or purified free from, total human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified Fas promoter region refers to a DNA segment including Fas coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the region of interest, in this case the Fas coding region, forms the significant part of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that contain a Fas promoter region in accordance with SEQ ID NO:1, corresponding to that isolated from a human. Moreover, in other particular embodiments, the invention concerns isolated DNA segments and recombinant vectors incorporating heterologous DNA sequences that encode heterologous proteins.

Recombinant Vectors and Probes

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as E. coli LE392.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture,* 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV, retroviral) source, or may be provided by the host cell chromosomal replication mechanism. If the vector is integrated into the host cell chromosome, the latter is often sufficient.

This invention provides novel nucleic acid segments, probes, primers and vectors for use in molecular biological embodiments, including diagnostic and screening assays and protein expression. The inventors determined through sequence analysis the exon/intron organization of genomic DNA for the human Fas apoptotic protein, and have characterized the promoter region.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a certain contiguous stretch identical to, or complementary to, SEQ ID NO:1, but that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in the context of both proteins and nucleic acids, means any length between the quoted ranges, such as 14, 15, 16, 17, 18, 19, 20, etc.; 21, 22, 23, etc; 30, 31, 32, etc.; 50, 51, 52, 53, etc.; 100, 101, 102, 103, etc.; 150, 151, 152, 153, etc.; including, for nucleic acids, all integers through the 200–500; 500–1,000; and up to 1,000–2,000 and the like.

It will also be understood that this invention is not limited to the particular nucleic acid and amino acid sequences of SEQ ID NO:1 and SEQ ID NO:2. Recombinant vectors and isolated DNA segments may therefore variously include the Fas coding regions themselves, coding regions bearing selected alterations or modifications in the basic coding region or they may encode larger polypeptides that nevertheless include Fas-coding regions.

In regard to functionally equivalent proteins or peptides, such may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test Fas mutants in order to further examine their activity at the molecular level.

One may also prepare fusion proteins and peptides where the Fas coding regions are aligned within the same expression unit with other proteins or peptides having desired functions, such as for purification or immunodetection purposes (e.g., proteins that may be purified by affinity chromatography and enzyme label coding regions, respectively). This is readily achieved by the standard DNA manipulation techniques well known to those of skill in the art (see e.g., Sambrook et al. incorporated herein by reference).

Recombinant vectors form important further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a fas gene(s), e.g., in T cells, as may be obtained by isolating the 5' non-coding sequences located upstream of the coding segment or exon, for example, using recombinant cloning and/or PCR technology, in connection with the compositions disclosed herein.

In connection with expression embodiments to prepare recombinant Fas proteins and peptides, it is contemplated that DNA segments encoding the entire Fas protein may be used, as may shorter DNA segments where needed to direct the expression of Fas peptides, or epitopic core regions, such as may be used to generate anti-Fas antibodies. In the nucleic acid vectors, the Fas antigen coding region may be positioned in a reverse orientation to that of the promoter, so that the promoter directs the expression of an antisense nucleic acid segment. Such antisense constructs are useful in hybridization.

Recombinant host cells that incorporate a nucleic acid segment, such as vector, that encode a Fas compound are another aspect of the invention. The cells may be prokaryotic host cells, such as E. coli; eukaryotic microbes, such as yeast cultures; or cells derived from the propagation of vertebrate cells in culture, e.g., VERO and HeLa cells, Chinese Hamster Ovary (CHO) cells and, preferably, COS cells.

This provides for further methods of the invention that include using the DNA segments disclosed herein. For example, to use a DNA segment in terms of recombinant expression, one would, generally, prepare a recombinant vector in which a Fas antigen coding region is positioned under the control of a promoter, and introduce the vector into a recombinant host cell. One would then culture the recombinant host cell under conditions effective to allow expression of the Fas antigen polypeptide, enabling the expressed, Fas antigen polypeptide to be collected. The expressed Fas antigen polypeptide may be purified by isolating away from total recombinant host cell components.

The fas gene and DNA segments may even be used in connection with somatic expression in an animal or in the creation of a transgenic animal. In such embodiments, the use of a recombinant vector that directs the expression of the complete Fas protein or the extracellular domain would be preferred.

In addition to their use in directing the expression of Fas proteins, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 10 to 14 nucleotide long contiguous sequence that has the same sequence as, or is complementary to, a 10 to 14 nucleotide long contiguous sequence that is complementary to SEQ ID NO: 3, SEQ ID NO:4, SEQ ID NO:5, SEQ ID NO:6 OR SEQ ID NO:7 will find particular utility. Longer contiguous identical or complementary sequences, e.g., those of about 20, 30, 40, 50, 100, 200, 500, 1000 (including all intermediate lengths) and even up to full length sequences of about 1336 nucleotides in length, will also be of use in certain embodiments.

The ability of such nucleic acid probes to specifically hybridize to Fas-encoding sequences will enable them to be of use in detecting the presence of genomic Fas sequences in a given sample. Also, the area immediately surrounding the structural gene for Fas may be characterized to further identify regulatory regions and other genes related to the regulation, production, and processing of Fas. Further uses envisioned include the use of the sequence information for the preparation of mutant species primers, or primers for use in preparing other genetic constructions.

Nucleic acid molecules having sequence regions consisting of contiguous nucleotide stretches of about 10 to 14, about 15 to 20, 30, 50, or even of about 100–200 nucleotides or so are particularly contemplated as hybridization probes for use in, e.g., Southern and Northern blotting. The total size of fragment, as well as the size of the complementary stretch(es), will ultimately depend on the intended use or application of the particular nucleic acid segment.

Nucleic acid segments or probes capable of detecting sequences at the 5' flanking region of the Fas gene, or Fas promoter region, will be those that include the novel sequences of the invention found to have homology with transcription factor binding sites identified in this region. It is expected that under certain readily-identifiable conditions, depending on the extent of additional transcription factor binding sites, these nucleic acid segments will exclusively bind to the transcription factor binding sites discovered by the inventors.

When using an appropriate fas probe, as described herein, the presence of a substantially complementary nucleic acid sequence in a sample, or a significantly increased level of such a sequence in comparison to the levels in a normal or "control" sample, will thus be indicative of a sample that contains a cell that harbors a Fas antigen. Here, substantially complementary Fas nucleic acid sequences are those that have contiguous sequences with relatively little sequence divergence and that are capable of hybridizing under relatively stringent conditions, as discussed above. As used herein, the term "increased levels" is used to describe a significant increase in the amount of the Fas nucleic acids detected in a given sample in comparison to that observed in a control sample, e.g., an equivalent sample from a normal healthy subject.

A variety of hybridization techniques and systems are known that can be used in connection with Fas detection and/or disease diagnosis aspects of the invention, including diagnostic assays such as those described in Falkow et al., U.S. Pat. No. 4,358,535.

In general, the "detection" of Fas sequences is accomplished by attaching or incorporating a detectable label into the nucleic acid segment used as a probe and "contacting" a sample with the labeled probe. In such processes, an effective amount of a nucleic acid segment that comprises a detectable label (a probe), is brought into direct juxtaposition with a composition containing target nucleic acids. Hybridized nucleic acid complexes may then be identified by detecting the presence of the label, for example, by detecting a radio, enzymatic, fluorescent, or even chemiluminescent label.

Many suitable variations of hybridization technology are available for use in the detection of nucleic acids, as will be known to those of skill in the art. These include, for example, in situ hybridization, Southern blotting and Northern blotting. In situ hybridization describes the techniques wherein the target or sample nucleic acids contacted with the probe sequences are located within one or more cells, such as cells within a clinical sample, or even cells grown in tissue culture. As is well known in the art, the cells are prepared for hybridization by fixation, e.g. chemical fixation, and placed in conditions that allow for the hybridization of a detectable probe with nucleic acids located within the fixed cell.

Alternatively, the sample nucleic acids may be separated from a cell within a clinical sample prior to contact with a probe. Any of the wide variety of methods for isolating target nucleic acids may be employed, such as cesium chloride gradient centrifugation, chromatography (e.g., ion, affinity, magnetic), phenol extraction and the like. Most often, the isolated nucleic acids will be separated, e.g., by size, using electrophoretic separation, followed by immobilization onto a solid matrix, prior to contact with the labelled probe. These prior separation techniques are frequently employed in the art and are generally encompassed by the terms "Southern blotting" and "Northern blotting". The use of Northern blotting, in which the sample nucleic acids are RNA, is particularly preferred with the present invention. The execution of various techniques using labeled probes to detect fas mRNA sequences and fas genomic sequences in clinical samples will be well known to those of skill in the art in light of the present disclosure.

Kits for use in molecular biological tests to identify Fas, and even to confirm the identity of individuals having, or being at risk for senescence of the immune system or aging-related disorders of the immune system, also fall within the scope of the present invention. Such kits will generally comprise, in suitable container means, one or more fas nucleic acid probes or primers, one or more unrelated nucleic acid probes or primers for use as controls, and optionally, one or more restriction enzymes or PCR components. The components of the kits will preferably be packaged within distinct containers. Fas nucleic acid probes capable of detecting fas transcripts may be provided as the central component of a Northern blotting kit.

In still further embodiments, the discoveries of the present invention are contemplated for use in designing new treatment strategies for autoimmune diseases. For example, drugs may be identified or designed to normalize transcription of genes important in tolerance induction and apoptosis, particularly the fas gene, but also other apoptosis genes known to those of skill in the art, and to restore normal gene function despite the presence of a mutation. Agents may also be identified or designed to normalize protein function, or protein levels, irrespective of ongoing abnormal gene function.

To treat an autoimmune disease or other disorder associated with aberrant apoptosis, it is contemplated that one would administer to a patient with such a disease or disorder an immunologically effective amount of a pharmaceutically acceptable composition capable of promoting or restoring normal apoptosis. To increase apoptosis from an inappropriately low level, as required to treat autoimmune diseases, malignancy or to combat aging, one may administer an agent, such as anti-Fas antibody, to eliminate excess Fas. To decrease apoptosis from an inappropriately high level, as required to treat strokes or heart attacks, one may administer an agent, including Fas itself, that results in raising the serum levels of Fas. All such methods are thus encompassed by the invention.

In other embodiments, the transcription factor binding regions may be used to promote Fas expression specifically in cells that would normally express Fas, but have a dysfunctional Fas due to a mutation in the coding region. The defective Fas could be replaced with a normal Fas gene and lead to Fas expression specifically in cells that would normally have Fas expression but not in other cells in which Fas expression and resultant apoptosis would be undesirable.

The Fas regulatory region will be useful fro development of drugs and inhibitors for modification of Fas expression that is up-regulated in a number of disease processes associated with up-regulation of Fas and apoptosis. This occurs after cerebral infarction where up-regulation of Fas leads to delayed apoptosis of neurons and further CNS tissue loss with poor recovery. In Sjogrens Syndrome, increased Fas expression on ductal epithelium is associated with continued inflammation and destruction of the salivary and lacrimal glands, leading to the characteristic dryness of these tissues. In rheumatoid arthritis, new Fas expression of synovial fibroblasts is associated with progressive synovitis and joint destruction. Thus, abnormally excessive Fas expression leads to excessive apoptosis and is found in a number of disease conditions where ongoing tissue damage leads to destruction of cells and loss of function.

Fas correction is important in autoimmune disease or T cell senescence with aging, and may be carried out using the transcription factor binding sites of the Fas promoter region in association with the normal extracellular Fas domain and the normal Fas intracellular domain. In addition, chimeric molecules composed of the normal Fas signalling intracellular domain ligated to the extracellular domain (such as the TNF-R extracellular domain) could be used to lead to Fas apoptosis by novel crosslinking molecules in patients where the Fas ligand is mutated or underproduced.

The Fas regulatory transcriptional factor binding sites could further be used to promote cell and tissue specific expression of a chimeric Fas molecule comprising a nonfunctional intracellular domain linked to a Fas ligand extracellular domain to inhibit Fas ligand binding to normal Fas and thus decrease apoptosis. Gene therapy with these chimeric constructs may be useful in correcting disease states in which excessive apoptosis is exhibited.

The invention embodies methods of expressing a recombinant DNA segment that includes an isolated Fas promoter region, comprising first preparing a recombinant vector in which a Fas promoter region is operatively linked to a DNA coding region that encodes a polypeptide or peptide. This recombinant vector is then introduced into a host cell, whereupon the recombinant host cell is maintained under conditions effective to allow expression of the coding region. In certain embodiments, the coding region encodes Fas, and in other embodiments, the coding region is a heterologous promoter.

Pharmaceutical Compositions

Compositions of the present invention will comprise an effective amount of the Fas promoter region and/or a recombinant vector that comprises the Fas promoter region dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. Other methods of delivering the compositions to target cells and tissues include the use of liposomes as carriers. In such embodiments, the vector is encapsulated within the liposome for delivery to the target tissue.

The invention further comprises a DNA segment that comprises the Fas promoter region operatively linked to a DNA coding region encoding a polypeptide or peptide, and means to deliver the composition into a mammalian cell for expression of a coding sequence. The coding sequence may be Fas, or it may be a heterologous coding sequence. Further to this embodiment is a method of regulating the expression of a polypeptide in a cell comprising operatively linking a Fas promoter region to an encoding region that encodes a polypeptide followed by expressing the polypeptide in the presence of at least one Fas gene transcription factor. The polypeptide may be Fas, or it may be expressed from a heterologous gene. In certain embodiments, the heterologous coding region codes for an enzyme that is capable of converting a non-toxic pro-drug into a cytotoxic drug.

Restoration of Immune Function

In other embodiments of the invention, it is contemplated that Fas expression may be restored in immune system cells that are lacking in such expression, or have such expression limited. It has been demonstrated that Fas expression and function are decreased in T cells of old mice. Age-related Fas dysfunction can be circumvented in CD2-fas transgenic mice. The presence of the CD2-fas transgene allows the maintenance of thymocyte numbers in aged mice comparable to that observed in young mice. Surprisingly, the syngenic-mixed lymphocyte response (SMLR and the response of peripheral T cells to stimulation by CD3 cross-linking is comparable to that of young animals. Moreover, an additional unexpected finding was that cytokine expression following CD3 stimulation was also comparable to levels observed in young mice.

As an example, a method of inhibiting senescence in immune system cells may comprise the steps of first preparing a genetic construct that comprises a Fas promoter region operatively linked to a Fas gene, followed by introducing the genetic construct into a host cell. The Fas gene is then expressed.

Fas expression may be altered in cells by preparing a genetic construct by first operatively linking a fas promoter region to a mutant fas gene, introducing the genetic construct into a host cell, followed by expressing the gene. Antisense fas genes or fragment of an antisense gene are contemplated to inhibit Fas expression in target tissues.

In important and further embodiments, a method is provided for determining the ability of a candidate substance to modulate the transcription of Fas specific genes, or heterologous genes operatively linked to a Fas promoter, which method comprises (a) providing a nucleic acid sequence containing the Fas transcription factor binding sites, a promoter and a reporter gene under the transcriptional control of both of the binding sites and the promoter which is capable of conferring a detectable signal on a host cell, (b) transfecting said nucleic acid sequence into a host cell to produce a cell culture of transgenic animal, (c) contacting the cell culture or transgenic animal with the candidate substance, and (d) detecting the signal produced by said cell culture or transgenic animal. The greater the signal the greater the activating character of the candidate, or, alternatively, the less the signal, the less the activating character of the candidate. Transcriptionally modulating candidate substances are then evaluated further for potential as, for example, pharmaceutical agents using conventional techniques and animal models. The reporter genes may be an enzyme, such as $\beta$-galactosidase or CAT. The signal from the reporter gene may be assayed in situ in the cell culture, or it may be assayed spectrophometrically outside of the culture dish.

In other embodiments, a method is provided wherein regions of the Fas promoter may be detected by first obtaining a candidate DNA segment suspected of having a Fas promoter region and then contacting the DNA with the DNA segment that comprises the Fas promoter region under stringent hybridization conditions, and then detecting hybridization.

Another even more surprising discovery of the invention is that Fas may prevent age-related T cell apoptosis in CD2-Fas transgenic mice. The inventors discovered that there is a marked decrease in the proliferation of T cells in old mice (26 month old) after anti-CD3 stimulation, compared to young mice (2 month old). Moreover, the old mice exhibited decreased Fas expression and ligand-induced apoptosis, but increased $CD44^+$. Anti-CD3 stimulated T cells from young mice exhibited increased production of IL-2 and decreased production of IFN-$\gamma$ and IL-10 compared to old mice. Thus, Fas function is decreased more than Fas expression in old mice.

The invention also provides methods of producing transgenic animals that express a polypeptide by positioning a Fas promoter sequence upstream from a selected expressible DNA coding region encoding the polypeptide, such that the expressible DNA coding region may be brought under the transcriptional control of the transcription factor binding site of the first DNA segment. This DNA segment is then introduced into a fertilized embryo, which is then implanted into the oviduct of a foster mother to produce a transgenic animal expressing the expressible DNA coding region. The expressible DNA coding region may comprise a Fas cDNA, or a heterologous gene. Exemplary structural genes include, but are not limited to a gene for a growth factor, growth factor receptor, cytokine, nuclear regulatory factor, tumor suppressor, anti-cancer agent or a peptide hormone. Further examples include the structural genes for TGF$\alpha$, TGF$\beta$, EGF, FGF, TNF$\alpha$, p53, c-myc, c-fos, GCSF, or GMCSF.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2-1 and 2-2. Sequence of the 5'-flanking region of human Fas gene (SEQ ID NO. 1). FIG. 2-1 shows the sequence prior to the most upstream transcription site. Transcription initiation sites determined by primer extension analysis are indicated by filled triangles. FIG. 2-2 continues the sequence from the most upstream transcription site which is designated as +1. The reported Fas 5'-end longest cDNA sequence derived from pF58 cDNA clone is indicated (Itoh et al., 1991). Sites of consensus transcription regulatory elements are underlined.

FIG. 7C. SMLR proliferative response in plates that had been pre-coated with anti-mouse Fas antibody (1.0 $\mu$g/ml).

FIG. 7D. Apoptosis of SMLR stimulated cells carried out on plates pre-coated with anti-mouse Fas (1.0 $\mu$g/ml).

DETAILED DESCRIPTION OF THE PREFERRED EMBODIMENTS

Figure 1:
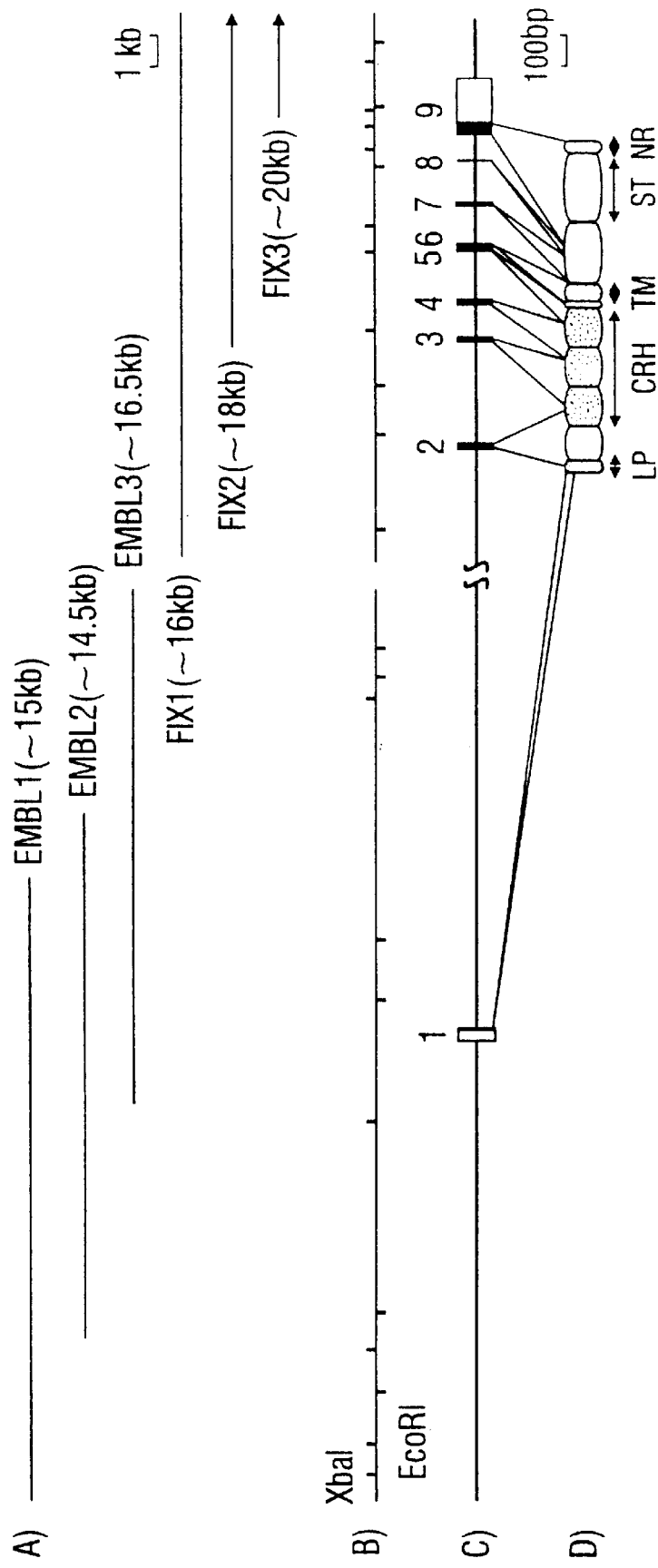
FIG. 1. Structure of the human Fas gene. This figure includes a schematic representation of six genomic DNA inserts containing the entire Fas cDNA, a restriction site map for Xba I and EcoR I used for analyzing the inserts and subcloning and the Exon/intron organization of the human Fas gene. Exons are represented by boxes and numbered in a 5'- to 3'- orientation. Coding sequences in the exons are shown by filled regions. Also represented is the relationship of the exon(s) to the domain structure of the human Fas molecule. LP, CRH, TM, ST, and NR indicate the leader peptide, the cysteine-rich homology region, the transmembrane domain, the apoptotic signal transduction domain, and the negative regulatory domain, respectively. All are drawn to scale as indicated.

Ligation of the Fas cell-surface molecule induces apoptosis. Defective Fas mediated apoptosis has been associated with spontaneous autoimmunity in mice. An important aspect of the present invention is the cloning and characterization of the human Fas chromosomal gene including the transcriptional control regions using human Fas/Apo-1 cDNA as a probe. The gene has 9 exons and spans more than 26 kb of DNA. The lengths of introns vary from >14 kb at the 5' end of the gene to 152 bp upstream of the exon encoding the transmembrane domain. The domain structure of the human Fas is encoded by an exon or a set of exons. Primer extension analysis revealed three major transcription initiation sites. The promoter region lacked a canonical "TATA" and "CAAT" boxes but was "GC-rich" sequence, and contained consensus sequence for AP-1, GF-1, NY-Y, CP-2, EBP20, and c-Myb. These data provide the first characterization of the human Fas gene including its regulatory region. This characterization will allow the use of the Fas promoter region to control and initiate expression of many useful genes, including but not limited to the Fas gene, Fas cDNA or any heterologous gene that is placed under the control of the promoter disclosed herein. It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

An important embodiment of the invention is related to the effects of aging on the mammalian immune system. The immunologic mechanism underlying defective Fas function with age is not known. One possibility is that there is an intrinsic age-related defect in transcriptional or post-transcriptional factors that regulate Fas expression. This view is supported by the fact that Fas is a member of a family of receptors containing cysteine repeat domains and includes TNF-R and CD40-L which also exhibit decreased expression with age (Song et al., 1993; Whisler et al., 1991; Whisler et al., 1991). Another possibility is that Fas signaling function might be impaired with aging which could further accentuate an expression defect. Fas signaling involves a phosphatase dependent pathway which is decreased with aging. The present discoveries will allow the development of novel intervention therapies to restore normal Fas signaling in the aged and the immunologically compromised.

The data disclosed herein indicate that Fas function is decreased more than Fas expression in old mice. One possibility is that high Fas expression is required for Fas-induced apoptosis. Enforced up-regulation of Fas in the CD2-fas transgenic mice allows the maintenance of Fas function and production of Fas-sensitive T cells in aged mice. This dissociation of Fas expression and function has also been observed in the thymus where all cells express intermediate to high levels of Fas, but only a minority of thymocytes are sensitive to Fas-induced apoptosis. Another possibility may be that alternatively spliced or non-functional forms of the Fas molecule might be present on T cells from aged mice, and that these forms can interact with the Fas antibody but do not signal apoptosis. Previous reports have indicated the presence of an alternatively spliced Fas molecule which results in the secretion of soluble Fas and inhibition of apoptosis (Cheng et al., 1994), and a mutation of Fas leading to defective apoptosis signaling in CBA/HeN-lpr/lpr mice (Watanabe-Fukunaga et al., 1992).

Previous results indicate that there are at least two pathways for apoptosis of thymocytes (Clarke et al., 1993; Lowe et al., 1993; Zacharchuk et al., 1991; Zacharchuk et al., 1991). Apoptosis of thymocytes that have undergone DNA damage by x-irradiation require p53 whereas steroid-induced apoptosis does not. In the Fas mutant lpr mice, there is an increase in steroid-induced apoptosis of thymocytes, but a decrease in Fas-induced apoptosis due to the Fas mutation (Van Houten and Budd, 1992). The present results also indicate that there is more than one pathway for apoptosis of T cells in the thymus and lymph node. One is active in young mice, whereas a second Fas-independent pathway is active for deletion of T cells from aged mice after stimulation. The shift from Fas dependent to Fas independent apoptosis with aging may account for altered phenotype and function of T cells with aging.

Loss of Fas function with age is associated with a decrease of the Th1 cytokine IL-2 and an increase of the Th2 cytokines IL-4 and IL-10. The overutilization of the Th2 pathway with aging has also been previously reported by other investigators (Karvin et al., 1992; Cillari et al., 1992). The present inventors have shown that T cells that have been stimulated to undergo preferential development as Th1 T cells express Fas and Fas ligand, whereas, T cells stimulated to undergo development as Th2 T cells do not express Fas or Fas ligand. The shift of Th1 to Th2 T cells with aging may be due to defective Fas-Fas ligand signaling. The restoration of preferential development of Th1 cells by the fas transgene in aged mice suggests that Fas interaction with its ligand has been corrected, and that Fas interaction may play a critical role in T cell development as well as T cell apoptosis with aging.

Immune system aging is associated with an increase in percentage of memory T cells characterized by expression of CD44 and CD45RO (Okumura et al., 1993; Howard et al., 1992; Thoman et al., 1993; Lerner et al., 1989; Ernst et al., 1990; Nagelkerken et al., 1991; Vitetta et al., 1991). In 26-month-old non-transgenic mice, approximately one-third of thymocytes and 50–60% of purified spleen T cells, increased CD44 expression was associated with low expression of cell surface Fas. Therefore, CD44[+] memory T cells would be insensitive to Fas-induced apoptosis. The percent of CD44[+] T cells was greatly reduced in CD2-fas transgenic aged mice. These results indicate that development of CD44[+] memory T cells in aged mice is related to several aspects of cell development including Fas expression. In both the spleen and thymus, there was also a small population of cells that express high Fas and also high CD44 indicating that other factors in addition to Fas expression influence CD44 expression.

Rescue of thymocytes from apoptosis by the provision of necessary signaling molecules or growth factors may be an important mechanism in the restoration of T cell function with aging. This is consistent with a number of reports that certain growth factors including GH from transplanted pituitary glands (Li et al., 1992) can prevent age-related thymic atrophy. Fas has been proposed to serve as a co-stimulatory molecule during thymic development of T cells (Ramsdell and Lynch, 1993), and the present data shows that decreased Fas expression and function with age leads to increased apoptosis of thymocytes. These results were unexpected since Fas was first identified as a molecule capable of inducing apoptosis in certain cells lines (Itoh et al., 1992; Yonehara et al., 1989). However, it is likely that Fas signaling leads to different responses depending on the cell type and stage of differentiation. In support of this, in Fas defective lpr/lpr mice, and Fas-ligand defective gld/gld mice, defective apoptosis of thymocytes has been difficult to detect (Zhou et al., 1993), and the primary defect in these mice is abnormal T cell differentiation and tolerance loss (Zhou et al., 1992; Zhou et al., 1991). Therefore, it is contemplated that defective intrathymic Fas signaling with age leads to a developmental defect and increase thymocyte apoptosis by a Fas-independent pathway. This Fas signaling defect plays a major role in development of thymic atrophy with aging.

Nucleic Acid Hybridization

The use of a Fas promoter hybridization probe of about 10–14 nucleotides in length allows the formation of a duplex molecule that is both stable and selective and is thus able to identify like nucleic acids, e.g., those located within cells that have Fas genomic sequences. Molecules having contiguous complementary sequences over stretches greater than 10 bases in length are generally preferred in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Hybridization probes may of course be selected from any portion of any of the sequences disclosed herein. All that is required is to review the sequence set forth and to select any continuous portion of the sequence, from about 10/14, or preferably about 14, nucleotides in length up to and including the full length sequence, that one wishes to utilize as a probe or primer. The choice of probe and primer sequences may be governed by various factors, such as, by way of example only, one may wish to employ primers encompassing consensus regulatory sequences; one may employ probes corresponding to the entire promoter DNA to clone Fas genes from other species or to clone further Fas-like or homologous genes from any species including human; and one may employ mutant probes or primers in site specific mutagenesis.

The process of selecting and preparing a nucleic acid segment that includes a contiguous sequence from the genomic sequence region may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of Fas cDNAs or mRNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02 M–0.15 M NaCl at temperatures of 50° C. to 70° C. Such selective conditions tolerate little, if any, mismatch between the probe and the template or target strand, and would be particularly suitable for isolating or identifying alternatively spliced mRNA.

Of course, for some applications, for example, where one desires to prepare mutants employing a mutant primer strand hybridized to an underlying template or where one seeks to isolate Fas-encoding sequences from related species, functional equivalents, or the like, less stringent hybridization conditions will typically be needed in order to allow formation of the heteroduplex. In these circumstances, one may desire to employ conditions such as 0.15 M–0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Site-Specific Mutagenesis

Site-specific mutagenesis is a technique useful in the preparation of mutant promoter regions useful in identifying important promoter elements. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the mismatch junction being traversed.

Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the Fas antigen. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the Fas promoter region using site-directed mutagenesis is provided as a means of producing potentially useful Fas species and is not meant to be limiting as there are other ways in which sequence variants of Fas may be obtained. For example, recombinant vectors encoding the desired Fas promoter may be treated with mutagenic agents to obtain sequence variants (see, e.g., a method described by Eichenlaub, 1979) for the mutagenesis of plasmid DNA using hydroxylamine.

Recombinant Host Cells

Suitable prokaryotic host cells for use with the present invention include *E. coli*. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, which contains genes for ampicillin and tetracycline resistance and thus provides easy means for identifying transformed cells.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform certain *E. coli* cells.

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-l. The presence of the trpl lesion as a characteristic of the yeast host cell genome then provides an effective environment for detecting transformation by growth in the absence of tryptophan.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication and possibly an identifiable marker gene. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. Also particularly useful in the present invention will be the use of viral vectors such as adenoviral or retroviral vectors with the Fas promoter inserted therein.

Pharmaceutical Compositions

As the Fas gene or other gene under control of the Fas promoter are contemplated for use in treating diseases connected with aberrant apoptosis, such agents may be formulated into pharmaceutically acceptable compositions for administration to a patient.

Aqueous compositions of the present invention will comprise an effective amount of the Fas promoter controlled gene, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. It also well known in the art that DNA preparations may be combined with liposomes or other delivery vehicles for introduction into cells. It is also known that the injection of naked DNA is an effective way of introducing foreign genes into an animal's cells. It is understood that any such method of administering the compositions of the present invention would be encompassed by the appended claims.

Screening Candidate Substances

In still further embodiments, the present invention concerns a method for identifying new Fas regulating compounds, which may be termed as "candidate substances." It is contemplated that this screening technique will prove useful in the general identification of any compound that will serve the purpose of inhibiting or activating Fas expression. It is further contemplated that useful compounds in this regard will in no way be limited to known transcriptional regulatory factors.

Accordingly, in screening assays to identify pharmaceutical agents which modulate Fas transcription, it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

The preferred candidate substance screening methods are based upon whole cell assays and preferably, employ a reporter gene that confers on its recombinant hosts a readily detectable phenotype that emerges only under conditions where transcription occurs directed by the Fas promoter. Generally, reporter genes encode a polypeptide not otherwise produced by the host cell which is detectable by analysis of the cell culture, e.g., by fluorometric, radioisotopic or spectrophotometric analysis of the cell culture. Exemplary enzymes include esterases, phosphatases, proteases (tissue plasminogen activator or urokinase) and other enzymes capable of being detected by their activity, as will be known to those skilled in the art. A preferred example is *E. coli* beta-galactosidase, which produces a color change upon cleavage of an indigogenic substrate. A more preferred example is the enzyme chloramphenical acetyltransferase (CAT) which may be employed with a radiolabelled substrate.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstance the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

The host cells used in the screening assay herein generally are mammalian cells. Cell lines should be relatively easy to grow in large scale culture. Also, they should contain as little native background as possible considering the nature of the reporter polypeptide. Examples include the Hep G2, VERO, HeLa, CHO, W138, BHK, COS-7, and MDCK cell lines. The Fas promoter-containing vector is cotransfected into the desired host, stable transformants selected and, optionally, the reporter gene and its controlling Fas promoter are amplified in order to increase the screening assay sensitivity. This is accomplished in conventional fashion by cotransforming the host with the reporter gene and a selectable marker gene such as DHFR (for DHFR minus host cells such as CHO) or DHFR and neo for other hosts, followed by the application of a selection agent.

The screening assay typically is conducted by growing the transformants to confluency in microtiter wells, adding serial molar proportions of candidate to a series of wells, and the signal level determined after an incubation period that is sufficient to demonstrate gene transcription in controls incubated in the absence of the candidate substance. The wells containing varying proportions of candidate are then evaluated for signal activation. Candidates that demonstrate dose related enhancement/repression of reporter gene transcription or expression are then selected for further evaluation as clinical therapeutic agents. Candidate compounds of either class might be useful therapeutic agents that would stimulate production of T cells or even effect apoptosis.

It should be understood that the screening method herein is useful notwithstanding that effective candidates may not be found, since it would be a practical utility to know that Fas activators do not exist. The invention consists of providing a method for screening for such candidates, not in finding them.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Isolation of Genomic Fas DNA

The following example describes the use of the Fas cDNA sequences as probes to isolate the human Fas encoding genomic DNA. The genomic clones included the exon and intron regions as well as the transcriptional control region. Cell culture and isolation of total cellular RNA. The human T cell lines, CEM-6 and Molt-4 (American Type Culture Collection, Rockville, Md.), were grown in RPMI-1640 supplemented with 10% FCS, 2 mM glutamine, 10 units penicillin/ml, and 10 mg streptomycin/ml. Total cellular RNA was isolated from the cells using the guanidine isothiocyanate/acid phenol method (Chomcynski and Sacchi, 1987, incorporated herein by reference).

Preparation of the human Fas cDNA probes. A human Fas cDNA probe was amplified by the reverse transcriptase-polymerase chain reaction method as described (Cheng et al., 1994, incorporated herein by reference) using the first-strand cDNA generated from CEM-6 cellular RNA as a template and two oligonucleotides, 5'-AAGCGGTTTACGAGTGACT-3', (nt 23–40) (SEQ ID NO. 9) and 5'-TGGTTCCAGGTATCTGCTTC-3', (complementary to nt 2422–2441) (SEQ ID NO. 10) (Itoh et al., 1991). The PCR products corresponding to Fas nt 23–2441 were recovered from an 0.8% low-temperature melting agarose gel (NuSieve GTG agarose, MFC Corp.) and directly subcloned into a pCR™ vector (Invitrogen, San Diego, Calif.) following the procedures recommended by the supplier. The probes used in these analyses included fragments of the human Fas CDNA corresponding to nt 23–2441 excised by using EcoR I single digestion and to nt 23–346 excised by using EcoR I/Stu I double digestion from the Fas-pCR™ recombinant, respectively. The probes were labeled using the random hexanucleotide priming method (Feinberg and Vogelstein, 1984, incorporated herein by reference) and [a-$^{32}$P]-dCTP (Amersham Corp., Arlington Heights, Ill.).

Isolation of Fas genomic clones. Two human placental genomic DNA libraries constructed in the Lambda FIX™II vector (Stratagene Inc., La Jolla, Calif.) and in the EMBL-SP6/T7 vector (Clontech, Palo Alto, Calif.) were screened by plaque hybridization under high stringency conditions (Sambrook et al., 1989). Three bacteriophage clones, designated FIX1, FIX2 and FIX3, were identified from ~10$^6$ plaques of the library in the lambda FIX™II vector using the $^{32}$P-labeled segment of the human Fas cDNA corresponding to nt 23–2441 (Itoh et al., 1991). An additional three positive bacteriophage clones, designated EMBL1, EMBL2 and EMBL3, were identified from ~10$^6$ plaques of the second library in lambda EMBL-SP6/T7 vector using the $^{32}$P-labeled Fas cDNA fragment corresponding to nt 23–346. The positive recombinant phage plaques were isolated after two subscreenings and the DNA was prepared using Wizard Lambda Preps Kit (Promega Corp., Madison, Wis.) following the procedure recommended by the supplier. To map the cloned DNA fragments, partial digestion and Southern blot analysis were performed (Sambrook et al., 1989). The inserts were excised using Not I when in the Lambda FIX™II vector or Sfi I when in the EMBL-SP6/T7 vector, separated from the vector arms by agarose gel electrophoresis, and recovered from the gel slices. The insert was then partially digested with EcoR I or Xba I, and electrophoresed in agarose gel. The DNA in the gel was blotted onto nitrocellulose (Schleicher & Schuell, Inc., Keene, N.H.), developed with [γ-$^{32}$P]ATP (Amersham Corp., Arlington Heights, Ill.) labeled T3, T7 and/or SP6 primer, respectively, and autoradiographed at −70° C. for 1 day. The exons were localized by Southern hybridization of the blot prepared from each digestion of 2 μg λ rDNA and developed with the [a-$^{32}$P]-labeled human Fas cDNA probes.

DNA sequence analysis. The exon containing DNA fragments were prepared from the cloned inserts using EcoR I and/or Xba I and subcloned into the pBluescript vector (Strategene Inc.). The recombinant plasmids were purified using QIAGEN 100-tips (QIAGEN, Inc., Studio, Calif.) according to the procedure recommended by the supplier. Templates for nucleotide (nt) sequencing were alkali-denatured recombinant plasmids. All nt sequences were determined by the dideoxy chain termination method using modified bacteriophage T7 DNA polymerase (United States Biochemical Corp., Cleveland, Ohio) (Tabor and Richardson, 1987). Primers used for sequencing were T3, T7, SP6, and oligonucleotides derived from the human Fas CDNA sequence or from genomic sequence as they became available. Oligonucleotides were synthesized at the Oligonucleotide Synthesis Core Facility in the UAB Comprehensive Cancer Center. Sequences were obtained for both strands of all DNA segments containing exons and exon-intron boundaries of at least 100 bp[4]. Nt sequencing data were analyzed by using the Sequence Analysis Software Package of the University of Wisconsin Genetics Computer Group (Madison, Wis.). Intron lengths were determined by either complete nt sequencing or PCR using primer sets derived from sequences of adjacent exons. Further confirmation was obtained by comparison of Southern blots prepared from the cloned genomic DNA fragments to that prepared from the human genomic DNA to exclude deletions and or rearrangements in the cloned fragments.

Primer extension analysis. Primer extension analysis was performed essentially as described (Sambrook et al., 1989). Briefly, a 21-mer synthetic oligonucleotide primer (5'-CTCAGGGTGTGTTCCGTGCCA-3', complementary to nt 66–86) (SEQ ID NO.11) (Itoh et al., 1991) was labeled at its 5'-end using T4 polynucleotide kinase (Boehringer Mannheim Corp., Indianapolis, Ind.) and [γ-$^{32}$P] ATP (Amersham). Labeled primer (2×10$^5$ cpm) was co-precipitated with 50 mg total cellular RNA and then resuspended in 20 ml of hybridization buffer containing 80% formamide, 0.4 M NaCl, 40 mM PIPES (pH 7.0), 1 mM EDTA (pH 8.0). The mixture was initially incubated at 90° C. for 5 min and then at 42° C. overnight. The mixture was precipitated and resuspended in 20 ml of reaction buffer containing 50 mM Tris-HCl (pH 7.5), 60 mM KCl, 10 mM DTT, 1 mM each dNTP, 1,000 unit/ml RNA inhibitor (Boehringer), and 50 units of AMV reverse transcriptase (Boehringer). The primer extension reaction was carried out at 42° C. for 2 hr. The RNA was digested with DNAase free-pancreatic ribonuclease A (Boehringer) and samples were applied to a sequencing gel in parallel with a sequence reaction of the Fas 5'-flanking genomic DNA annealed with the same primer.

EXAMPLE 2

Structure of the Human Fas Gene

Three positive clones were isolated from a human placental genomic library using the $^{32}$P-labeled segment of the human Fas cDNA corresponding to nt 23–2441 (Itoh et al., 1991) as described in Example 1. Inserts of these clones were analyzed by restriction mapping and Southern blot analysis. Results obtained indicated that these inserts overlapped and contained most of the human Fas cDNA sequence except for the 5'-untranslated region and sequences coding for the N-terminal part of the signal peptide (FIG. 1). To obtain the missing regions of the Fas gene, the second human placental genomic library was screened using the $^{32}$P-labeled segment of the human Fas cDNA corresponding to nt 23–346. An additional three positive bacteriophage clones were isolated and characterized as described above. Comparison of the established restriction map indicated that inserts of these clones contained the missing 5'-portion sequence and overlapped each other. Therefore, segments of human chromosomal DNA containing the entire human Fas cDNA were isolated (FIG. 1).

To define the structure of the human Fas gene, the appropriate restriction fragments containing exon(s) were subcloned and the exon and its surrounding intron nt were sequenced, respectively. When the human Fas genomic sequence was aligned with the human Fas cDNA sequence (Itoh et al., 1991; Oehm et al., 1992), both sequences matched completely. This confirms the cloned Fas cDNA sequence and reveals the exon/intron organization of the human Fas gene (FIG. 1). The gene comprises 9 exons and spans >26 kb of DNA. Table I indicates the length of the exons and introns and the nt sequences surrounding exon/intron boundaries. Introns vary in length from 152 bp upstream of the exon encoding the transmembrane domain to >14 kb for the most 5' intron; while exons vary in length from 25 bp to 1664 bp. All exon/intron junctions follow the consensus rule of the splice acceptor-AG/GT-splice donor for splicing (Mount, 1982; Shapiro and Senapathy, 1987).

The first exon is separated from exon 2 by >14 kb and consists of the entire 5'-untranslated region of the human Fas cDNA and a 30 bp translated segment which encodes the first 10 amino acids of the putative 16 residue leader peptide of the Fas molecule. The Fas extracellular domain contains three cysteine-rich motif repeats encoded by a set of exons 2–5. The exon/intron structure does not reflect the repeat borders (FIG. 1). This is also the case for the human NGF receptor (Sahgal et al., 1988), TNF receptor 1 (Fuchs et al., 1992), and CD27 (Loenen et al., 1992), which are members of the NGF/TNF receptor superfamily with known gene structure.

The transmembrane domain of the human Fas gene consists of a 17 amino acid hydrophobic segment encoded by exon 6 and the first 2 bp of exon 7. A Fas mRNA transcript variant that is the result of splicing out of exon 6 has been described elsewhere (Cheng et al., 1994). The alternatively spliced mRNA encodes a human Fas molecule which lacks the transmembrane domain and is present as a soluble, secreted form. Elevated levels of soluble Fas observed in some patients with SLE may block apoptosis resulting in accumulation of self-reactive T- and B-cells, and perhaps accounting for the presence of increased mutations observed in the lymphocytes of SLE patients (Gmelig-Meyling et al., 1992).

The remaining 81 bp in exon 7 and the 25 bp in exon 8 are the two smallest exons of the Fas gene, encoding 27 and 8 amino acids, respectively, of the membrane proximal portion of the cytoplasmic region. This region has no homology to proteins in the databases, appears to be unique to the Fas molecule, and is in close proximity to a previously reported Fas signal-transducing domain of 68 amino acids corresponding to residues 231–298 of human Fas molecule (Itoh and Nagata, 1993). This unique region of Fas is contemplated to be important in the delivery of distinct intracellular signals associated with Fas function.

Apoptotic signal transduction through the human Fas molecule is mediated by a segment at its carboxyl terminal which exhibits high homology with that of the human TNF receptor 1 (Itoh et al., 1991; Itoh and Nagata, 1993). This functional domain is entirely contained within the last and largest exon of the human Fas gene and the corresponding exon of the human TNF receptor 1 (Fuchs et al., 1992), indicating that they most likely share a common ancestral exon. Human Fas exon 9 consists of 1664 bp and includes 329 bp translated region, a TAG termination codon and the entire 1332 bp 3'-untranslated region. It also includes three ATTAAA potential polyadenylation signaling sites. The ATTAAA segment deviates from the canonical AATAAA signal for poly A attachment, found in 12% of vertebrate genes (Wichens and Stephenson, 1984), and has been shown to be functional in vitro (Sheets et al., 1990).

Figure 3:
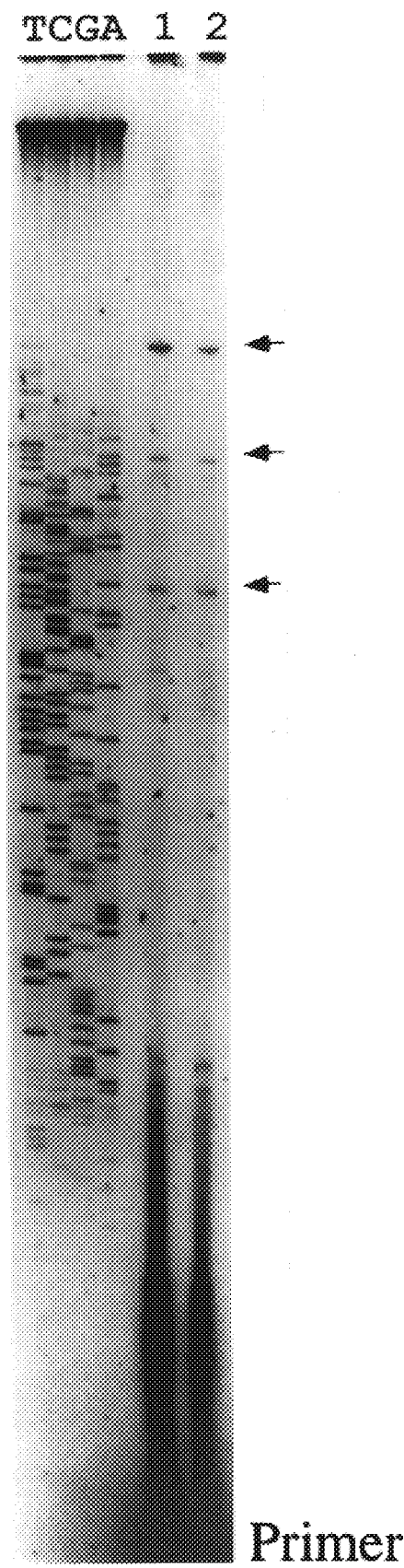
FIG. 3. Analysis of human Fas transcription initiation site by primer extension. A $^{32}$P-labeled 21-mer oligonucleotide was annealed with total cellular RNA derived from the human T cell lines CEM-6 (lane 1) and Molt-4 (lane 2), and extended using AMV reverse transcriptase. The extended cDNA products were analyzed by a sequencing gel along with a Fas 5'-flanking genomic DNA sequencing ladder extended with the same primer. Three major transcription initiation sites are indicated on right by arrowheads.

A region of about 1270 bp upstream of the exon 1 of Fas gene was determined as shown in FIG. 2. To determine transcription initiation site(s), primer extension analysis was performed. The mRNA isolated from human T cell lines CEM-6 or Molt-4 were used in this study because they express high levels of Fas. The analysis revealed three major bands which correspond to a T residue, designated as position +1, an A residue at position 74 and a T residue at position 126, respectively (FIG. 3).

To identify potential regulatory elements in the promoter region, a computer search was performed to compare the genomic DNA sequence upstream of the determined transcription site with known consensus sequences. The analysis revealed that there are no consensus "TATA" and "CAAT" boxes at the appropriate positions, but a "GC-rich" sequence was found around positions −53 to −84 (FIG. 2). This characteristic is consistent with the observation of multiple human Fas transcription initiation sites determined by the primer extension analysis. In addition, the consensus for several transcription factor binding sites were identified in the promoter region. They are AP-1 (TGANT$^C/_A$A) (SEQ ID No.3) (Jones et al., 1988) at position −451 to −449, CP2 protein (AGCCACT) (SEQ ID No.4) (Chodosh et al., 1988) at position −38 to −32, GF-1 (CTATCA) (SEQ ID No.5) (Tsai et al., 1989) at position −554 to −549 and −928 to −923, NF-Y (ATTGG) (SEQ ID No.6) (Dorn et al., 1987) at position −471 to −467 and −726 to −722, Myb (SEQ ID No.7) (Biedenkapp et al., 1988) at position −803 to −798, and EBP20 (GTGG$^A/_T$$^A/_T$G) (SEQ ID No.8) (Johnson et al., 1987) at position −908 to −890.

The presence of an AP-1 binding site is consistent with the observation that Fas expression is elevated after T cells are activated by PHA-P (Mysler et al., 1994). Myb has been shown to be involved in the G1/S transition in antigen stimulated normal human T cells (Gewirtz et al., 1989), and is increased after induction of cell death upon removal of IL-2 from an IL-2 dependent cell line (Seldin et al., 1989). This is seen in the CD4-CD8-B220+ T cells from Fas defective MRL-lpr/lpr mice and Fas ligand defective C3H-gld/gld mice (Mountz and Steinberg, 1989; Mountz et al., 1984). This is the first molecular connection between increased c-Myb expression in Fas or Fas ligand mutant mice and the structure of the Fas gene. In addition, activated T cells increase expression of c-myb mRNA (Gewirtz et al., 1989; Reed et al., 1986) as well as Fas mRNA (Mysler et al., 1994).

EXAMPLE 3

Fas Expression in Transgenic Mice

This example demonstrates that Fas expression and function are decreased in T cells of old mice. This example also demonstrates that the age-related Fas dysfunction can be circumvented in CD2-fas transgenic mice. The presence of the CD2-fas transgene allows the maintenance of thymocyte numbers in aged mice comparable to that observed in young mice. The syngeneic-mixed lymphocyte response (SMLR) and the response of peripheral T cells to stimulation by CD3 cross-linking is comparable to that of young animals. Cytokine expression after stimulation was also comparable to levels observed in young mice.

Mice. CD1 mice were obtained from Charles River (Wilmington, Mass.) and kept in specific pathogen-free conditions.

Production of CD2-fas Transgenic CD1 Mice. CD1 mice were used for superovulation and production of the CD2-fas transgenic mice as previously described (Wu et al., 1993, incorporated herein by reference). Single-cell MRL-lpr/lpr embryos were produced, injected with ~100 copies of the CD2-Fas transgene, and then place into the distant oviduct of CD1 pseudopregnant female mice. Tail DNA prepared from offspring was digested with EcoRI and probed with a $^{32}$P-labeled full-length Fas cDNA to identify CD2-Fas transgenic mice The CD2-fas construct was made by ligation of a full-length murine fas cDNA into an EcoRI site in front of exon 1 of a human CD2 minigene consisting of 5.5 kb of the 5' flanking sequence, exon 1, the first intron, fused exons 2 to 5 and 2.1 kb of the 3' flanking sequence. The 3' sequence of this CD2 minigene has been shown to be sufficient to allow copy-dependent, integration-independent expression primarily in $CD2^+$ T cells in transgenic mice (Greaves et al., 1989; Lang et al., 1988). Transgenic mice were identified by tail DNA analysis and housed with littermate controls for 24 months while being maintained on food and water, ad libitum. The young 2-month-old CD1 mice used in the experiments were derived from a breeding colony of CD1 mice.

Southern Blot Analysis. Tail DNA was prepared and digested with the indicated restriction enzymes. Approximately 10 $\mu$g of the digested DNA was separated on a 0.7% agarose gel, blotted to a nylon membrane and hybridized with a $^{32}$P-labelled full-length fas cDNA probe extending from 49 to 1033 bp of the murine sequence as previously described (Wu et al., 1993).

Expression of Murine Fas Ligand. The murine Fas ligand was cloned and sequenced using PCR primers prepared according to the sequence of the known mouse Fas ligand (Suda et al., 1993; Takahashi et al., 1994). The full length murine Fas ligand cDNA was cloned into the pcDNA1 expression vector (Invitrogen, San Diego, Calif.). 20 $\mu$g of purified plasmid DNA was precipitated with 500 $\mu$g/ml of DEAE-Dextran (Sigma, St. Louis, Mo.) and added to $5 \times 10^6$ of COS7 cells in a 10 cm cell culture dish containing 10 ml of serum-free RPMI 1640 and 10 mM chloroquine (Sigma, St. Louis, Mo.), and incubated at 37° C. for 4 hours. The transfected cells were then treated with 10% DMSO+RPMI-1640 for 2 minutes, and grown in 12% FCS RPMI-1640 for 72 hours. The supernatant was collected and then stored at −20° C. until use.

Preparation of Murine Fas-Human IgG1 Fusion Protein. A murine Fas-human IgG1 (fas-hIg) fusion protein was prepared as previously described (Cheng et al., 1994). Briefly, the extracellular domain of the mouse fas cDNA was fused with the Fc portion of human IgGl gene to form an open reading frame. The fusion gene was cloned into the pcDNAl eukaryotic expression vector (Invitrogen) and transfected into COS7 cells as described above. The fusion protein was purified on an anti-human IgG agarose column (Sigma, St. Louis, Mo.) and concentrated to 1 mg/ml in PBS.

T Cell Enrichment. Single cell suspensions of lymphocytes or spleen cells were enriched using a T cell enrichment column (R & D System) according to the directions of the manufacturer. Purified T cell populations were >98% T cells as determined by flow cytometry analysis of CD3 expression.

Flow Cytometry Analysis. Anti-CD3 (clone: 145.2C11), anti-CD4 (clone: GK 1.5), anti-CD8 (clone: 53-47) and anti-CD44 (clone: 1M7), and anti-mouse Fas (clone: Jo2) were purchased from Pharmingen (San Diego, Calif.). Single cell suspensions of lymphocytes, spleen cells or thymocytes ($10^6$/sample) were stained in FACS buffer (PBS with 5% fetal calf serum and 0.1% sodium azide) and optimal concentrations of antibodies. For two and three color analysis, cells were labeled with optimal concentrations of FITC conjugated anti-CD4 and PE conjugated anti-CD8 or biotin conjugated anti-Fas or anti-CD44. Biotinylated conjugated antibodies were revealed by Tandem-avidin. Viable cells were determined by forward and side light scatter using standard methods and were less than 6% of the sample size. Viable cells (10,000 per sample) were analyzed by flow cytometry on a FACS-Scan (Becton-Dickinson, Mt. View, Calif.) with logarithmic scales.

Stimulation by SMLR or Anti-CD3. Anti-CD3 (clone 145.2C11) mAb was diluted to 1 $\mu$g/ml and coated on flat bottom 96 well plates (Costar, Cambridge, Mass.) by incubation for 12 hours at 4° C. The plates were thoroughly washed using sterile PBS and enriched T cells were added in duplicate cultures for 72 hours. For syngeneic mixed lymphocyte reaction (SMLR) proliferative responses, $10^6$ enriched T cells were cultured in 200 $\mu$l of RPMI supplemented with 10% fetal calf serum. For some experiments the SMLR was carried out in the presence of the Fas fusion protein (0.1 $\mu$g/ml) or plate bound anti-mouse Fas monoclonal antibody (1.0 $\mu$g/ml). Proliferation was measured by the incorporation of $^3$H-thymidine (Amersham).

Assay of Cytokines. Cytokines were assayed using ELISA kits according to the manufacturer's instructions (Genzyme Corp., Cambridge, Mass.). The $OD_{405}$ was measured on an Emax microplate reader (Molecular Devices). Duplicate samples were assayed in 3 separate experiments and the mean determined. The statistical significance was determined using the Wilcoxon sign-rank nonparametric test.

In situ Nick Translation Apoptosis Staining. Nuclear DNA fragmentation was carried out as previously described (Gavrieli et al., 1992, incorporated herein by reference). For cell suspensions, $1 \times 10^5$ cells were cytospun onto poly-L-lysine (Sigma, St. Louis, Mo.) pre-coated slides. The slides were fixed for 30 minutes in 10% formalin-PBS buffer and then washed with $H_2O$ for 2 minutes, 6 times. Fresh proteinase K (20 $\mu$g/ml, Boehringer, Indianapolis, Ind.) was added onto the slides and incubated at RT for 15 minutes. After washing with $H_2O$, terminal deoxynucleotide transferase (1 $\mu$/ml) (Boehringer Mannheim) and digitonigen-modified dUTP (Boehringer Mannheim) 0.15 $\mu$l/ml was added in TdT buffer. A cover glass was applied and the slides incubated for 1 hour at 37° C. in a humidified chamber. After removing the cover glass, the slide was washed once with PBS followed by incubation in 5% BSA/FACS buffer for 15 minutes at RT. The slides were incubated with an anti-digoxigenin antibody conjugated to alkaline phosphatase (Boehringer, Indianapolis, Ind.) at 1:50 dilution with FACS buffer for 30 minutes at RT. After washing 6 times in PBS the slides were incubated in alkaline phosphatase buffer with BCIP/NTB (Sigma, St. Louis, Mo.) and incubated for 30 minutes at RT.

Figure 4:
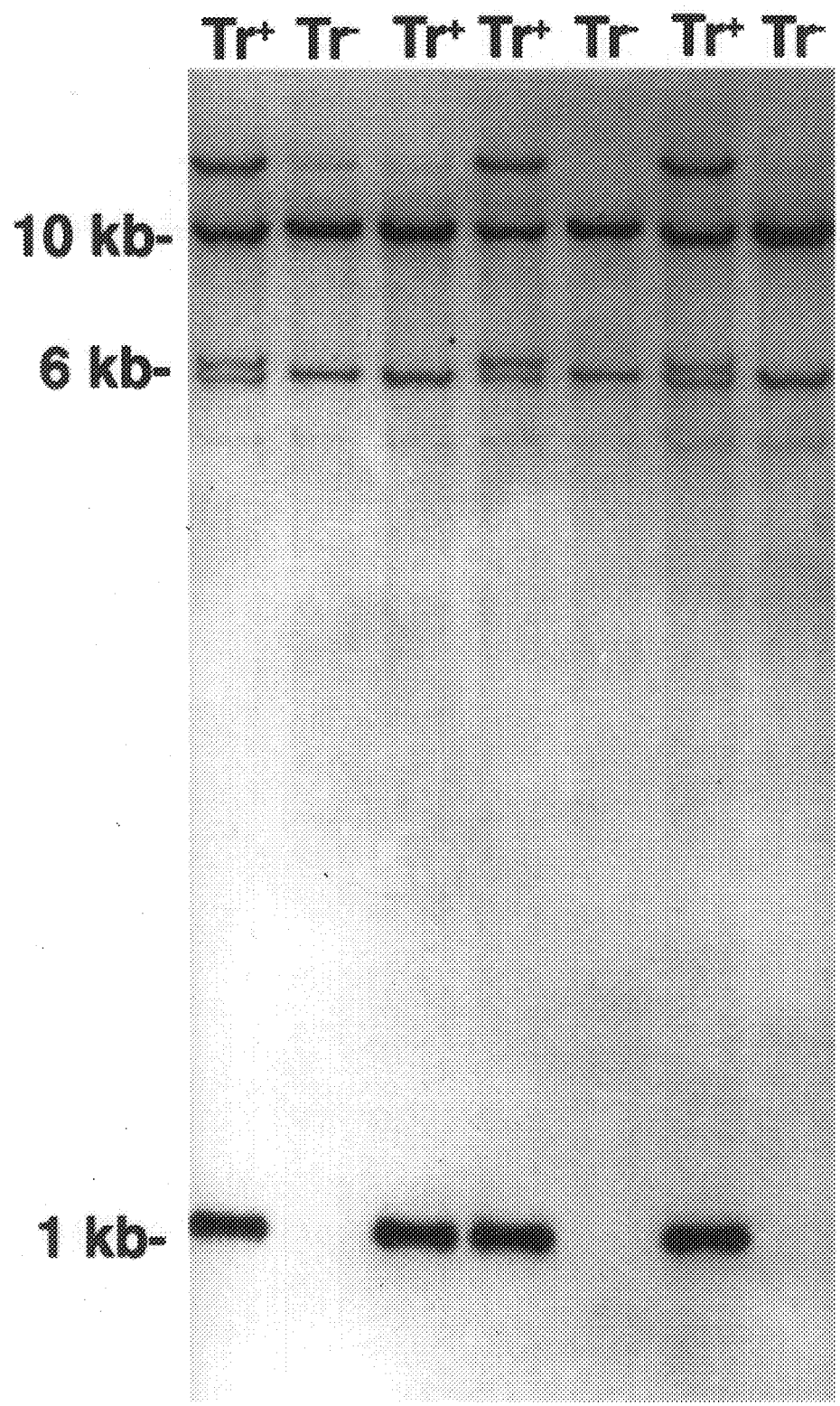
FIG. 4. Analysis of CD2-fas Transgenic CD1 Mice by Southern Blot Analysis. Tail DNA was digested with the EcoRI restriction enzyme which releases the 1.1 kb fas cDNA insert from the CD2-fas transgenic mice.
Figure 5A:
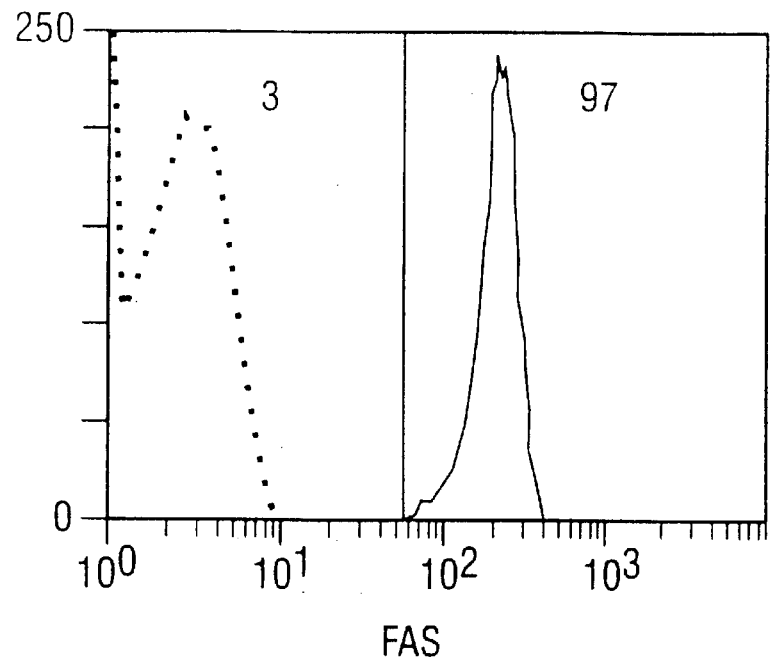
FIGS. 5A–F. Expression of Fas on Thymocytes and Spleen Cells. Single cell suspensions of thymocytes and spleen cells from 2-month-old, 26-month-old, and 26-month-old Fas transgenic mice ($10^6$/sample) were stained with anti-Fas. The histograms of Fas expression are representative of at least 10 mice from each group. The gates used to define lymphocyte populations are indicated by the vertical lines. Negative control staining is shown as the dotted curves. Viable cells (10,000 per sample) were analyzed by flow cytometry on a FACS-Scan with logarithmic scales.
Figure 5B:
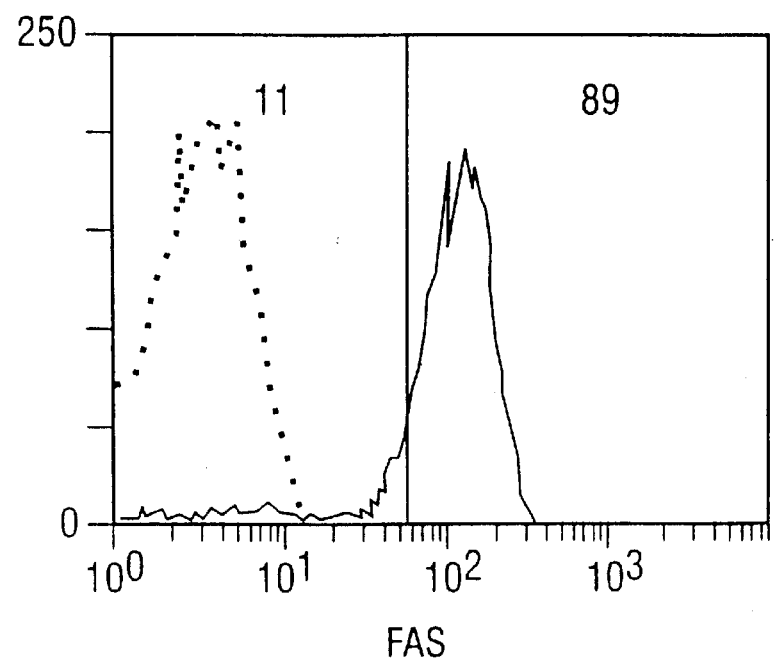
Figure 5C:
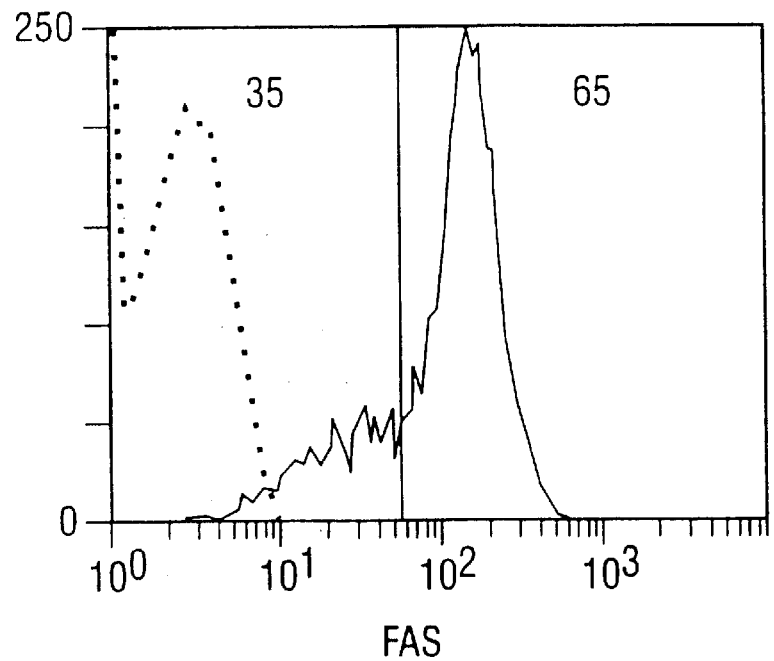
Figure 5D:
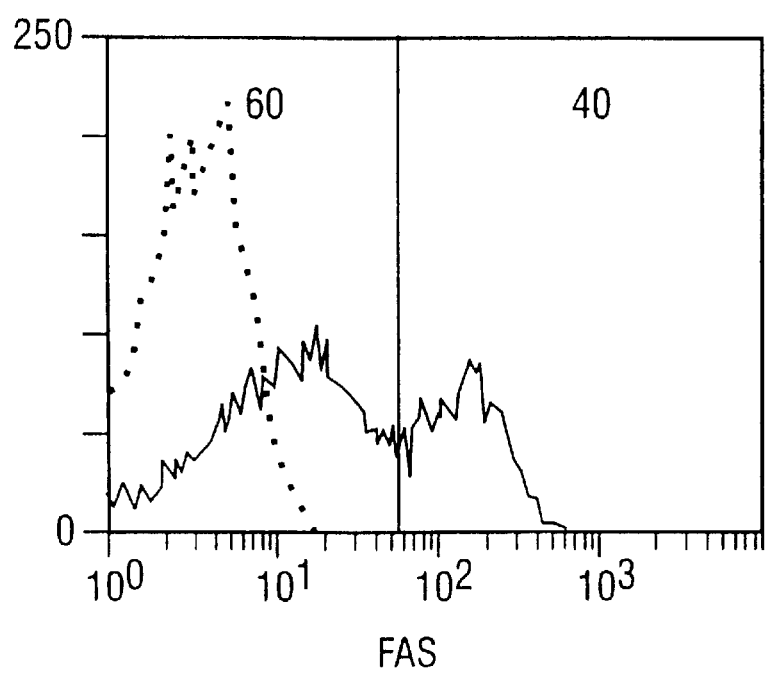
Figure 5E:
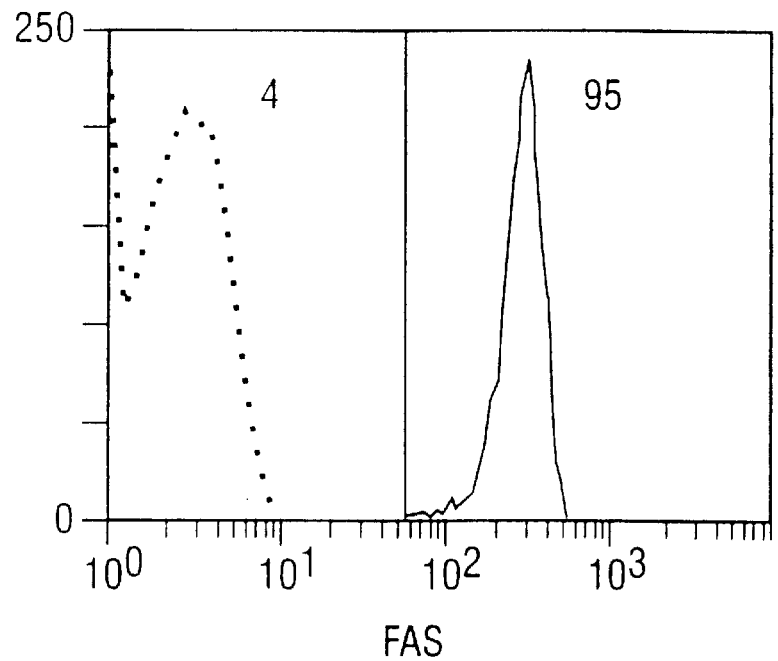
Figure 5F:
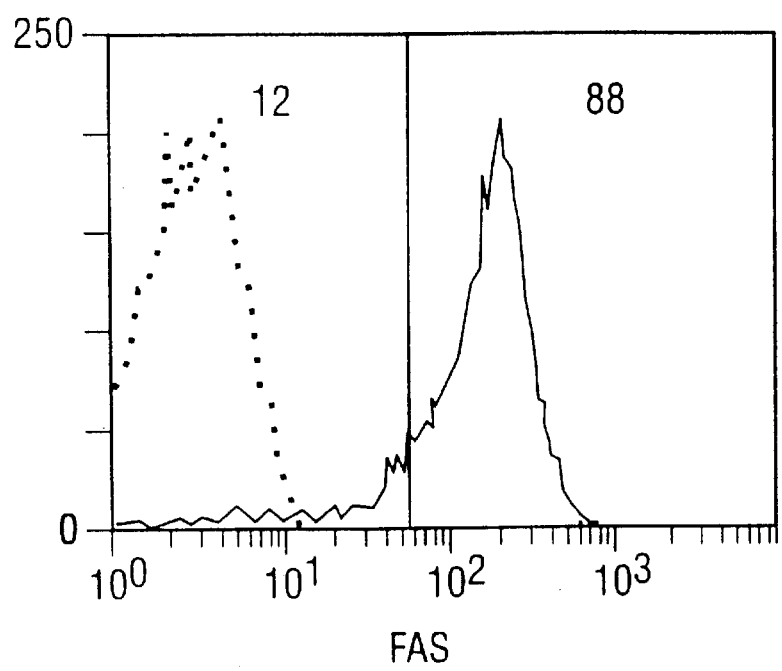

CD2-fas Transgenic Mice. Tail DNA was prepared from mice at 4 weeks of age, digested with EcoRI restriction enzyme and hybridized with the full-length mouse Fas cDNA probe. One of the four founder CD1 CD2-fas transgenic mice was identified as having a single 1.1 kb transgenic Fas cDNA integration band (FIG. 4, lane 3) and therefore mated with CD1 breeder mice. Transgenic and non-transgenic offspring of this mating were studied at 22–26 months of age.

Figure 6:
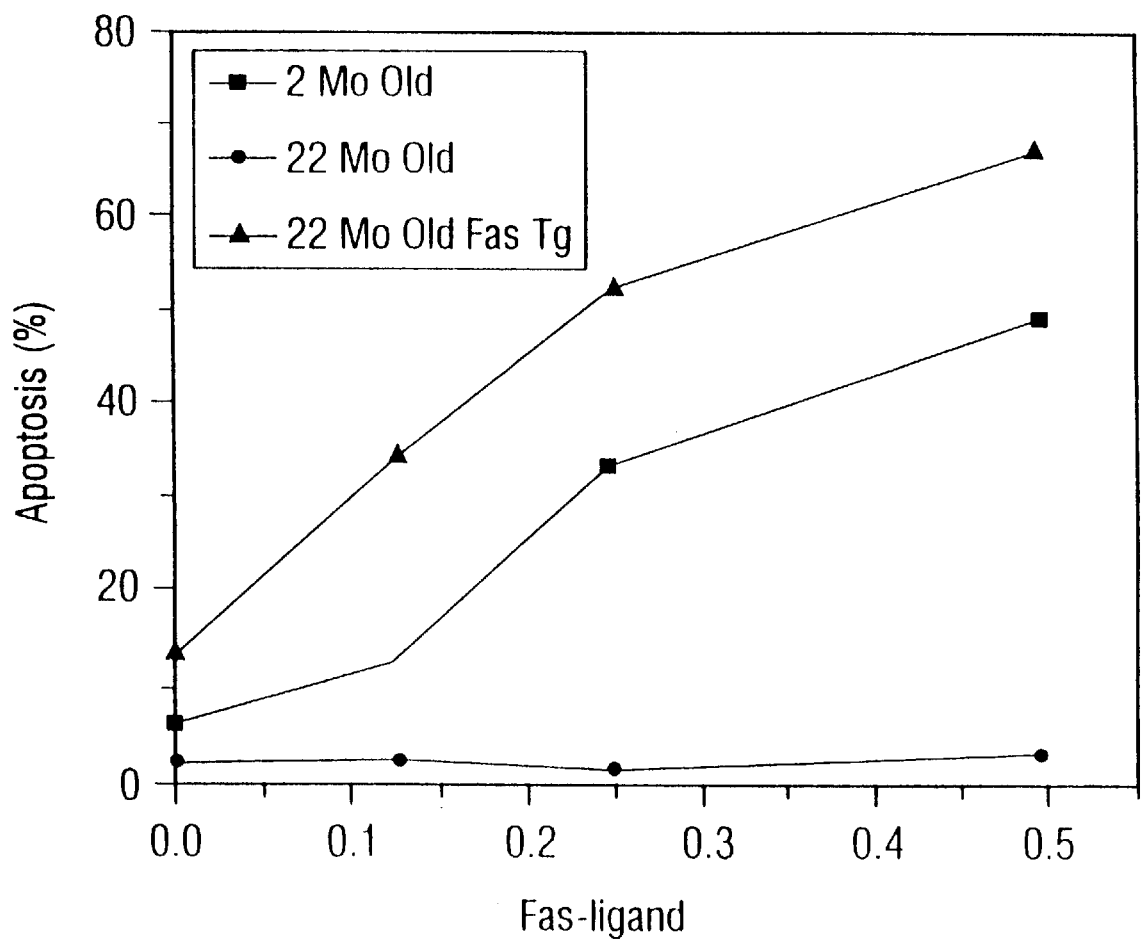
FIG. 6. Correction of Fas-Ligand Induced Apoptosis in CD2-Fas Transgenic Aged Mice. Lymphocyte suspensions ($10^6$/sample) were cultured for 18 hr with different dilutions of supernatant of COS7 cells expressing the Fas Ligand ranging from 0 to 0.5 (50/50:V/V). Lymphocytes were obtained from 2-month (square), 22-month (circle) or 22-month-old CD2-Fas transgenic mice (triangle). Apoptosis was determined by the in situ nick translation assay of single cell suspensions of lymphocytes as previously described (Vitetta et al., 1991). The results represent the mean +/– SEM for three separate mice assayed individually in triplicate culture wells.

Fas Expression and Function on Lymphocytes. Cell surface Fas expression was decreased on lymphocytes from 26-month-old non-transgenic CD1 mice compared to 2-month-old non-transgenic mice (FIG. 5). Fas expression was increased to youthful levels in 26-month-old CD1 CD2-fas transgenic mice. Fas ligand induced apoptosis was markedly decreased in lymph node cells from aged mice, and development of this apoptosis defect was prevented in CD2-fas transgenic aged mice (FIG. 6).

Figure 7B:
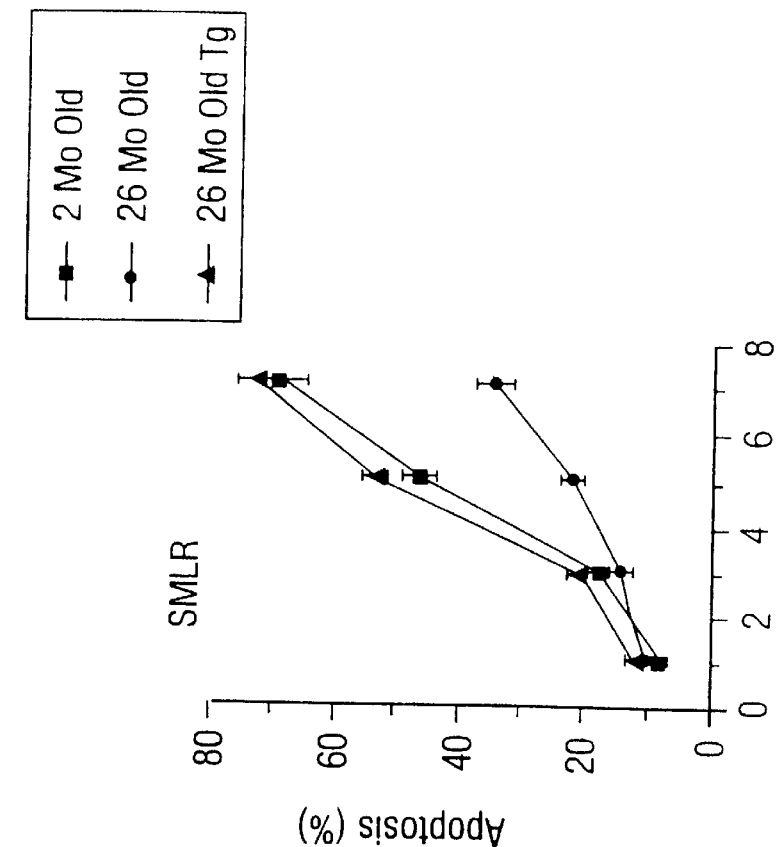
FIG. 7B. Apoptosis of SMLR stimulated cells.
Figure 7A:
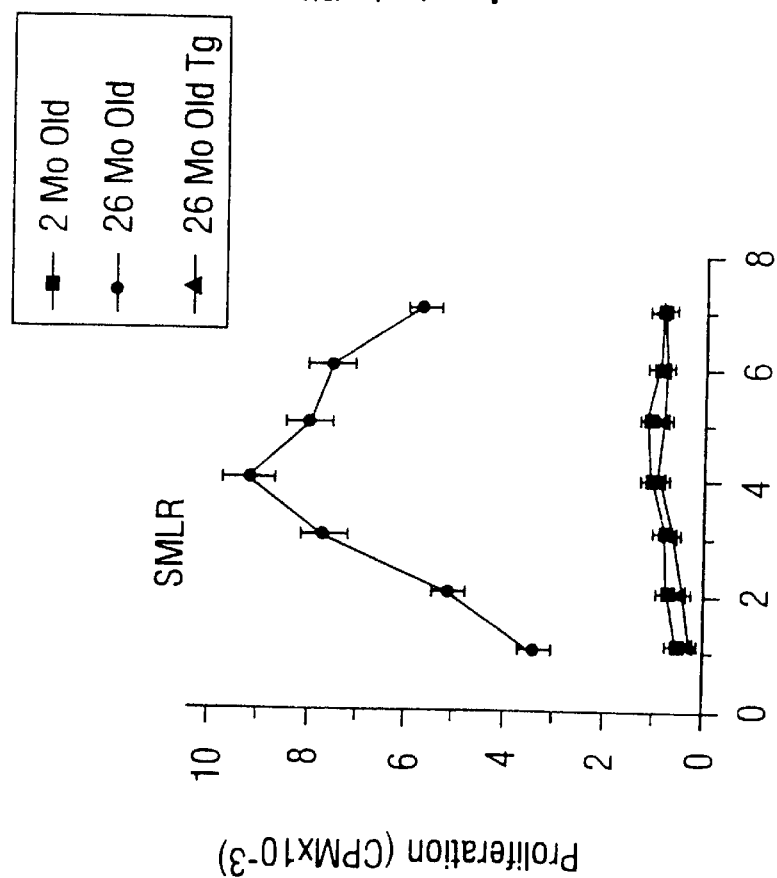
FIG. 7A. Effect of Anti-Fas and Fas Fusion Protein on SMLR-Induced Proliferation and Apoptosis. Lymphocyte suspensions ($10^6$/sample) were cultured in 96 well plates in the presence of IL-2 (50 $\mu$/ml). The proliferation was determined at the indicated times by $^3$H-Thymidine incorporation and apoptosis determined by the in situ nick translation method. This figure indicates the SMLR proliferative response.

Syngeneic Mixed Lymphocyte Response. Spleen cells from 2-month-old mice exhibited a weak SMLR characterized by a minimal proliferative response (FIG. 7A). This was not due to an absence of IL-2 since the cells were cultured in the presence of 50 μ/ml of IL-2. In contrast, there was a strong proliferation after syngeneic mixed lymphocyte (SMLR) reaction which peaked at 96 hours using enriched spleen T cells of 26-month-old mice. The SMLR response of spleen cells from 26-month-old CD2-fas transgenic mice was similar to that observed in 2-month-old mice. On days 1 and 3 of the SMLR, there was minimum apoptosis (20–30%) in all three groups of mice. However at day 5 and 7, apoptosis increased to 60–70% of spleen cells in both 2-month-old mice or 26-month-old CD2-fas transgenic mice (FIG. 7B). In contrast, the percentage of cells undergoing apoptosis remained relatively low in aged mice on day 5 and 7 of the SMLR.

Figure 7F:
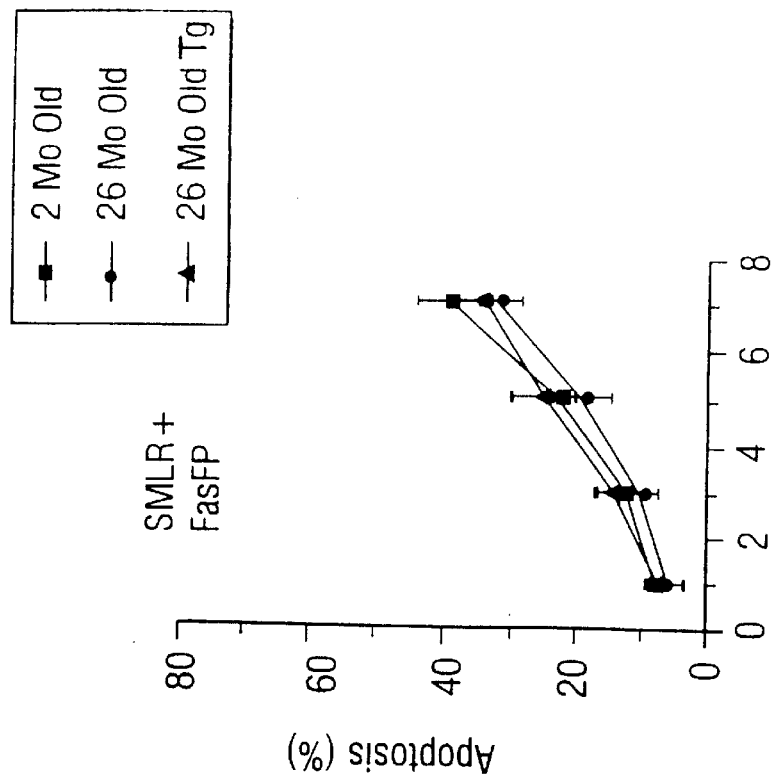
FIG. 7F. Apoptosis of SMLR stimulated cells carried out in the presence of Fas fusion protein (0.1 $\mu$g/ml).
Figure 7E:
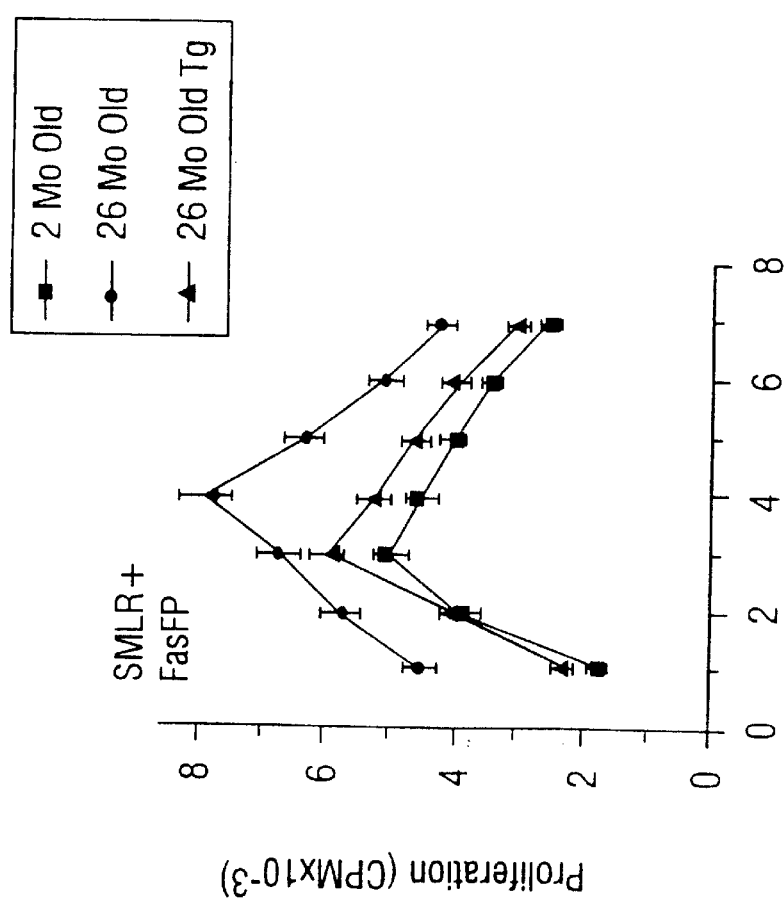
FIG. 7E. SMLR proliferative response in the presence of Fas fusion protein (FasFP, 0.1 $\mu$g/ml).

To determine if the cells undergoing the SMLR response were sensitive to Fas mediated apoptosis, the SMLR was carried out in the presence of 1 μg/ml of purified anti-Fas antibody. Anti-Fas antibody did not prevent the SMLR proliferative responses by spleen cells from 26-month-old non-transgenic mice and had no effect on the percentage of cells undergoing apoptosis (FIG. 7C and FIG. 7D). Blocking of the Fas-Fas ligand interaction during the SMLR with a Fas fusion protein increased the initial proliferative response and prevented the increased apoptosis in young, 2-month-old mice and in 26-month-old CD2-fas transgenic mice (FIG. 7E and FIG. 7F). In contrast, the SMLR and apoptosis response from 26-month-old mice was not significantly affected by the presence of Fas fusion protein. These results indicate that the increased SMLR exhibited by spleen cells from 26-month-old mice is associated with defective Fas signaling and apoptosis which is present in 2-month-old mice and in 26-month-old CD2-fas transgenic mice. These results indicate that the increased SMLR in aged mice is due to a defect in apoptosis. This failure could not be corrected by stimulation with anti-Fas antibody, consistent with the finding that Fas expression is defective on T cells from aged mice.

Figure 8A:
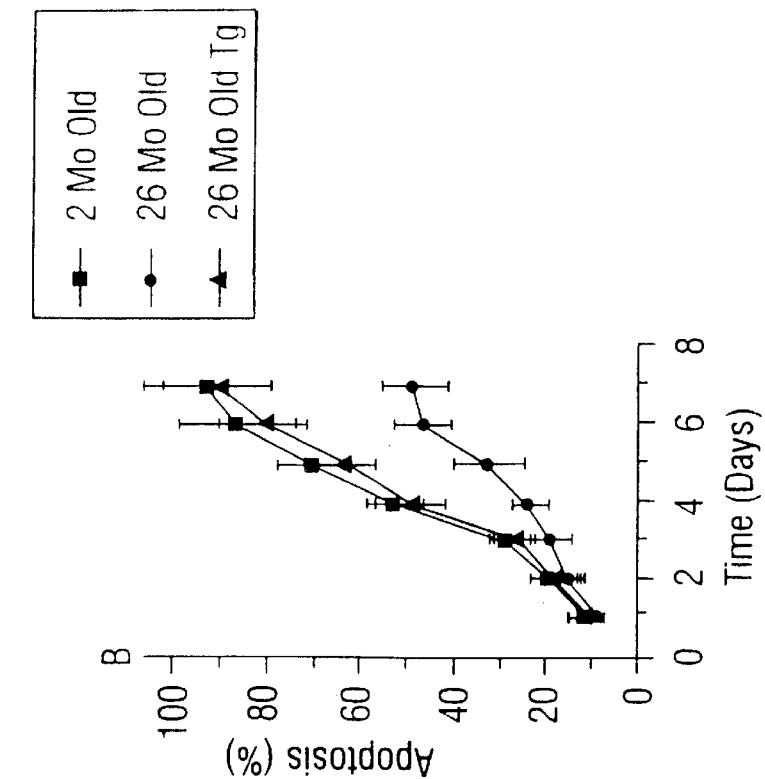
FIG. 8A. Correction of Proliferation and Apoptosis After CD3 Stimulation in Aged CD2-Fas Transgenic Mice. Lymphocyte suspensions ($10^6$/sample) were cultured in 96 well plates that had been precoated with anti-CD3 (10 $\mu$g/ml). The proliferation was determined at the indicated times by the $^3$H-Thymidine incorporation assay.
Figure 8B:
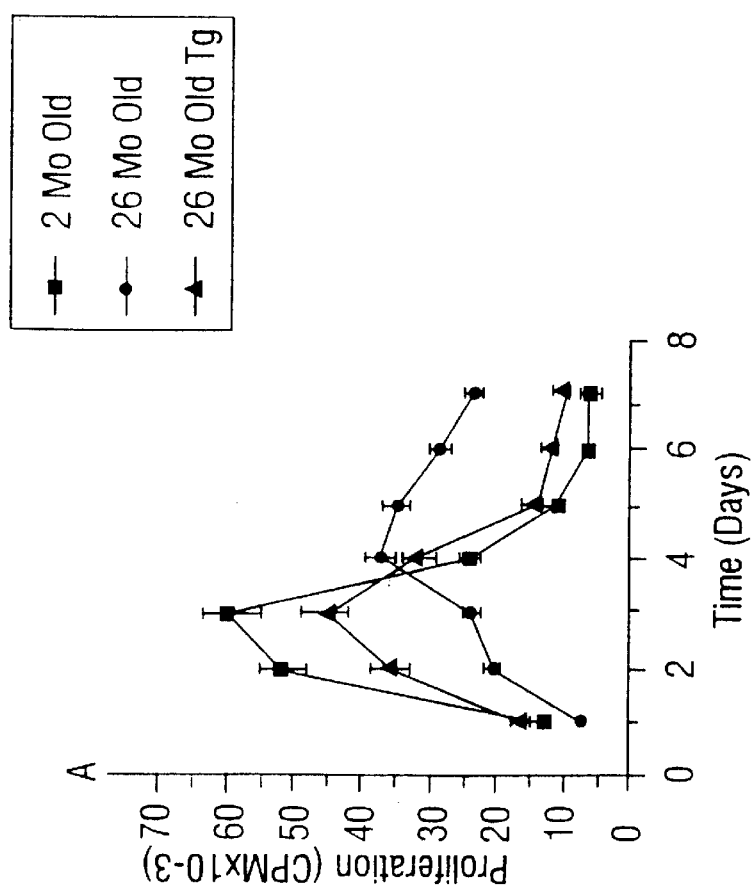
FIG. 8B. Apoptosis was determined by the in situ nick translation assay of single cell suspensions of lymphocytes as previously described (Vitetta et al., 1991). The results represent the mean +/– SEM for three separate mice assayed individually in triplicate culture wells.

Prevention of Age-Related Decrease in Proliferative and Apoptosis in CD2-fas Transgenic Mice. T cell proliferation after anti-CD3 cross-linking peaked at 72 hours in 2-month-old CD1 mice (FIG. 8A). In contrast, T cells from 26-month-old mice exhibited a decreased proliferative response after anti-CD3 cross-linking which peaked at 96 hours. The anti-CD3 proliferative responses in 26-month-old CD2-fas transgenic mice (and 2-month-old CD2-fas transgenic mice) were decreased but similar to those observed in 2-month-old mice with peak proliferation on day 3 followed by a decrease in proliferation. Apoptosis after anti-CD3 stimulation was increased in 2-month old CD1 mice and in 26-month-old CD2-fas transgenic mice compared to 26-month-old non transgenic mice (FIG. 8B).

Figure 9A:
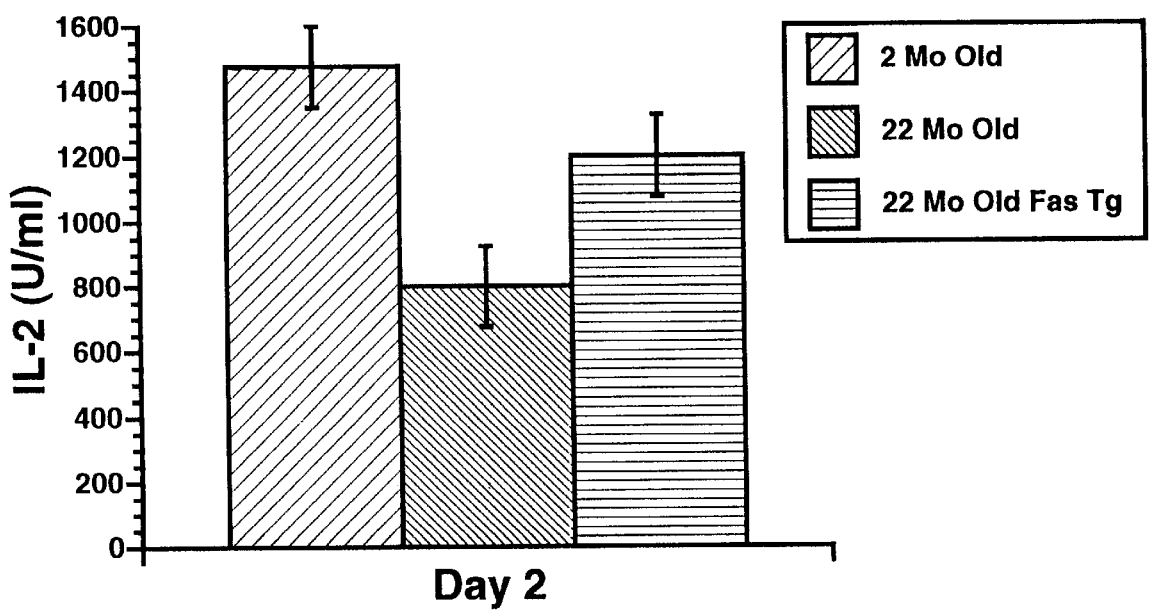
FIG. 9A. Correction of Cytokine Production After Anti-CD3 Crosslinking in Aged CD2-Fas Transgenic Mice. Lymphocyte suspensions ($2 \times 10^6$ cells/ml) from 22-month-old mice were cultured in 24 well plates that had been precoated with anti-CD3 (10 $\mu$g/ml). Cytokine concentrations were determined at the indicated times by ELISA. This figure represents IL-2 after 2 days culture.
Figure 9B:
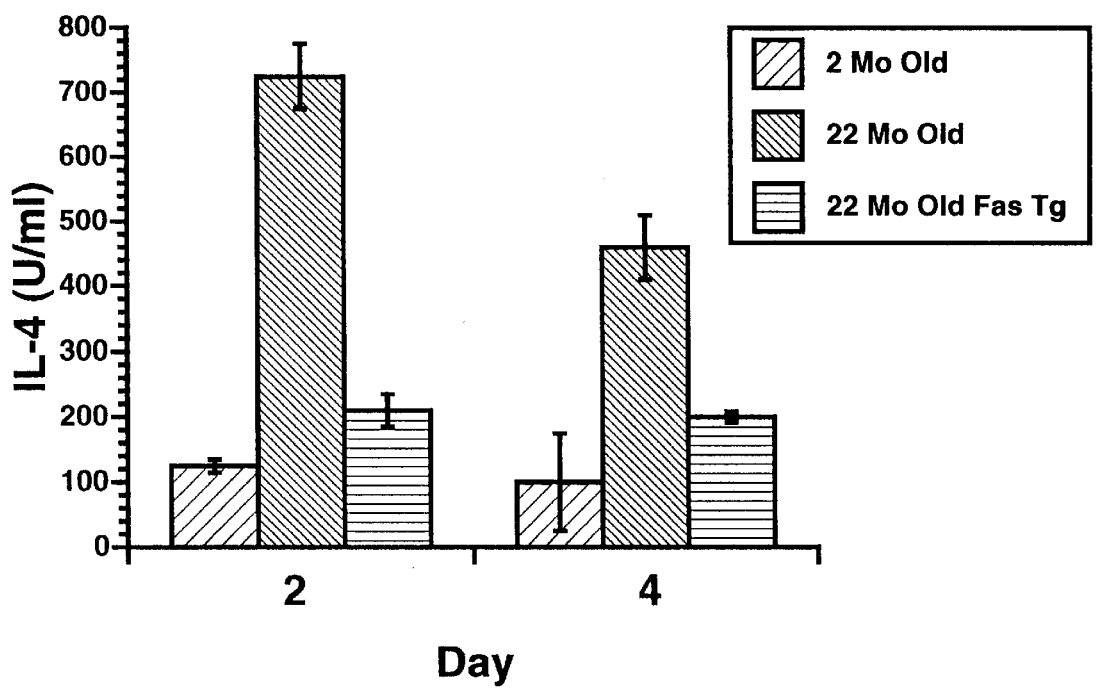
FIG. 9B. IL-4 after 2 and 4 days culture.
Figure 9C:
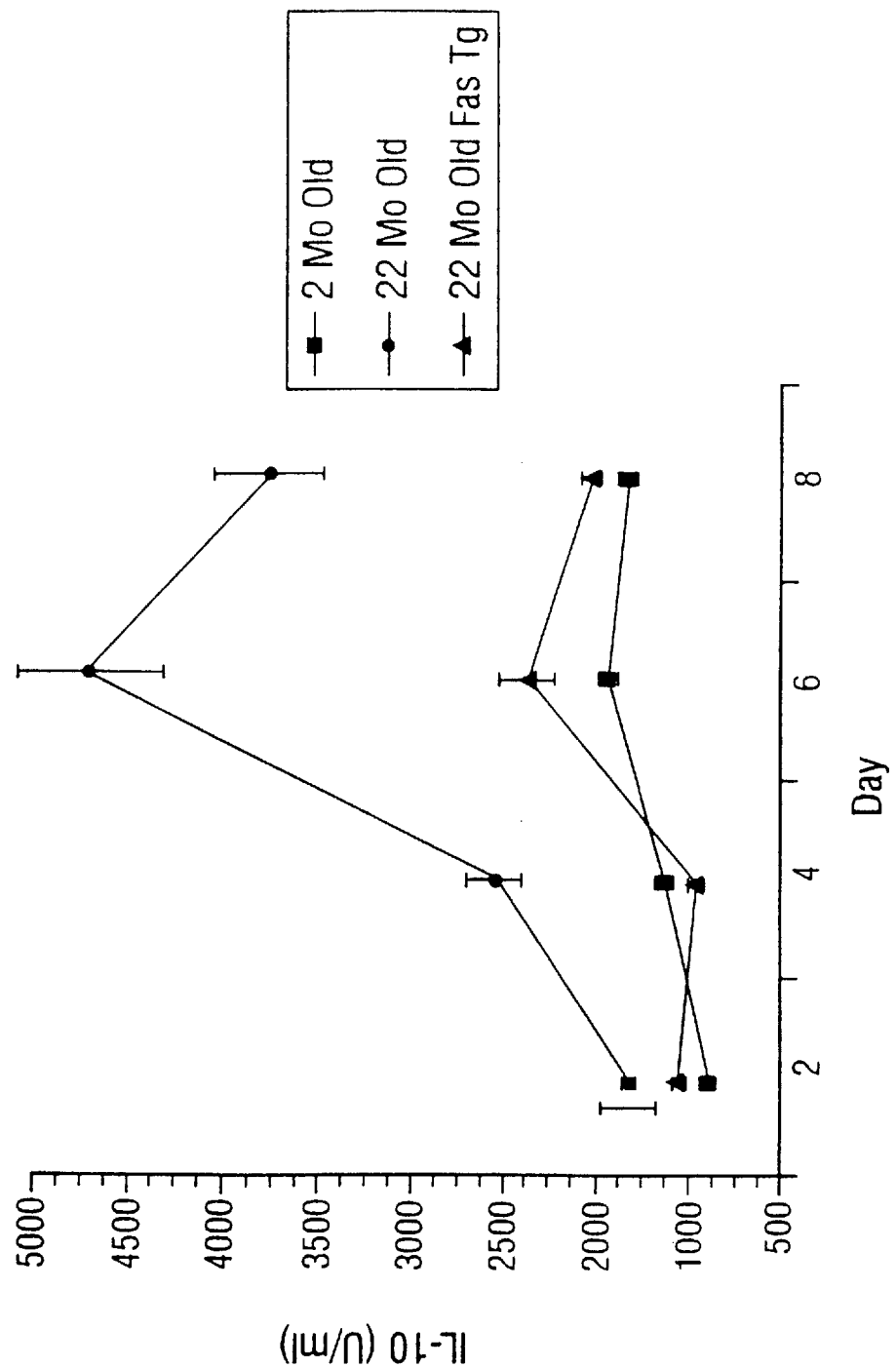
FIG. 9C. IL-10 at 2 to 8 days culture. Each data point represents the average of 5 mice/group, and the error bar represents the SEM.

Correction of Cytokine Response in CD2-fas Transgenic Aged Mice. Decreased IL-2 production after anti-CD3 crosslinking has been noted in old mice and humans (Flurkey et al., 1992; Kirschmann and Murasko, 1992; Song et al., 1993). The 50/% decrease in IL-2 production after anti-CD3 crosslinking in 22-month-old mice was partially corrected in 22-month-old CD2-fas transgenic (FIG. 9A). There was an increase in production of IL-4 on days 2 and 4 after anti-CD3 crosslinking in aged mice compared to 2-month-old mice, and this increase was partially prevented in 22-month-old CD2-fas transgenic mice (FIG. 9B). There was also an increased production of IL-10 which peaked on day 6 in 22-month-old mice compared to 2-month-old mice in response to anti-CD3 crosslinking (FIG. 9C). This increased IL-10 production was prevented in CD2-fas transgenic mice. These results indicate that the aged mice exhibit a shift toward a Th2 type cytokine response (IL-4, IL-10) rather than a Th1 cytokine response (IL-2), and that this shift can be prevented in CD2-fas transgenic aged mice.

Figure 10A:
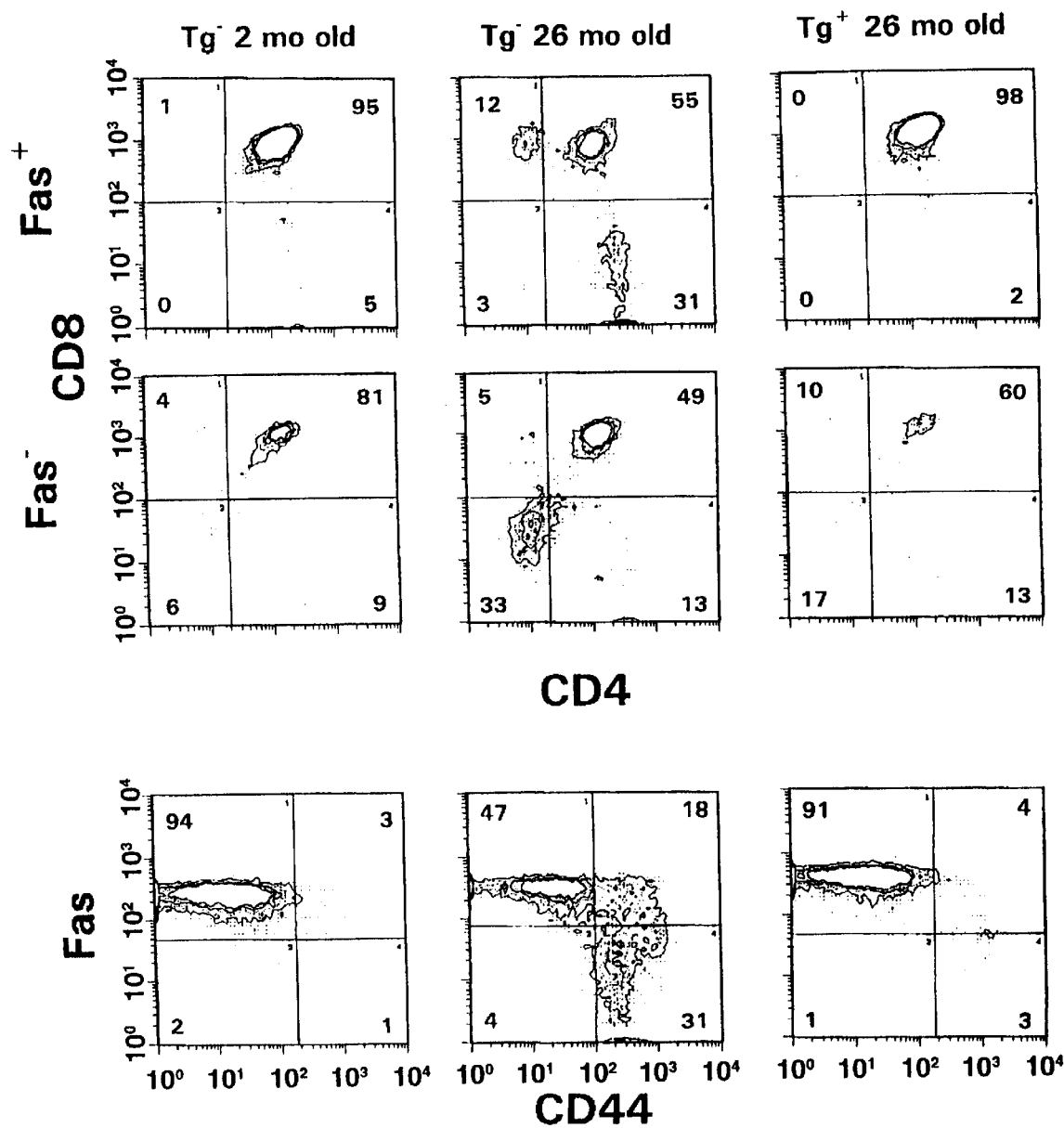
FIG. 10A. Correction of CD44 Expression on Thymocytes and Spleen Cells in Aged CD2-fas Transgenic Mice. Single cell suspensions of thymocytes and spleen cells from 2-month-old, 26-month-old, and 26-month-old Fas transgenic mice ($10^6$/sample) were analyzed for expression of CD4 and/or CD8, Fas and CD44. Thymocytes were labeled with anti-Fas, anti-CD4 and anti-CD8 or anti-Fas and anti-CD44. Fas$^+$ and Fas$^-$ thymocyte populations are defined as in FIG. 5.
Figure 10B:
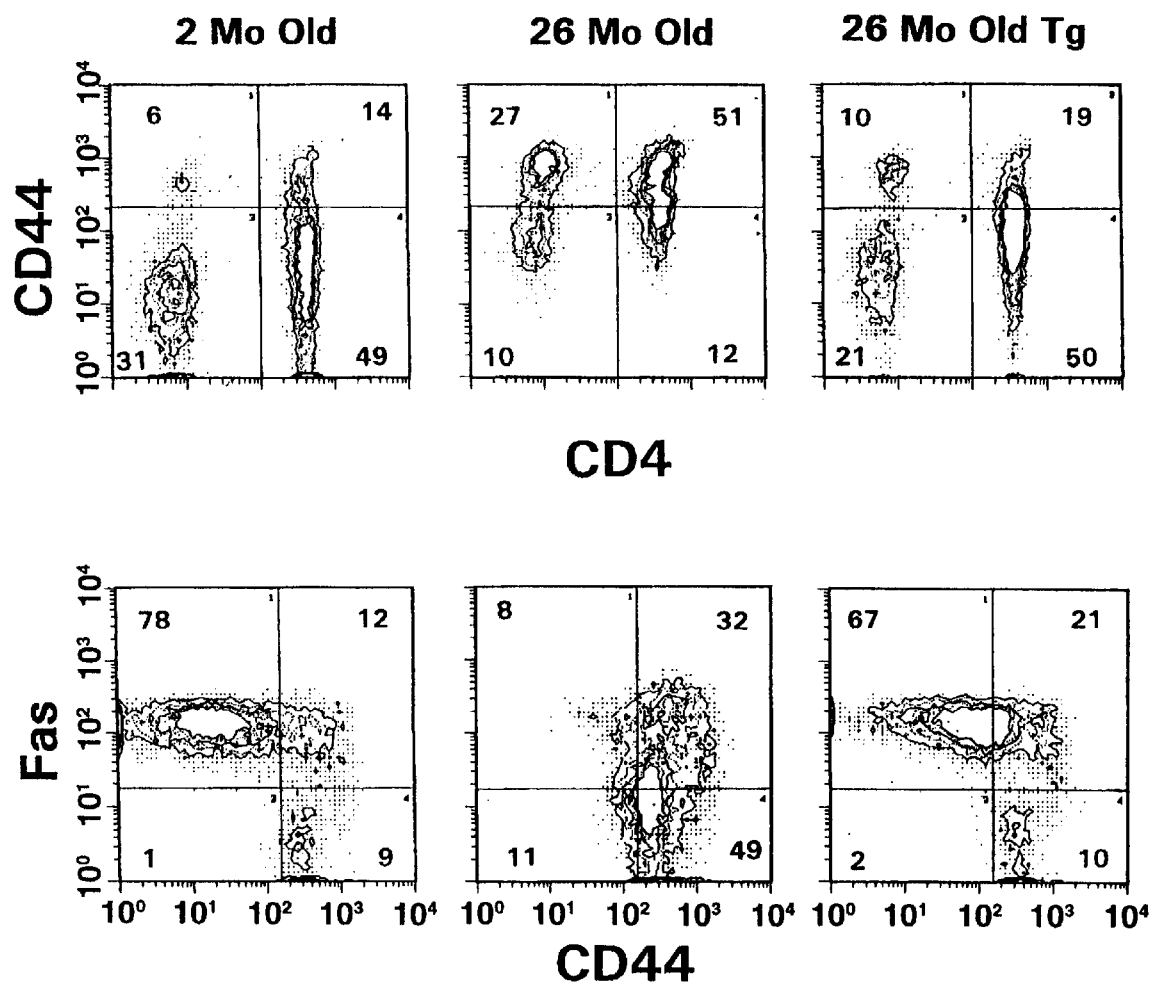
FIG. 10B. Enriched spleen T cells were labeled with anti-CD44, anti-CD4 and anti-Fas. The gates used to define lymphocyte populations are indicated by the vertical and horizontal lines. Viable cells (10,000 per sample) were analyzed by flow cytometry on a FACS-Scan with logarithmic scales.

Correction of CD44 Expression on Thymocytes and Spleen Cells. Thymocyte subpopulations exhibiting defective Fas expression were primarily $CD4^+CD8^+$ (double positive) and $CD4^-CD8^-$ (double negative) thymocytes in 26-month-old non-transgenic CD1 mice (FIG. 10A). Most of the thymocytes with low Fas expression exhibited increased expression of CD44. Thymocytes from 26-month-old CD2-fas transgenic mice were phenotypically similar to those from 2-month-old mice. Less than 20% of enriched T cells from the spleen of 2-month-old non-transgenic mice express CD44, and approximately 90% were $Fas^+$. In 26-month-old non-transgenic CD1 mice, 60% of enriched spleen T cells were $Fas^-$ and approximately 80% were $CD44^+$. In 26-month-old Fas-transgenic mice, expression of CD44, CD4 and Fas was similar to that observed in 2-month-old mice.

Figure 11A:
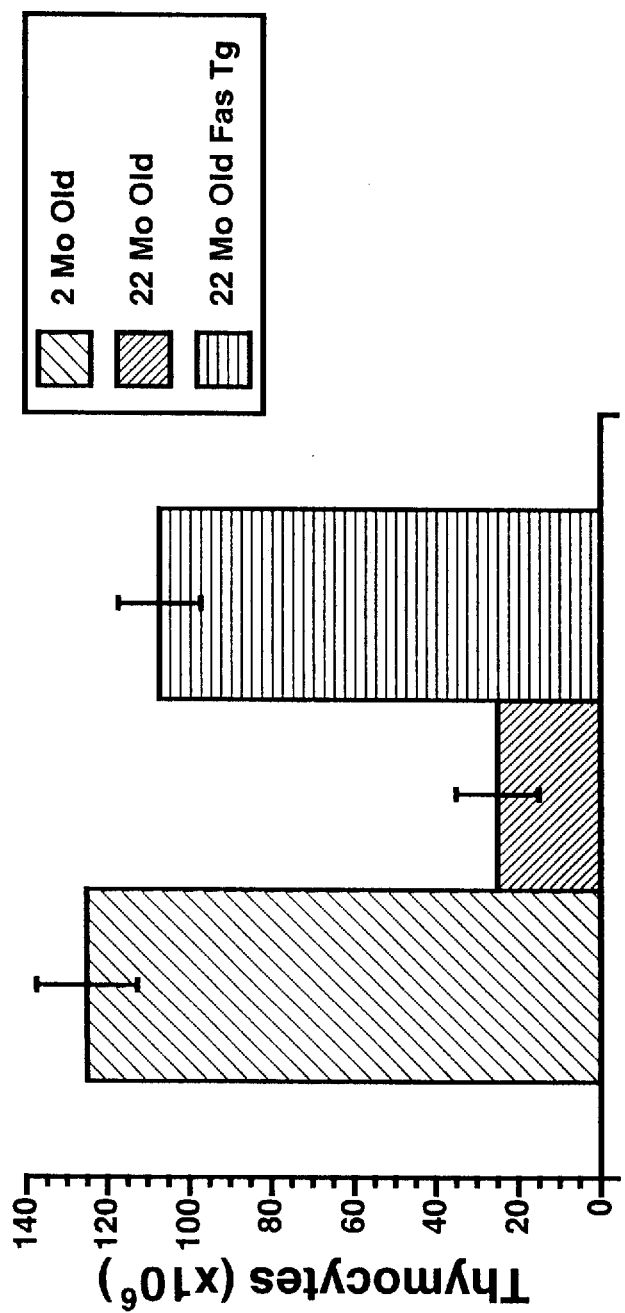
FIG. 11A. Thymocyte Cell Count and Apoptosis After Anti-CD3 Crosslinking. Single cell suspensions of thymocytes were prepared from 2-month-old, 22-month-old, or 22-month-old CD2-fas transgenic mice. Thymocyte suspensions ($10^6$/sample) were cultured in 96 well plates that had been precoated with anti-CD3 (10 $\mu$g/ml). This figure indicates the total number of thymocytes.
Figure 11B:
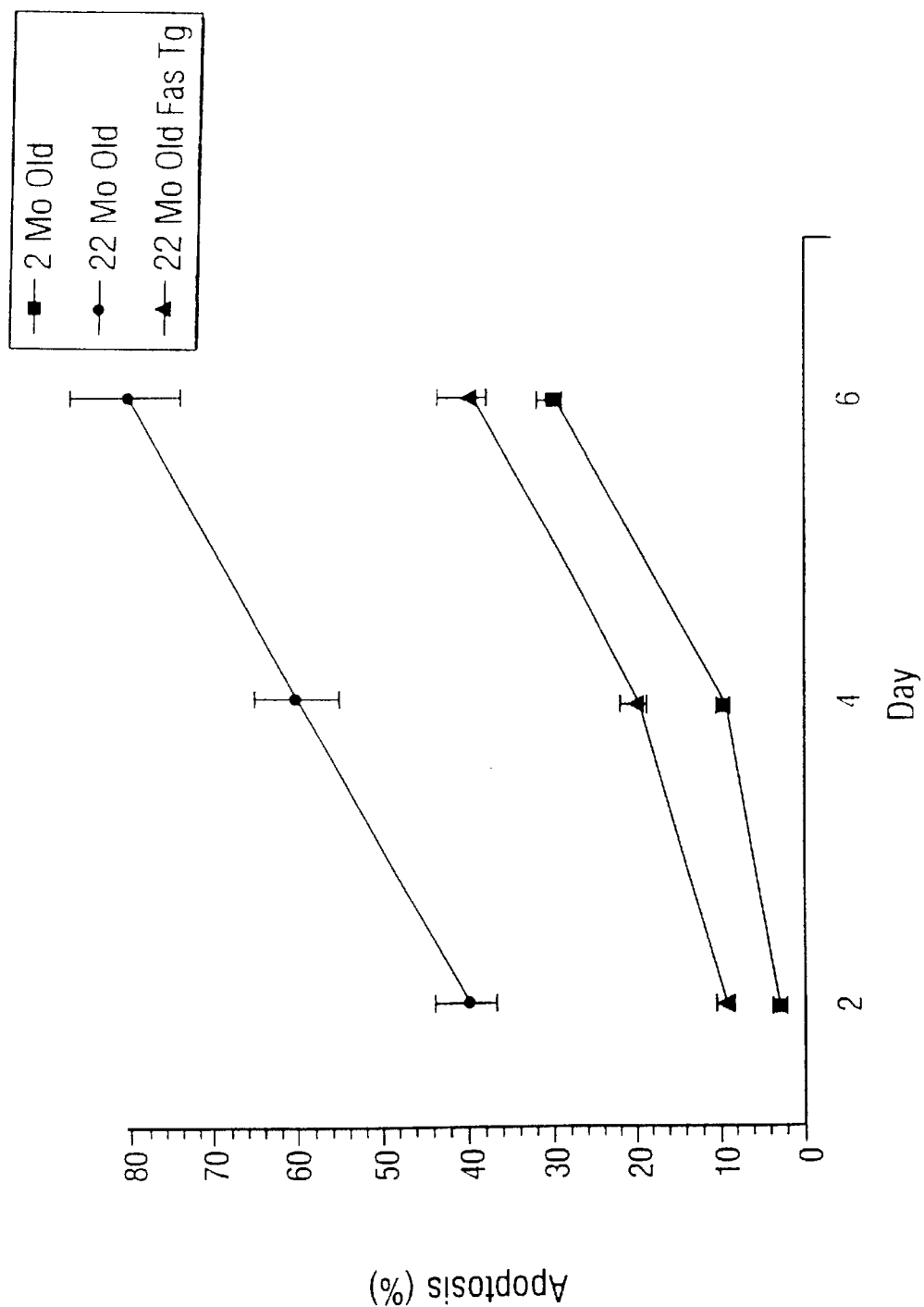
FIG. 11B. Percentage of thymocytes undergoing apoptosis at different time points after CD3 stimulation as determined by the in situ nick translation method. Each data point represents the average of 5 mice/group, and the error bar represents the SEM.

Prevention of Thymic Involution in Aged CD2-fas Transgenic Mice. There was a markedly decreased number of thymocytes in 22-month-old CD1 mice compared to 2-month-old CD1 mice which was prevented in the presence of the 22-month-old CD2-fas transgenic mice (FIG. 11A). Consistent with the finding of increased thymocyte number in young and aged CD2 Fas transgenic mice, thymocyte apoptosis was decreased in young and aged CD2-fas transgenic mice on days 2–6 after CD3 crosslinking (FIG. 11B). In contrast, in 22-month-old mice, there was increased apoptosis on days 2–6 after CD3 crosslinking, suggesting high utilization of programmed cell death mechanisms within the aged thymus. These results indicate that the CD2-fas transgene might provide an intrathymic signal for thymic development thereby preventing apoptosis after CD3 crosslinking in vitro.

EXAMPLE 4

Fas Allows T cell Proliferation

To determine whether defective Fas expression allows excessive proliferation of T cells, $5 \times 10^5$ total spleen cells from MRL-+/+ and -lpr/lpr mice were cultured with 5 μg/ml of precoated anti-CD3 antibody in the absence or presence of 5 μg/ml of purified Fas-Ig fusion protein. The proliferation was determined by $^3H$ thymidine incorporation at various times after culture.

It was found that the proliferative response was increased and prolonged by addition of Fas-Ig fusion protein to cultures of +/+ spleen cells. In contrast, Fas-Ig fusion protein had no effect on the culture of CD3 stimulated spleen cells from lpr mice. These results suggest that: 1) The Fas-Ig fusion protein allows prolonged survival and proliferation of T cells after stimulation; 2) The Fas-Ig fusion protein neutralizes or binds to Fas-ligand in these culture systems; 3) Fas-Fas-ligand interaction play a key role in selection of cells destined to survive or undergo apoptosis after CD3 signaling.

This data suggests that since soluble Fas inhibits apoptosis after activation, soluble Fas could be used to maintain growth of T cells or other cells susceptible to Fas apoptosis. Such maintenance could be in vivo, or it could be in vitro, e.g. in the maintenance of T cells. This imparts yet another practical usefulness to the present invention as the culture and maintenance of T cells is known to be technically difficult.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adachi, M., R. Watanabe-Fukunaga, and S. Nagata. 1993. Aberrant transcription caused by the insertion of an early transposable element in an intron of the Fas antigen gene of lpr mice. *Proc. Natl. Acad. Sci. U.S.A.* 90:1756.

Adelman et al. (1983) *DNA* 2:183 al-Rayes, H., W. Pachas, N. Mirza, D. J. Ahern, R. S. Geha, and D. Vercelli. 1992. IgE regulation and lymphokine patterns in aging humans. *J. Allergy Clin. Immunol.* 90:630.

Biedenkapp, H., U. Borgmeyer, A. E. Sippel, and K. H. Klempanuer. 1988. Viral myb oncogene encodes a sequence specific DNA binding activity. *Nature* 335:835.

Brutlag, D. L. et al. (1990) *CABS,* 6:237–245.

Candore, G., G. DiLorenzo, C. Caruso, M. A. Modica, A. T. Colucci, G. Crescimanno, A. Ingrassia, G. B. Sangiorgi, and A. Salerno. 1992. The effect of age on mitogen responsive T cell precursors in human beings is completely restored by interleukin-2. *Mech. Age. & Dev.* 63:297.

Cheng, J., T. Zhou, C. Liu, J. P. Shapiro, M. J. Brauer, M. C. Kiefer, P. J. Barr, and J. D. Mountz. 1994. Protection from Fas-mediated apoptosis by a soluble form of the Fas molecule. *Science.* 263:1759.

Chodosh, L. A., A. S. Baldwin, R. W. Carthew, and P. A. Sharp. 1988. Human CCAAT-binding proteins have heterozygous subunits. *Cell* 52:11.

Chomcynski, P., and N. Sacchi. 1987. Single-step method of RNA isolation by acid guanidinium thiocyanate-phenol-chloroform extract. *Anal. Biochem.* 162:156–159.

Cillari, E., S. Milano, M. Dieli, F. Arcoleo, R. Perego, F. Leoni, G. Gromo, A. Severn, and F. Y. Liew. 1992. Thymopoietin reduces the susceptibility of aged mice to cutaneous leishmaniasis by modulating CD4 T-cell subsets. *Immunology.* 76:362.

Clarke, A. R., C. A. Purdie, D. J. Harrison, R. G. Morris, C. C. Bird, M. L. Hooper, and A. H. Wyllie. 1993. Thymocyte apoptosis induced by p53-dependent and independent pathways. *Nature.* 362:849.

Cohen, A. S., W. E. Renolds, E. C. Franklin, J. P. Kulka, M. W. Ropes, and S. L. Wallace. 1971. Preliminary criteria for the classification of systemic lupus erythematosus. *Bull. Rheum. Dis.* 21:643.

Collins, M. K., G. R. Perkins, G. Rodriguez-Tarduchy, M. A. Nieto, and A. Lopez-Rivas. 1994. Growth factors as survival factors: regulation of apoptosis. *Bioessays.* 16:133.

Daynes, R. A., and B. A. Araneo. 1992. Natural regulators of T-cell lymphokine production in vivo. *J. Immunotherapy.* 12:174.

Dorn A., B. Durand, C. Marfing, M. Le Meur, C. Benoist, and D. Mathis. 1987. The conserved MHC class II boxes X and Y are transcriptional control elements and specifically bind nuclear proteins. *Proc. Natl. Acad. Sci. U.S.A.* 84:6249.

Eichenlaub, R. (1979) *J. Bacteriol* 138:559–566

Engelmann, H. D., M. Aderka, M. Rubinstein, D. Rotman, and D. Wallach. 1989. A tumor necrosis factor-binding protein purified to homogeneity from human urine protects cells from tumor necrosis factor toxicity. *J. Biol. Chem.* 264:11974–11980.

Ernst, D. N., W. O. Weigle, D. J. Noonan, D. N. McQuitty, and M. V. Hobbs. 1993. The age-associated increase in IFN-gamma synthesis by mouse $CD8^+$ T cells correlates with shifts in the frequencies of cell subsets defined by membrane CD44, CD45RB, 3G11, and MEL-14 expression. *J. Immunol.* 151:575.

Ernst, D. N., M. V. Hobbs, G. E. Torbett, A. L. Glasebrook, M. A. Rehse, K. Bottomly, K. Hayakawa, R. R. Hardy, and W. O. Weigle. 1990. Differences in the expression profiles of CD45RB, Pgp-1, and Cg11 splenic $CD4^+$ T cells from young and aged mice. *J. Immunol.* 145:1295.

Ershler, W. B. 1993. Interleukin-6: a cytokine for gerontologists. *J. Am. Geriatrics Soc.* 41:176.

Feinberg, A. P. and B. Vogelstein. 1984. A technique for radio-labeling DNA restriction endonuclease fragments to high specific activity. *Anal. Biochem.* 137:266–267.

Fernandez-Botran, R. 1991. Soluble cytokine receptors: their role in immunoregulation. *FASEB J.* 5:2567–2574.

Flurkey, K., R. A. Miller, and D. E. Harrison. 1992. Cellular determinants of age-related decrements in the T-cell mitogen response of B6CBAF1 mice. *J. Gerontol.* 47:B115.

Fourney, R. M., J. Miyakoshi, R. S. Day III, and M. C. Patterson. 1988. Northern blotting: efficient RNA staining and transfer. *Focus.* 10:5–7.

Fridkis-Hareli, M., L. Abel, and A. Globerson. 1992. Patterns of dual lymphocyte development in co-cultures of foetal thymus and lymphohaemopoietic cells from young and old mice. *Immunology.* 77:185.

Frizzera, G., Y. Kaneko, M. Sakurai. 1989. Angioimmunoblastic lymphadenopathy and related disorders: a retrospective look in search of definitions. *J. Leukemia.* 3:1–5.

Fuchs, P., S. Strehl, M. Dworzak, A. Himmler, and P. F. Ambros. 1992. Structure of the human TNF receptor 1 (p60) gene (TNFR1) and localization to chromosome 12p13. *Genomics* 13:219.

Gavrieli, Y., Y. Sherman, and S. A. Ben-Sasson. 1992. Identification of programmed cell death in situ via specific labeling of nuclear DNA fragmentation. *J. Cell Biol.* 119:493–503.

Gefter et al., *Somatic Cell Genet.* 3:231–236 1977.

Gewirtz, A. M., G. Anfossi, D. Venturelli, S. Valpreda, R. Sims, and B. Calabretta. 1989. $G_1/S$ transition in normal human T-lymphocytes requires the nuclear protein encoded by c-myb. *Science* 245:180.

Gmelig-Meyling, F., S. Dawisha, and A D. Steinberg. 1992. Assessment of in vivo frequency of mutated T cells in patients with systemic lupus erythematosus. *J. Exp. Med.* 175:297.

Goodwin, R. G., D. Friend, S. F. Ziegler, R. Jerzy, B. A. Falk, S. Gompel, D. Cosman, S. K. Dower, C. J. March, A. E. Namen, and L. S. Park. 1990. Cloning of the human and murine interleukin-7 receptors: demonstration of a soluble form and homology to a new receptor superfamily. *Cell* 60:941–951.

Goso, C., D. Frasca, and G. Doria. 1993. Effect of synthetic thymic humoral factor (THF-gamma 2) on T cell activities in immunodeficient ageing mice. *Clin. & Exp. Immunol.* 87:346.

Goya, R. G. 1992. Hormones, genetic program and immunosenescence. *Exp. Clin. Immunol.* 9:188.

Greaves, D. R., F. D. Wilson, G. Lang, and D. Kioussis. 1989. Human CD2 3'-flanking sequences confer high-level, T cell-specific, position-independent gene expression in transgenic mice. *Cell.* 56:979.

Hadden, J. W, P. H. Malec, J. Coto, and E. M. Hadden. 1992. Thymic involution in aging. Prospects for correction. *Ann. NY Acad. Sci.* 673:231.

Hadden, E. M., P. Malec, M. Sosa, and J. W. Hadden. 1992. Mixed interleukins and thymosin fraction V synergistically induce T lymphocyte development in hydrocortisone-treated aged mice. *Cell. Immunol.* 144:228.

Heyeck, S. D., and L. J. Berg. 1993. Developmental regulation of a murine T-cell-specific tyrosine kinase gene. *Proc. Natl. Acad. Sci. U.S.A.* 90:669.

Howard, C. J., P. Sopp, and K. R. Parsons. 1992. L-selectin expression differentiates T cells isolated from different lymphoid tissues in cattle but does not correlate with memory. *Immunol.* 77:228.

Inazawa, I., N. Itoh, T. Abe, and S. Nagata. 1992. Assignment of the human Fas antigen gene (FAS) to 10q24.1. *Genomics* 14:821.

Itoh, N. and S. Nagata. 1993. A novel protein domain required for apoptosis. *J. Biol. Chem.* 268:10932–10937.

Itoh, N., S. Yonehara, A. Ishii, M. Yonehara, S. -I. Mizushima, M. Sameshima, A. Hase, Y. Seto, and S. Nagata. 1991. The polypeptide encoded by the cDNA for human cell surface antigen Fas can mediate apoptosis. *Cell* 66:233–234.

Jones, N. C., P. Rigby, and E. B. Ziff. 1988. Trans-acting protein factors and the regulation of eukaryotic transcription: lessions from studies on DNA tumor virues. *Genes Dev.* 2:267.

Josimovic-Alasevic, O., T. Herrmann, and T. Diamantstein. 1988. Demonstrations of two distinct forms of released low-affinity type interleukin 2 receptors. *Eur. J. Immunol.* 18:1855–1857.

Kariv, I., F. G. Ferguson, and F. L. Confer. 1992. Age- and strain-related differences in murine spleen cell responses to different activation signals. *Cell. Immunol.* 140:67.

Kaufman, R. J. and P. A. Sharp. 1982. Construction of a modular dihydrofolate reductase cDNA gene: analysis of signals utilized for efficient expression. *Mol. Cell. Biol.* 2:1304–1319.

Kirschmann, D. A., and D. M. Murasko. 1992. Splenic and inguinal lymph node T cells of aged mice respond differently to polyclonal and antigen-specific stimuli. *Cell. Immunol.* 139:426.

Kohler and Milstein, *Nature* 256:495–497, 1975.

Kohler and Milstein, *Eur. J. Immunol.* 6:511–519, 1976.

Lang, G., D. Wotton, M. J. Owen, W. A. Sewell, M. H. Brown, D. Y. Mason, M. J. Crumpton, and D. Kioussis. 1988. The structure of the human CD2 gene and its expression in transgenic mice. *EMBO (Eur. Mol. Biol. Organ.) J.* 7:1675.

Lerner, A., T. Yamada, and R. A. Miller. 1989. Pgp-1$^{hi}$ T lymphocytes accumulate with age in mice and respond poorly to convanavalin A. *Eur. J. Immunol.* 19:977.

Li, Y. M., D. L. Brunke, R. Dantzer, and K. W. Kelley. 1992. Pituitary epithelial cell implants reverse the accumulation of $CD4^-CD8^-$ lymphocytes in thymus glands of aged rats. *Endocrinology.* 130:2703.

Lichter, P., H. Walczak, S. Weitz, I. Behrmann, and P. H. Krammer. 1992. The human APO-1 (APT) antigen maps to 10q23, a region that is syntenic with mouse chromosome 19. *Genomic* 14:179.

Loenen, W. A. M., L. A. Gravestein, S. Beumer, C. J. M. Melief, A. Hagemeijer, and J. Borst. 1992. Genomic organization and chromosomal localization of the human CD27 gene. *J. Immunol.* 149:3937.

Lowe, S. W., E. M. Schmitt, S. W. Smith, B. A. Osborne, and T. Jacks. 1993. p53 is required for radiation-induced apoptosis in mouse thymocytes. *Nature.* 362:847.

Mallett, S., and A. N. Barclay. 1991. A new superfamily of cell surface proteins related to never growth factor receptor. *Immunol. Today* 12.220-.

McElhaney, J. E., G. S. Meneilly, B. L. Beattie, C. D. Helgason, S. F. Lee, R. D. Devine, and R. C. Bleackley. 1992. The effect of influenza vaccination on IL2 production in healthy elderly: implications for current vaccination practices. *J. Gerontol.* 47:M3.

Mehr, R., L. Abel, P. Ubezio, A. Globerson, and Z. Agur. 1993. A mathematical model of the effect of aging on bone marrow cells colonizing the thymus. *Mech. Age. & Dev.* 67:159.

Messing et al. (1981) Third Cleveland Symposium on Macromoleculesand Recombinant DNA, Editor A. Walton, Elsevier, Amsterdam Mosley, B., M. P. Beckmann, C. J. March, R. L. Idzerda, S. D. Gimpel, T. VandenBos, D. Friend, A. Alper, D. Anderson, J. Jackson, J. M. Wignall, C. Smith, B. Gallis, J. E. Sims, D. Urdal, M. B. Widmer, and L. S. Park. 1989. The murine interleukin-4 receptor: molecular cloning and characterization of secreted and membrane bound forms. *Cell* 59:335–348.

Mount, S. M. 1982. A catalogue of splice junction sequences. *Nucleic. Acids Res.* 10:459.

Mountz, J. D., and A. D. Steinberg. 1989. Studies of c-myb gene regulation in MRL-lpr/lpr mice: Identification of a 5' c-myb nuclear protein binding site and high levels of binding factors in nuclear extracts of lpr/lpr lymph node cells. *J. Immunol.* 142:328.

Mountz, J. D., A. D. Steinberg, D. M. Klinman, H. R. Smith, and J. F. Mushinski. 1984. Autoimmunity and increased c-myb transcription. *Science* 226:1087.

Mysler, E., P. Bini, J. Drappa, P. Ramos, S. M. Friedman, P. H. Krammer, and K. B. Elkon. 1994. The apoptosis-1/Fas protein in human systemic lupus erythematosus. *J. Clin. Invest.* 93:1029.

Nagelkerken, L., A. Hertogh-Huijbregts, R. Dobber, and A. Drager. 1991. Age-related changes in lymphokine production related to a decreased number of $CD45RB^{hi}$ $CD4^+$ T cells. *Eur. J. Immunol.* 21:273.

Oehm, A., I. Behrmann, W. Falk, M. Pawlita, M. Li-Weber, S. Richards, J. Dhein, B. C. Trauth, H. Postingl, and P. H. Krammer. 1992. Purification and molecular cloning of the APO-1 cell surface antigen, a member of the TNF/NGF receptor superfamily. *J. Biol. Chem.* 267:10709–10715.

Okumura, M., Y. Fujii, Y. Takeuchi, K. Inada, K. Nakahara, and H. Matsuda. 1993. Age-related accumulation of LFA-1$^{high}$ cells in a CD8$^+$CD45RA high T cell population. *Eur. J. Immunol.* 23:1057.

Owen-Schaub, L. B., S. Yonehara, W. L. Crump III, and E. A. Grimm. 1992. DNA fragmentation and cell death is selectively triggered in activated human lymphocytes by Fas antigen engagement. *Cell. Immunol.* 140:197–205.

Patel, H. R., and R. A. Miller. 1992. Age-associated changes in mitogen-induced protein phosphorylation in murine T lymphocytes. *Eur. J. Immunol.* 22:253.

Powers, D. C., and R. B. Belshe. 1993. Effect of age on cytotoxic T lymphocyte memory as well as serum and local antibody responses elicited by inactivated influenza virus vaccine. *J. Infect. Dis.* 167:584.

Ramsdell, K., and D. H. Lynch. 1993. Fas transduces activation signals in normal human T lymphocytes. *J. Exp. Med.* 178:2231.

Reed, J. C., J. D. Alpers, P. C. Nowel, and R. G. Hoover. 1986. Sequential expression of protooncogenes during lectin-stimulated mitogenesis of normal human lymphocytes. *Proc. Natl. Acad. Sci. U.S.A.* 83:3982.

Rouvier, E., M. -F. Luciani, and P. Golstein. 1993. Fas involvement in Ca$^{2+}$- independent T cell-mediated cytotoxicity. *J. Exp. Med.* 177:195–500.

Saini, A., and Y. Sei. 1993. Age-related impairment of early and late events of signal transduction in mouse immune cells. *Life Sci.* 52:1759.

Saito K., T. Sakai, S. Mori, Y. Kobayashi, Y. Amemiya, S. Sakamoto, and Y. Miura. 1992. Clinicopathologic and therapuetic aspects of angioimmunoblastic lymphadenopathy-related lesions. *J. Cancer.* 69:1259–1267.

Sambrook et al. (1989). Molecular cloning: A laboratory manual. Cold Spring Harbor Laboratory. Cold Spring Harbor, N.Y.

Schall, T. J., M. Lewis, K. J. Koller, A. Lee, G. C. Rice, G. W. H. Wong, T. Gatanaga, G. A. Granger, R. Lentz, H. Raab, W. J. Kohr, and D. V. Goeddel. 1990. Molecular cloning and expression of a receptor for human tumor necrosis factor. *Cell* 61:361–370.

Schultz, L. D., Schweitzer, P. A., Rajan, T. V., Yi, T., Ihle, J. N., Matthews, R. J., Thomas, M. L., and Beier, D. R. 1993. Mutations at the murine motheaten locus are within the hemopoietic cell protein-tyrosine phosphatase (Hcph) gene. *Cell* 73:1145–1454.

Sehgal, A., N. Patil, and M. Chao. 1988. A constitutive promoter expression of the nerve growth factor receptor gene. *Mol. Cell. Biol.* 8:3160.

Seldin, M. F., J. D. Mountz, J. F. Mushinski, H. R. Smith, and A. D. Steinberg. 1989. IL-2 modulation of murine T-cell oncogene expression. *Proc. Soc. Exp. Biol. Med.* 184:186.

Shapiro, M. B., and P. Senapathy. 1987. RNA splice junctions of different classes of eukaryotes: sequence statistics and functional implications in gene expression. *Nucleic. Acids Res.* 15:7155.

Sheets, M. D., S. C. Ogg, M. P. Wichens. 1990. Point mutations in AAUAAA and the poly (A) addition site: effects on the accuracy and efficiency of cleavage and polyadenylation in vitro. *Nucleic. Acids Res.* 18:5799.

Shi, J., and R. A. Miller. 1993. Differential tyrosine-specific protein phosphorylation in mouse T lymphocyte subsets. Effect of age. *J. Immunol.* 151:730.

Smith, C. W. J., J. G. Patton, and B. Nadal-Ginard. 1989. Alternative splicing in the control of gene expression. *Annu. Rev. Genet.* 23:527–577.

Song, L., Y. H. Kim, R. K. Chopra, J. J. Proust, J. E. Nagel, A. A. Nordin, and W. H. Adler. 1993. Age-related effects in T cell activation and proliferation. *Exp. Gerontol.* 28:313.

Song, L. J., J. E. Nagel, F. J. Chrest, G. D. Collins, and W. H. Adler. 1993. Comparison of CD3 and CD2 activation pathways in T cells from young and elderly adults. *Aging.* 4:307.

Su, X., Wu, J., Zhou, T., and Mountz, J. D. 1994. Dephosphorylation of a 65 Kd protein delivers signals for Fas-mediated apoptosis. *Clin. Res.* 42:184 (1994).

Suda, T., T. Takahashi, P. Golstein, and S. Nagata. 1993. Molecular cloning and expression of the Fas ligand, a novel member of the tumor necrosis factor family. *Cell.* 75:1169.

Tabor, S., and C. C. Richardson. 1987. DNA sequence analysis with a modified bacteriophage T7 DNA polymerase. *Proc. Natl. Acad. Sci. U.S.A.* 84:4767.

Taga, T., and T. Kishimoto. 1993. Cytokine receptors and signal transduction. *FASEB J.* 7:3387–3396.

Takahashi, T., M. Tanaka, C. I. Brannan, N. A. Jenkins, N. G. Copeland, T. Suda, and S. Nagata. 1994. Generalized lymphoproliferative disease in mice, caused by a point mutation in the Fas ligand. *Cell.* 76:969.

Thoman, M. L., D. N. Ernst, M. V. Hobbs, and W. O. Weigle. 1993. T cell differentiation and functional maturation in aging mice. *Adv. Exp. Med. & Biol.* 330:93.

Trauth, B. C., C. Llas, A. M. J. Peters, S. Matzku, P. Moller, W. Falk, K. -M. Debatin, and P. H. Krammer. 1989. Monoclonal antibody-mediated tumor regression by induction of apoptosis. *Science* 245:301.

Tsai, S-F., D. I. K. Martin, L. I. Zon, A. D. D'Andrea, G. G. Wong, and S. H. Orkin. 1989. Cloning of cDNA for the major DNA-binding protein of the erythroid lineage through expression in mammalian cells. *Nature* 339:446.

Tsui, H. W., Siminovitch, K. A., Desouza, L, Tsui, F. W. L. 1993. Moth-eaten and viable motheaten mice have mutations in the hematopoietic cell phosphatase gene. *Nature Genet.* 4:124–129.

Van Houten, N., and R. C. Budd. 1992. Accelerated programmed cell death of MRL-lpr/lpr T lymphocytes. *J. Immunol.* 149:2513.

Vaux, D. L. 1993. Toward an understanding of the molecular mechanisms of physiological cell death. *Proc. Natl. Acad. Sci U.S.A.* 90:786–789.

Vitetta, E. S., M. T. Berton, C. Burger, M. Kepron, W. T. Lee, and X. -M, Yin. 1991. Memory B and T cells. *Annu. Rev. Immunol.* 9:193.

Watanabe-Fukunaga, R., C. I. Brannan, N. G. Copeland, N. A. Jenkins, and S. Nagata. 1992. Lymphoproliferation disorder in mice explained by defects in Fas antigen that mediates apoptosis. *Nature.* 356:314.

Watanabe-Fukunaga, R., C. I. Brannan, N. Itoh, S. Yonehara, N. G. Copeland, N. A. Jenkins, and S. Nagata. 1992a. The cDNA structure, expression, and chromosomal assignment of the mouse Fas antigen. *J. Immunol.* 148:1274–1297.

Weinberger et al. (1985) *Science,* 228:740–742.

Whisler, R. L., J. W. Williams, Jr., and Y. G. Newhouse. 1991. Human B cell proliferative responses during aging. Reduced RNA synthesis and DNA replication after signal transduction by surface immunoglobulins compared to B cell antigenic determinants CD20 and CD40. *Mech. Age. & Dev.* 61:209.

Whisler, R. L., B. Q. Liu, Y. G. Newhouse, J. D. Walters, M. B. Breckenridge, and I. S. Grants. 1991. Signal transduction in human B cells during aging: alterations in stimulus-induced phosphorylations of tyrosine and serine/threonine substrates and in cytosolic calcium responsiveness. *Lympho. & Cyto. Res.* 10:463.

Wichens, M. P., and P. Stephenson. 1984. Role of the conserved AAUAAA sequence: four AAUAAA point mutants prevent message RNA 3' end formation. *Science* 226:1045.

Witkowski, J., and R. A. Miller. 1993. Increased function of P-glycoprotein in T lymphocyte subsets of aging mice. *J. Immunol.* 150:1296.

Wu, J., T. Zhou, J. Zhang, J. He, W. C. Gause, and J. D. Mountz. 1994. Correction of accelerated autoimmune disease by early replacement of the mutated lpr gene with the normal Fas apoptosis gene in the T cells of transgenic MRL-lpr/lpr mice. *Proc. Natl. Acad. Sci. U.S.A.* 91:2344.

Wu, J., T. Zhou, J. He, and J. D. Mountz. 1993. Murine autoimmune disease due to integration of an endogenous retrovirus in an apoptosis gene. *J. Exp. Med.* 178:461–468.

Wylliams, G. T., C. A. Smith, W. Spooncer, T. M. Dexter, and D. R. Taylor. 1990. Hemopoietic colony stimulating factors promote cell survival by suppressing apoptosis. *Nature* 343:76–79.

Yonehara, S., A. Ishii, and M. Yonehara. 1989. A cell-killing monoclonal antibody (anti-Fas) to a cell surface antigen co-down regulated with the receptor of tumor necrosis factor. *J. Exp. Med.* 169:1747–1756.

Zacharchuk, C. M., M. Mercep, and J. D. Ashwell 1991. Thymocyte activation and death: a mechanism for molding the T cell repertoire. *Ann. N.Y. Acad. Sci.* 636:52.

Zacharchuk, C. M., M. Mercep, C. H. June, A. M. Weissman, and J. D. Ashwell. 1991. Variations in thymocyte susceptibility to clonal deletion during ontogeny. Implications for neonatal tolerance. *J. Immunol.* 147:460.

Zhou, T., H. Bluethmann, J. Eldridge, M. Brockhaus, K. Berry, and J. D. Mountz. 1991. Abnormal thymocyte development and production of autoreactive T cells in T cell receptor transgenic autoimmune mice. *J. Immunol.* 147:466.

Zhou, T., H. Bluethmann, J. Eldridge, K. Berry, and J. D. Mountz. 1993. Origin of CD4$^-$CD8$^-$B220$^+$ T cells in MRL-lpr/lpr mice. Clues from a T cell receptor beta transgenic mouse. *J. Immunol.* 150:3651.

Zhou, T., H. Bluethmann, J. Zhang, C. K. Edwards, and J. D. Mountz. 1992. Defective maintenance of T cell tolerance to a superantigen in MRL-lpr/lpr mice. *J. Exp. Med.* 176:1063.

What is claimed is:

1. A DNA segment having an isolated sequence region defined as the Fas gene promoter region.

2. The DNA segment according to claim 1, further defined as free of structural genes.

3. The DNA segment according to claim 1, wherein the promoter region comprises the transcription factor binding region c-myb.

4. The DNA segment according to claim 1, wherein the promoter region comprises the transcription factor binding region set forth in SEQ ID NO:8.

5. The DNA segment according to claim 1, wherein the promoter region comprises a transcription factor binding region set forth in SEQ ID NO:3.

6. The DNA segment according to claim 1, wherein the promoter region comprises a transcription factor binding region set forth in SEQ ID NO:4.

7. The DNA segment according to claim 1, wherein the promoter region comprises a transcription factor binding region set forth in SEQ ID NO:5.

8. The DNA segment according to claim 1, wherein the promoter region comprises a transcription factor binding region set forth in SEQ ID NO:6.

9. The DNA segment according to claim 1, wherein the promoter region comprises a transcription factor binding region set forth in SEQ ID NO:7.

10. The DNA segment according to claim 1, wherein the segment comprises the 5' promoter region of the human Fas gene.

11. The DNA segment according to claim 10, wherein the sequence region is the nucleic acid sequence as set forth by a contiguous sequence from SEQ ID No. 1.

12. The DNA segment according to claim 1, wherein said promoter region is operatively linked to an expressible DNA coding region.

13. The DNA segment of claim 12, wherein the expressible DNA coding region comprises a Fas cDNA.

14. A DNA molecule comprising one or more of the Fas promoter regions selected from the group consisting of SEQ ID No. 1, SEQ ID No. 3, SEQ ID No. 4, SEQ ID No. 5, SEQ ID No. 6, SEQ ID No. 7, and SEQ ID No. 8, operatively linked to a structural gene not ordinarily under the transcriptional control of said promoter regions, said structural gene and promoter regions being combined in a manner such that the structural gene is under the transcriptional control of the promoter regions, wherein an operatively linked heterologous promoter is required except in said DNA molecules comprising SEQ ID No. 1.

15. The DNA molecule of claim 14 wherein the selected structural gene comprises the structural gene for a growth factor, growth factor receptor, cytokine, nuclear regulatory factor, tumor suppressor, anti-cancer agent or a peptide hormone.

16. The DNA molecule of claim 15, wherein the selected structural gene is further defined as comprising the structural gene for TGFα, TGFβ, EGF, FGF, TNFα, p53, c-myc, c-fos, GCSF, or GMCSF.

17. A nucleic acid segment that comprises at least a 10 nucleotide long contiguous stretch that corresponds to a contiguous nucleic acid sequence of SEQ ID NO:1 excluding nucleotides 1273–1498.

18. The nucleic acid segment according to claim 17, further defined as comprising at least a 20 nucleotide long contiguous stretch that corresponds to a contiguous nucleic acid sequence of SEQ ID NO:1 excluding nucleotides 1273–1498.

19. The nucleic acid segment according to claim 18, further defined as comprising at least a 30 nucleotide long contiguous stretch that corresponds to a contiguous nucleic acid sequence of SEQ ID NO:1 excluding nucleotides 1273–1498.

20. The nucleic acid segment according to claim 19, further defined as comprising at least a 50 nucleotide long contiguous stretch that corresponds to a contiguous nucleic acid sequence of SEQ ID NO:1 excluding nucleotides 1273–1498.

21. The nucleic acid segment according to claim 20, further defined as comprising at least a 100 nucleotide long contiguous stretch that corresponds to a contiguous nucleic acid sequence of SEQ ID NO:1 excluding nucleotides 1273–1498.

22. The nucleic acid segment according to claim 17, further defined as a segment of up to 2000 nucleotides excluding nucleotides 1273–1498.

23. The nucleic acid segment according to claim 22, further defined as a segment of up to 50 nucleotides excluding nucleotides 1273–1498.

24. A vector comprising the DNA of claim 1.

25. The vector according to claim 24, wherein said vector is an adenovirus vector or retrovirus vector.

26. The vector according to claim 24, wherein said vector is adapted for transfer to a eukaryotic host cell.

27. The vector according to claim 24, wherein said vector is adapted for transfer to a prokaryotic host cell.

28. A vector comprising the DNA of claim 14.

29. A host cell transformed with the vector of claim 24.

30. A host cell transformed with the DNA segment according to claim 1.

31. The host cell according to claim 30, wherein said host cell is a eukaryotic host cell.

32. A host cell transformed with the DNA of claim 14, wherein the structural gene expresses a polypeptide or protein.

33. The host cell according to claim 32, wherein the polypeptide is Fas.

34. A method of expressing a DNA coding region in a host cell in vitro, said method comprising:

(a) introducing the vector of claim 28 into a host cell; and (b) maintaining said host cell under conditions effective to allow expression of the coding region.

35. The method according to claim 34, wherein the coding region encodes Fas.

36. The method according to claim 34, wherein the recombinant vector is dispersed in a pharmaceutical composition.

37. The method according to claim 34, wherein the recombinant vector is encapsulated in a liposome.

38. The method according to claim 34, wherein the recombinant vector is an adenovirus or a retrovirus.

39. A composition comprising a DNA segment according to claim 1, operatively linked to a DNA coding region encoding a polypeptide or peptide and means to deliver the composition into a mammalian cell in vitro for expression of a coding sequence.

40. The composition according to claim 39, wherein the DNA coding region encodes Fas.

41. The composition according to claim 39, wherein the DNA coding region is a heterologous coding sequence.

42. A method of regulating the expression of a structural gene in a host cell in vitro, comprising the steps of:

(a) introducing the vector of claim 28 into a host cell, said host cell having a transcription factor which binds to a site on said vector; and (b) expressing the polypeptide in the cell due to the presence of the transcription factor which binds to a site on said vector.

43. The method according to claim 42 wherein said structural gene encodes Fas.

44. The method according to claim 42, wherein the transcription factor is AP-1, CP2, GF-1, NF-Y, c-myb, or EBP20.

45. The method according to claim 42, wherein the structural gene is a heterologous coding sequence that encodes a cytotoxic compound.

46. The method according to claim 45, wherein the compound is an enzyme capable of converting a non-toxic pro-drug into a cytotoxic drug.

* * * * *